US009775838B2

(12) United States Patent
Keegan et al.

(10) Patent No.: US 9,775,838 B2
(45) Date of Patent: *Oct. 3, 2017

(54) NASAL DRUG PRODUCTS AND METHODS OF THEIR USE

(71) Applicants: Adapt Pharma Limited, Dublin (IE); Opiant Pharmaceuticals, Santa Monica, CA (US)

(72) Inventors: Fintan Keegan, Dublin (IE); Robert Gerard Bell, Clearwater, FL (US); Roger Crystal, Santa Monica, CA (US); Michael Brenner Weiss, New York, NY (US)

(73) Assignees: ADAPT PHARMA LIMITED, Dublin (IE); OPIANT PHARMACEUTICALS, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/589,090

(22) Filed: May 8, 2017

(65) Prior Publication Data

US 2017/0239241 A1  Aug. 24, 2017

Related U.S. Application Data

(63) Continuation of application No. 15/415,221, filed on Jan. 25, 2017, which is a continuation of application No. 15/183,441, filed on Jun. 15, 2016, now Pat. No. 9,561,177, and a continuation-in-part of application No. 14/950,707, filed on Nov. 24, 2015, now Pat. No. 9,468,747, which is a continuation of application No. 14/942,344, filed on Nov. 16, 2015, now Pat. No. 9,480,644, which is a continuation-in-part of application No. 14/659,472, filed on Mar. 16, 2015, now Pat. No. 9,211,253.

(60) Provisional application No. 62/274,536, filed on Jan. 4, 2016, provisional application No. 62/219,955, filed on Sep. 17, 2015, provisional application No. 61/953,379, filed on Mar. 14, 2014.

(51) Int. Cl.

| | |
|---|---|
| A61M 31/00 | (2006.01) |
| A61M 5/00 | (2006.01) |
| A61F 13/00 | (2006.01) |
| A61K 31/56 | (2006.01) |
| A61K 31/485 | (2006.01) |
| A61K 9/00 | (2006.01) |
| A61K 47/18 | (2017.01) |
| A61M 15/08 | (2006.01) |
| A61M 11/00 | (2006.01) |

(52) U.S. Cl.
CPC .......... *A61K 31/485* (2013.01); *A61K 9/0043* (2013.01); *A61K 47/186* (2013.01); *A61M 11/007* (2014.02); *A61M 15/08* (2013.01)

(58) Field of Classification Search
None
See application file for complete search history.

(56) References Cited

U.S. PATENT DOCUMENTS

| | | | |
|---|---|---|---|
| 4,181,726 A | 1/1980 | Bernstein | 424/260 |
| 4,464,378 A | 8/1984 | Hussain | 424/260 |
| 5,866,154 A | 2/1999 | Bahal et al. | 424/423 |
| 7,977,376 B2 | 7/2011 | Singh et al. | 514/450 |
| 9,192,570 B2 | 11/2015 | Wyse et al. | 514/23 |
| 9,211,253 B2 | 12/2015 | Crystal et al. | A61K 9/0043 |
| 9,468,747 B2 | 10/2016 | Crystal et al. | A61M 31/00 |
| 9,480,644 B2 | 11/2016 | Crystal et al. | A61K 9/0043 |
| 9,561,177 B2 * | 2/2017 | Keegan | |
| 9,629,965 B2 * | 4/2017 | Crystal | A61K 9/0043 |
| 2003/0077300 A1 | 4/2003 | Wermeling | 424/400 |
| 2006/0009447 A1 | 1/2006 | Merkus | 514/221 |
| 2006/0120967 A1 | 6/2006 | Namburi et al. | 424/45 |
| 2009/0017102 A1 | 1/2009 | Stinchcomb et al. | 424/449 |
| 2010/0113495 A1 | 5/2010 | Wermeling et al. | 514/282 |
| 2010/0168147 A1 | 7/2010 | Chapleo et al. | 514/282 |
| 2010/0331354 A1 | 12/2010 | Wermeling | 514/282 |
| 2011/0046172 A1 | 2/2011 | Chapleo et al. | 514/282 |
| 2012/0270895 A1 | 10/2012 | Wermeling | 514/282 |
| 2013/0023825 A1 | 1/2013 | Edwards et al. | 604/143 |
| 2015/0174061 A1 | 6/2015 | Wyse et al. | A61K 9/0043 |
| 2015/0258019 A1 | 9/2015 | Crystal et al. | A61K 9/0043 |
| 2016/0008277 A1 | 1/2016 | Crystal et al. | A61K 9/0043 |

FOREIGN PATENT DOCUMENTS

| | | |
|---|---|---|
| CN | 1575795 | 2/2005 |
| EP | 1681057 | 7/2006 |
| WO | WO 82/03768 | 11/1982 |
| WO | WO 98/30211 | 7/1998 |
| WO | WO 00/62757 | 10/2000 |
| WO | WO 00/74652 | 12/2000 |
| WO | WO 00/76474 | 12/2000 |
| WO | WO 01/58447 | 8/2001 |
| WO | WO 01/82931 | 11/2001 |
| WO | WO 02/11778 | 2/2002 |
| WO | WO 03/084520 | 10/2003 |
| WO | WO 2004/054511 | 7/2004 |
| WO | WO 2005/020906 | 3/2005 |
| WO | WO 2006/058022 | 6/2006 |
| WO | WO 2006/089973 | 8/2006 |

(Continued)

OTHER PUBLICATIONS

Aptar UnitDose and BiDose product information sheet, available at www.aptar.com/docs/pharma-prescription/uds-bds-datasheet.pdf, publication date unknown, last accessed Mar. 26, 2015.

(Continued)

*Primary Examiner* — Jeffrey T. Palenik
(74) *Attorney, Agent, or Firm* — Harness, Dickey & Pierce, P.L.C.

(57) ABSTRACT

Drug products adapted for nasal delivery, comprising a pre-primed device filled with a pharmaceutical composition comprising an opioid receptor antagonist, are provided. Methods of treating opioid overdose or its symptoms with the inventive drug products are also provided.

46 Claims, 7 Drawing Sheets

(56) References Cited

FOREIGN PATENT DOCUMENTS

| WO | WO 2007/083073 | 7/2007 | |
|----|----------------|--------|---|
| WO | WO 2009/040595 | 2/2009 | |
| WO | WO 2012/026963 | 3/2012 | |
| WO | WO 2012/094283 | 7/2012 | ............... A61K 9/12 |
| WO | WO 2012/156317 | 11/2012 | ............... A61K 9/00 |
| WO | WO 2014/016653 | 1/2014 | ............ A61K 31/485 |
| WO | WO 2015/095644 | 6/2015 | ............. A61K 47/12 |
| WO | WO 2015/136373 | 9/2015 | |
| WO | WO 2016/007729 | 1/2016 | |

OTHER PUBLICATIONS

TEVA Pharmaceuticals USA, Inc., "Notice of ANDA No. 209522 naloxone hydrochloride nasal spray, 4mg/spray, with paragraph IV certification concerning U.S. Pat. No. 9,468,747", dated Dec. 29, 2016.
Barton E D et al., "Efficacy of intranasal naloxone as a needleless alternative for treatment of opioid overdose in the prehospital setting," J Emerg Med 29:3, 265-71 (published Oct. 2005).
Barton E D et al., "Intranasal administration of naloxone by paramedics," Prehosp Emerg Care 6:1, 54-58 (published Jan. 2002).
Beletsky, L. et al., "Physicians_Knowledge of and Willingness to Prescribe Naloxone to Reverse Accidental Opiate Overdose: Challenges and Opportunities." Journal of Urban Health: Bulletin of the New York Academy of Medicine, 84(1):126-136 (published 2006).
Djupesland, P., (2013)., "Nasal drug delivery devices: characteristics and performance in a clinical perspective-a review". *Drug Deliv. and Transl. Res.* 3:42-62.
Doe-Simkins M et al., "Saved by the nose: bystander-administered intranasal naloxone hydrochloride for opioid overdose," Am J Public Health 99:5, 788-91 (published May 2009).
Dowling J et al., "Population pharmacokinetics of intravenous, intramuscular, and intranasal naloxone in human volunteers," Ther Drug Monit 30:4 490-96 (published Aug. 2008).
Heard C et al., "Intranasal flumazenil and naloxone to reverse over-sedation in a child undergoing dental restorations," Paediatr Anaesth 19:8 795-99 (published Aug. 2009).
Kelly A M et al., "Intranasal naloxone for life threatening opioid toxicity," Emerg Med J 19:4, 375 (published Jul. 2002).
Kelly A M et al., "Randomised trial of intranasal versus intramuscular naloxone in prehospital treatment for suspected opioid overdose," Med J Aust 182:1 24-27 (published Jan. 3, 2005).
Kerr D et al., "Randomized controlled trial comparing the effectiveness and safety of intranasal and intramuscular naloxone for the treatment of suspected heroin overdose," Addiction 104:12, 2067-74 (Epub Nov. 9, 2009).
Kundoor, V., et al., (2011). Effect of formulation- and administration-related variables on deposition pattern of nasal spray pumps evaluated using nasal cast. *Pharm. Res.* 28:189501904.
Krieter P. et al., Pharmacokinetic Properties and Human Use Characteristics of an FDA Approved Intranasal Naloxone Product for the Treatment of Opioid Overdose, J Clin Pharmacol, 2016, pp. 1-11.
Loimer N et al., "Nasal administration of naloxone for detection of opiate dependence," J Psychiatr Res 26:1, 39-43 (published Jan. 1992).
Loimer N et al., "Nasal administration of naloxone is as effective as the intravenous route in opiate addicts," Int J Addict 29:6, 819-27 (published Apr. 1994).
Makidon et al. (2010). "Characterization of stability and nasal delivery systems for immunization with nanoemulsion-based vaccines" *Journal of Aerosol Medicine and Pulmonary Drug Delivery* 23(2):77-89.
Merlin M A et al., "Intranasal naloxone delivery is an alternative to intravenous naloxone for opioid overdoses," Am J Emerg Med 28:3, 296-303 (Epub Jan. 28, 2010.).
Robertson T M, "Intranasal naloxone is a viable alternative to intravenous naloxone for prehospital narcotic overdose," Prehosp Emerg Care 13:4, 512-15 (Published Oct. 2009).

Walley A Y et al., "Opioid overdose prevention with intranasal naloxone among people who take methadone," J Subst Abuse Treat 44:2, 241-47 (Epub Sep. 12, 2012).
Walley, A Y et al, "Opioid overdose rates and implementation of overdose education and nasal naloxone distribution in Massachusetts: interrupted time series analysis," BMJ 346:f174, (Published Jan. 31, 2013).
Weber J M et al., "Can nebulized naloxone be used safely and effectively by emergency medical services for suspected opioid overdose?" Prehosp Emerg Care 16:2, 289-92 (Epub Dec. 22, 2011).
Wermeling D P et al., "A response to the opioid overdose epidemic: naloxone nasal spray," Drug Delivery Trans!. Res. 3:1, 63-74 (published Feb. 1, 2013).
Wermeling D P et al., "Opioid harm reduction strategies: focus on expanded access to intranasal naloxone," Pharmacotherapy 30:7, 627-31, 2010.
Teva Pharmaceuticals USA, Inc., "Notice of ANDA No. 209522 naloxone hydrochloride nasal spray, 4mg/spray, with paragraph IV certification concerning U.S. Pat. No. 9,211,253", dated Sep. 13, 2016.
International Search Report (ISR), dated Sep. 2, 2015 in International Application No. PCT/IB2015/000941, 4 pgs.
International Search Report (ISR) and Written Opinion (WO), dated Aug. 25, 2014 in International Application No. PCT/EP2014/064032 (WO 2015/000941) 11 pgs.
Notice of Allowance and Fees Due, dated Oct. 9, 2015 in U.S. Appl. No. 14/659,472, 9 pgs.
Notice of Allowance and Fees Due, dated Dec. 21, 2016 in U.S. Appl. No. 15/183,441, 15 pgs.
Corrected Notice of Allowance and Fees Due, dated Nov. 9, 2015 in U.S. Appl. No. 14/659,472, 9 pgs.
Office Action (Non-final), dated Aug. 22, 2016, issued in U.S. Appl. No. 15/183,441.
Middleton et al. (2011) "The pharmacodynamic and pharmacokinetic profile of intranasal crushed buprenorphine and buprenorphine/naloxone tablets in opioid abusers", *Addiction* 106(8): 1460-1473.
Third party observer comments from corresponding UK Application No. GB 1616616.7 dated Apr. 21, 2017.
Teva Pharmaceuticals USA, Inc., 'Notice of ANDA No. 209522 naloxone hydrochloride nasal spray, 4mg/spray, with paragraph IV certification concerning U.S. Pat. No. 9,561,177,' dated Mar. 17, 2017.
Ashton H et al., "Best evidence topic report. Intranasal naloxone in suspected opioid overdose," Emerg Med J 23:3, 221-23 (published Mar. 2006).
Bailey A M et al., "Naloxone for opioid overdose prevention: pharmacists' role in community-based practice settings," Ann. Pharmacother 48:5, 601-06 (published May 2014).
*ADAPT Pharma Operations Limited, et al. v. Teva Pharmaceuticals USA, Inc., et al.*, U.S. District Court for the District of New Jersey. Civ. Action No. 2:16-cv-07721 (Oct. 21, 2016); Exhibit A U.S. Pat. No. 9,211,253.
*ADAPT Pharma Operations Limited, et al. v. Teva Pharmaceuticals USA, Inc., et al.*, U.S. District Court for the District of New Jersey. Civ. Action No. 2:33-cv-00001 (Feb. 8, 2017); Exhibit A U.S. Pat. No. 9,468,747.
Notice of Allowance and Fees Due dated Oct. 9, 2015 now U.S. Pat. No. 9,211,253.
Notice of Allowance and Fees Due dated Nov. 9, 2015 now U.S. Pat. No. 9,211,253.
Notice of Allowance and Fees Due dated Apr. 12, 2016 now U.S. Pat. No. 9,468,747.
Notice of Allowance and Fees Due dated Jul. 26, 2016 now U.S. Pat. No. 9,468,747.
Examiner initiated interview summary dated Mar. 31, 2016 now U.S. Pat. No. 9,480,644.
Notice of Allowance and Fees Due dated Mar. 31, 2016 now U.S. Pat. No. 9,480,644.
Notice of Allowance and Fees Due dated Jul. 7, 2016 now U.S. Pat. No. 9,480,644.

* cited by examiner

NASAL DRUG PRODUCTS AND METHODS OF THEIR USE

CROSS-REFERENCE TO RELATED APPLICATIONS

This application is a continuation of Ser. No. 15/415,221, filed on 25 Jan. 2017, which is a continuation of Ser. No. 15/183,441, filed on Jun. 15, 2016, now U.S. Pat. No. 9,561,177, which is a continuation-in-part application of Ser. No. 14/950,707, filed on Nov. 24, 2015, now U.S. Pat. No. 9,468,747, which is a continuation of Ser. No. 14/942,344, filed on Nov. 16, 2015, now U.S. Pat. No. 9,480,644, which is a continuation-in-part application of Ser. No. 14/659,472, filed on Mar. 16, 2015, now U.S. Pat. No. 9,211,253, which claims benefit of Ser. No. 61/953,379, filed on Mar. 14, 2014. This application also claims benefit of Ser. No. 62/219,955, filed on 17 Sep. 2015 and Ser. No. 62/274,536, filed on 4 Jan. 2016. The entire disclosures of the applications identified in this paragraph are incorporated herein by references.

JOINT RESEARCH AGREEMENT

The subject matter disclosed and claimed herein was developed by or on behalf of LightLake Therapeutics Inc. and Adapt Pharma Operations Ltd., as parties to a joint research agreement, and as a result of activities undertaken within the scope of the joint research agreement. The joint research agreement was in effect on or before the effective filing date of the present claims.

FIELD

This disclosure generally relates to pharmaceutical compositions comprising an opioid receptor antagonist, medical devices for delivery of the pharmaceutical compositions, and methods of using the compositions and the medical devices.

BACKGROUND

This section provides background information related to the present disclosure which is not necessarily prior art.

Opioid receptors are G protein-coupled receptors (GPCRs) that are activated both by endogenous opioid peptides and by clinically important alkaloid analgesic drugs such as morphine. There are three principal types of opioid receptors: the δ-opioid receptor, the κ-opioid receptor, and the μ-opioid receptor. Opioids depress respiration, which is controlled principally through medullary respiratory centers with peripheral input from chemoreceptors and other sources. Opioids produce inhibition at the chemoreceptors via μ-opioid receptors and in the medulla via μ- and δ-opioid receptors. While there are a number of neurotransmitters mediating the control of respiration, glutamate and γ-aminobutyric acid (GABA) are the major excitatory and inhibitory neurotransmitters, respectively. Oxycodone and other opioid painkillers, as well as heroin and methadone are all implicated in fatal overdose.

In the United States, mortality rates closely correlate with opioid sales. In 2014, there were 47,055 drug overdose deaths in the United States, representing a 6.5% increase from 2013 as reported by Rudd et al. (2016) *Morbidity & Mortality Weekly Report* 64(50):1378-82 (starting at page 10) "Increases in Drug and Opioid Overdose Deaths—United States, 2000-2014." Over 28,000 of those were overdoses of heroin or prescription opioids, which represents nearly a four-fold increase since 1999. Drugs classed as prescription opioids include both typical analgesics, such as OxyContin® (oxycodone HCl controlled-release) and methadone (used in the treatment of dependence on other opioids such as heroin and also prescribed for pain), but the increase in the rate of drug overdose in recent years has been driven mainly by overdoses of prescription analgesics.

Naloxone is an opioid receptor antagonist that is approved for use by injection for the reversal of opioid overdose and for adjunct use in the treatment of septic shock. It is currently being used mainly in emergency departments and in ambulances by trained medical professionals. There have been efforts to expand its use by providing the drug to some patients with take-home opioid prescriptions and those who inject illicit drugs, potentially facilitating earlier administration of the drug.

U.S. Pat. No. 4,464,378 to Hussain reports a method for eliciting an analgesic or narcotic antagonist response in a warm-blooded animal, which comprises administering intranasally (IN) to said animal to elicit a narcotic antagonist response, a narcotic antagonist effective amount of naloxone.

WO 82/03768 to Hussain reports a composition that contains 1 mg of naloxone hydrochloride per 0.1 ml of solution adapted for nasal administration used in the treatment of narcotic induced respiratory depression (overdose) at a dosage approximately the same as that employed for intravenous (IV), intramuscular (IM) or subcutaneous (SQ) administration.

WO 00/62757 to Davies reports pharmaceutical compositions for IN or oral (PO) administration which comprise an opioid antagonist, such as naloxone for application by spray in the reversal of opioid depression for treatment of patients suffering from opioid over-dosage, wherein the spray applicator is capable of delivering single or multiple doses and suitable dosage units are in the range of 0.2 to 5 mg.

The use of nasal naloxone is not without controversy. For instance, Dowling et al. (Ther Drug Monit, Vol 30, No 4, August 2008) reported that naloxone administered intranasally displays a relative bioavailability of 4% only and concluded that the IN absorption is rapid but does not maintain measurable concentrations for more than an hour.

U.S. Pat. No. 9,192,570 to Wyse reports naloxone formulations for intranasal administration. Wyse reports (column 27, lines 29-37) that benzalkonium chloride is not suitable in such formulations, because it facilitates unacceptable degradation of the naloxone. Wyse recommends (lines 41-43) benzyl alcohol and paraben preservatives in place of benzalkonium chloride.

Thus, there remains a need for durable, easy-to-use, needleless devices with storage-stable formulations, that can enable untrained individuals to quickly deliver a therapeutically effective dose of a rapid-acting opioid antagonist to an opioid overdose patient. The therapeutically effective dose should be sufficient to obviate the need for the untrained individual to administer an alternative medical intervention to the patient, and to stabilize the patient until professional medical care becomes available.

SUMMARY

This section provides a general summary of the disclosure, and is not a comprehensive disclosure of its full scope or all of its features.

This disclosure provides an improved single-use, pre-primed device adapted for nasal delivery of a pharmaceutical solution to a patient comprising: at least about 4% (w/v) naloxone hydrochloride or a hydrate thereof, wherein the improvement comprises that the device is adapted to spray a round plume with an ovality ratio less than about 2, for example less than about 1.5.

In another embodiment, there is provided a mist comprising droplets of an at least 4% (w/v) naloxone hydrochloride solution, wherein no more than about 10%, for example no more than about 5%, of the droplets have a diameter less than 10 μm.

In yet another embodiment, there is provided an improved single-use, pre-primed device adapted for nasal delivery of a pharmaceutical solution to a patient comprising: at least about 4% (w/v) naloxone hydrochloride or a hydrate thereof; and between about 0.2% and about 1.2% (w/v) of an isotonicity agent, wherein the improvement comprises that the device is adapted to spray a round plume with an ovality ratio less than about 2.0.

In yet another embodiment, there is provided an improved single-use, pre-primed device adapted for nasal delivery of a pharmaceutical solution to a patient comprising: at least about 4% (w/v) naloxone hydrochloride or a hydrate thereof; and between about 0.005% and about 0.015% (w/v) of a preservative, wherein the improvement comprises that the device is adapted to spray a round plume with an ovality ratio less than about 2.0.

DETAILED DESCRIPTION

Definition

Figure 1:
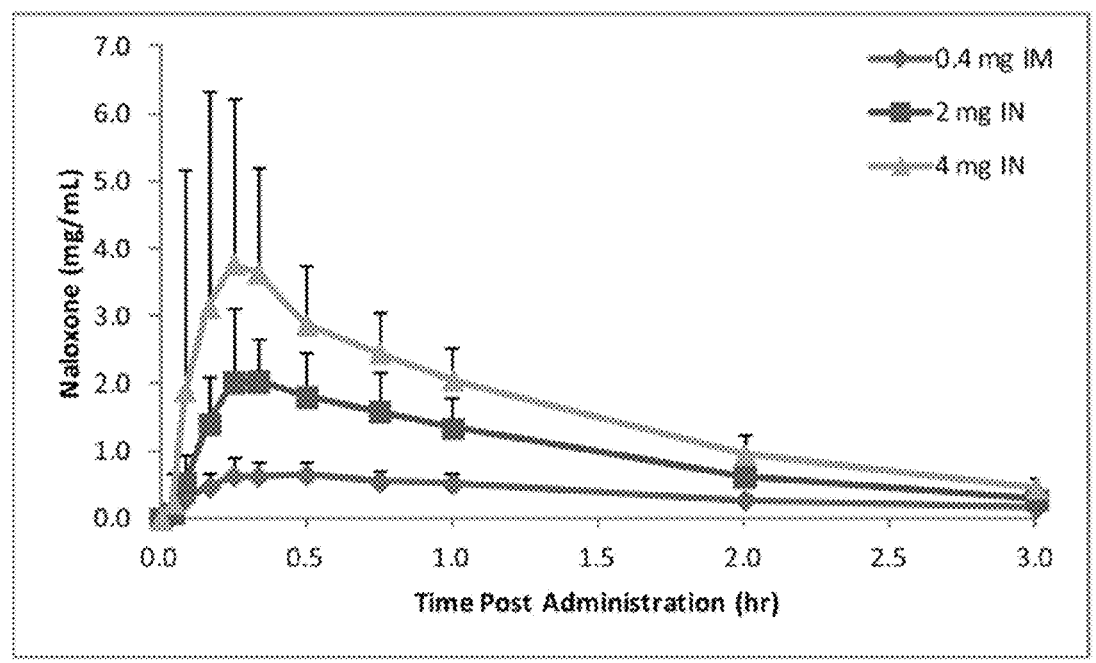
FIG. 1 shows the mean (±SD) naloxone plasma concentration following administration of 0.4 mg intramuscular (IM), 2 mg intranasal (IN), and 4 mg IN in 14 human subjects.
Figure 2:
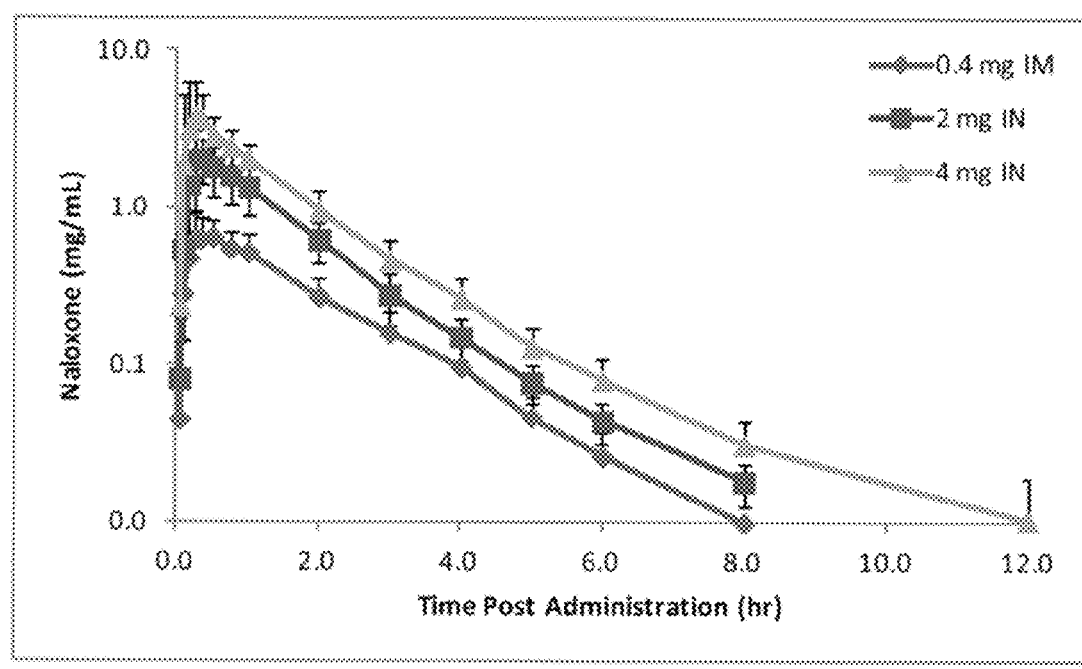
FIG. 2 shows the mean (±SD) naloxone plasma concentration with logarithmic transformation following administration of 0.4 mg intramuscular (IM), 2 mg intranasal (IN), and 4 mg IN in 14 human subjects.

For clarity and consistency, the following definitions will be used throughout this patent document.

The term "active ingredient" or "pharmaceutically active compound" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The term "actuation," as used herein, refers to operation of the device such that the pharmaceutical composition is delivered therefrom.

The term "agonist," as used herein, refers to as used herein refers to a moiety that interacts with and activates a receptor, and thereby initiates a physiological or pharmacological response characteristic of that receptor. The term "antagonist," as used herein, refers to a moiety that competitively binds to a receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist.

The term "antimicrobial preservative," as used herein, refers to a pharmaceutically acceptable excipient with antimicrobial properties which is added to a pharmaceutical composition to maintain microbiological stability.

The term "AUC," as used herein, refers to the area under the drug plasma concentration-time curve. The term "$AUC_{0-t}$," as used herein, refers to the area under the drug plasma concentration-time curve from t=0 to the last measurable concentration. The term "$AUC_{0-\infty}$," as used herein, refers to the area under the drug plasma concentration-time curve extrapolated to ∞. The term "$AUC_{0-t/D}$," as used herein, refers to the $AUC_{0-t}$ normalized to 0.4 mg IM naloxone. The term "$AUC_{0-\infty/D}$," as used herein, refers to the $AUC_{0-\infty}$ normalized to 0.4 mg IM naloxone The term "bioavailability (F)," as used herein, refers to the fraction of a dose of drug that is absorbed from its site of administration and reaches, in an unchanged form, the systemic circulation. The term "absolute bioavailability" is used when the fraction of absorbed drug is related to its IV bioavailability. It may be calculated using the following formula:

$$F = \frac{AUC_{extravascular}}{AUC_{intravenous}} \times \frac{Dose_{intravenous}}{Dose_{extravascular}}$$

The term relative bioavailability ($F_{rel}$) is used to compare two different extravascular routes of drug administration and it may be calculated using the following formula:

$$F_{rel} = \frac{AUC_{extravascular1}}{AUC_{extravascular2}} \times \frac{Dose_{extravascular2}}{Dose_{extravascular1}}$$

The term "clearance (CL)," as used herein, refers to the rate at which a drug is eliminated divided by its plasma concentration, giving a volume of plasma from which drug is completely removed per unit of time. CL is equal to the elimination rate constant (λ) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "$C_{max}$," as used herein, refers to the maximum observed plasma concentration. The term "$C_{max/D}$," as used herein, refers to $C_{max}$ normalized to 0.4 mg IM naloxone.

The term "coefficient of variation (CV)," as used herein, refers to the ratio of the sample standard deviation to the sample mean. It is often expressed as a percentage.

The term "confidence interval," as used herein, refers to a range of values which will include the true average value of a parameter a specified percentage of the time.

The term "device," as used herein, refers to an apparatus capable of delivering a drug to patient in need thereof.

The term "delivery time," as used herein, refers to the amount of time that elapses between a determination made by a healthcare professional, or an untrained individual that an individual is in need of nasal delivery of an opioid antagonist and completion of the delivery.

The term "elimination rate constant (λ)," as used herein, refers to the fractional rate of drug removal from the body. This rate is constant in first-order kinetics and is independent of drug concentration in the body. λ is the slope of the plasma concentration-time line (on a logarithmic γ scale). The term "$\lambda_z$," as used herein, refers to the terminal phase elimination rate constant, wherein the "terminal phase" of the drug plasma concentration-time curve is a straight line when plotted on a semilogarithmic graph. The terminal phase is often called the "elimination phase" because the primary mechanism for decreasing drug concentration during the terminal phase is drug elimination from the body. The distinguishing characteristic of the terminal elimination phase is that the relative proportion of drug in the plasma and peripheral volumes of distribution remains constant. During this "terminal phase" drug returns from the rapid and slow distribution volumes to the plasma, and is permanently removed from the plasma by metabolism or renal excretion.

The term "equivalent," as used herein refers to a weight of an opioid antagonist selected from naloxone and pharmaceutically acceptable salts thereof that is equimolar to a specified weight of naloxone hydrochloride. For example, 8 mg of anhydrous naloxone hydrochloride (molecular weight, 363.84) is equivalent to about 7.2 mg of naloxone freebase (molecular weight, 327.37), and to about 8.8 mg of naloxone hydrochloride dihydrate (molecular weight 399.87).

The term "filled," as used herein, refers to an association between a device and a pharmaceutical composition, for example, when a pharmaceutical composition described herein comprising a therapeutically effective amount of an opioid antagonist is present within a reservoir that forms a part of a device described herein.

The term "hydrate," as used herein, refers to an opioid antagonist described herein or a salt thereof that further includes a stoichiometric or non-stoichiometric amount of water bound by non-covalent intermolecular forces.

The term "in need of treatment" and the term "in need thereof" when referring to treatment are used interchangeably and refer to a judgment made by a caregiver (e.g. physician, nurse, nurse practitioner) that a patient will benefit from treatment.

As used herein, two embodiments are "mutually exclusive" when one is defined to be something which is different than the other. For example, an embodiment wherein the amount of naloxone hydrochloride is specified to be 4 mg is mutually exclusive with an embodiment wherein the amount of naloxone hydrochloride is specified to be 2 mg. However, an embodiment wherein the amount of naloxone hydrochloride is specified to be 4 mg is not mutually exclusive with an embodiment in which less than about 10% of said pharmaceutical composition leaves the nasal cavity via drainage into the nasopharynx or externally.

The term "naloxone," as used herein, refers to a compound of the following structure:

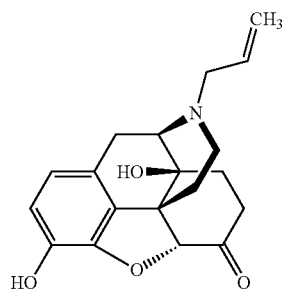

or a pharmaceutically acceptable salt, hydrate, or solvate thereof. The CAS registry number for naloxone is 465-65-6. Other names for naloxone include: 17-allyl-4,5a-epoxy-3,14-dihydroxymorphinan-6-one; (−)-17-allyl-4,5α-epoxy-3,14-dihydroxymorphinan-6-one; 4,5a-epoxy-3,14-dihydroxy-17-(2-propenyl)morphinan-6-one; and (−)-12-allyl-7,7a,8,9-tetrahydro-3,7a-dihydroxy-4aH-8,9c-iminoethanophenanthro[4,5-bcd] furan-5(6H)-one. Naloxone hydrochloride may be anhydrous (CAS Reg. No. 357-08-4) and also forms a dihydrate (CAS No. 51481-60-8). It has been sold under various brand names including Narcan®, Nalone®, Nalossone®, Naloxona®, Naloxonum®, Narcanti®, and Narcon®.

The term "nostril," as used herein, is synonymous with "naris."

The term "opioid antagonist" includes, in addition to naloxone and pharmaceutically acceptable salts thereof: naltrexone, methylnaltrexone, and nalmefene, and pharmaceutically acceptable salts thereof. In some embodiments, the opioid antagonist is naloxone hydrochloride. In some embodiments, the opioid antagonist is naloxone hydrochloride dihydrate. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the nasally administering is accomplished using a device described herein.

The term "opioid overdose," as used herein, refers to an acute medical condition induced by excessive use of one or more opioids. Symptoms of opioid overdose include including respiratory depression, central nervous system depression (which may include sedation, altered level consciousness, miotic (constricted) pupils), and cardiovascular depression (which may include hypoxemia and hypotension). Visible signs of opioid overdose or suspected opioid overdose include: unresponsiveness and/or loss of consciousness (won't respond to stimuli such as shouting, shaking, or rubbing knuckles on sternum); slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose and/or quantify, particularly by a lay person, as used herein, treatment of opioid overdose is meant to include treatment of suspected opioid overdose in opioid-intoxicated patients. Opioids that may induce overdose include, codeine, morphine, methadone, fentanyl, oxycodone HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol. In some embodiments, the opioid agonist is in a tamper-proof formulation. In some embodiments, the opioid agonist is in a tamper-resistant formulation. In some embodiments, the opioid agonist is selected from Acurox® Oxycodone DETERx®, Oxycontin®, Egalet hydrocodone, Egalet morphine, Egalet oxycodone, Exalgo®, Opana®, Opana® ER, Vicodin®, Percocet® and Remoxy®.

The term "patient," as used herein, refers to any subject (preferably human) afflicted with a condition likely to benefit from a treatment with a therapeutically effective amount of an opioid antagonist.

The terms "permeation enhancer" and "penetration enhancer," as disclosed herein, are intended to be equivalent, both referring to an agent which aids in absorption of a compound, such as through the nasal mucosa.

The term "pharmaceutical composition," as used herein, refers to a composition comprising at least one active ingredient; including but not limited to, salts, solvates and hydrates of the opioid antagonists described herein, whereby the composition is amenable to use for a specified, efficacious outcome in a mammal (for example, without limitation, a human).

The term "pre-primed," as used herein, refers to a device, such as a nasal spray which is capable of delivering a pharmaceutical composition to a patient in need thereof with the first actuation of the spray pump, i.e., without the need to prime the pump prior to dosing, such as by actuating the pump one or more times until a spray appears.

The term "receptor binding or occupancy" refers to a characterization of the kinetics between a radioactive drug and receptors or other binding sites throughout the body, and characterization of the radioactive drug binding affinity to these receptors.

The term "recovery position," as used herein, means a position of the human body in which a patient lies on his/her side, with a leg or knee out in front (e.g., to prevent rolling onto his/her stomach) and at least one hand supporting the head (e.g., to elevate the face to facilitate breathing and prevent inhalation of vomit).

The term "solvate," as used herein, refers to an opioid antagonist described herein or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "sterile filling," as used herein, refers methods of manufacturing the devices and pharmaceutical compositions described herein, such that the use of preservatives is not required. Sterile drug products may be produced using aseptic processing or terminal sterilization. Terminal sterilization usually involves filling and sealing product containers under high-quality environmental conditions. In an aseptic process, the drug product, container, and closure are first subjected to sterilization methods separately, as appropriate, and then brought together.

The term "storage-stable," as used herein, refers to a pharmaceutical composition in which at least about 95%—for example at least about 99.5%—of the active ingredient remains in an undegraded state after storage of the pharmaceutical composition at specified temperature and humidity for a specified time, for example, for 12 months at 25° C. and 60% relative humidity.

The term "supine," as used herein, refers to a patient who is lying face up.

The term "$t_{1/2}$" or "half-life," as used herein, refers to the amount of time required for half of a drug to be eliminated from the body or the time required for a drug concentration to decline by half.

The term "tonicity agent," as used herein, refers to a compound which modifies the osmolality of a formulation, for example, to render it isotonic. Tonicity agents include, dextrose, lactose, sodium chloride, calcium chloride, magnesium chloride, sorbitol, sucrose, mannitol, trehalose, raffinose, polyethylene glycol, hydroxyethyl starch, glycine and the like.

The term "tomography," as used herein, refers to a process of imaging by sections. The images may be looked at individually, as a series of two-dimensional slices or together, as a computer-generated three-dimensional representation.

The term "pharmaceutically acceptable," as used herein, refers to a component of a pharmaceutical composition that it compatible with the other ingredients of the formulation and not overly deleterious to the recipient thereof.

The term "substantially free of antimicrobial preservatives" is understood by one of ordinary skill in the art to describe a pharmaceutical composition that may comprise less than 1% w/w antimicrobial preservatives.

The term "therapeutically effective amount," as used herein, refers to the amount of active compound or pharmaceutical agent that elicits the biological or medicinal response in a tissue, system, or individual that is being sought by a researcher, healthcare provider or individual.

The term "$t_{max}$," as used herein, refers to the time from administration of the pharmaceutical compositions described herein to maximum drug plasma concentration.

The term "untrained individual" refers to an individual administering to patient an opioid antagonist using a device described herein, wherein the individual is not a healthcare professional and has received little or no training in the use of the device, such as through an overdose education and nasal naloxone distribution (OEND) program.

Where definitions conflict as between the present text and texts incorporated by reference, the definitions of the present text control.

Opioid Antagonists

Provided are drug products adapted for nasal delivery of an opioid receptor antagonist. Opioid receptor antagonists are a well recognized class of chemical agents. They have been described in detail in the scientific and patent literature. Pure opioid antagonists, such as naloxone, are agents which specifically reverse the effects of opioid agonists but have no opioid agonist activity.

Naloxone is commercially available as a hydrochloride salt. Naloxone hydrochloride (17-allyl-4,5a-epoxy-3,14-dihydroxymorphinan-6-one hydrochloride), a narcotic antagonist, is a synthetic congener of oxymorphone. In structure it differs from oxymorphone in that the methyl group on the nitrogen atom is replaced by an allyl group. Naloxone hydrochloride is an essentially pure narcotic antagonist, i.e., it does not possess the "agonistic" or morphine-like properties characteristic of other narcotic antagonists; naloxone does not produce respiratory depression, psychotomimetic effects or pupillary constriction. In the absence of narcotics or agonistic effects of other narcotic antagonists it exhibits essentially no pharmacologic activity. Naloxone has not been shown to produce tolerance or to cause physical or psychological dependence. In the presence of physical dependence on narcotics naloxone will produce withdrawal symptoms.

While the mechanism of action of naloxone is not fully understood, the preponderance of evidence suggests that naloxone antagonizes the opioid effects by competing for the same receptor sites. When naloxone hydrochloride is administered intravenously the onset of action is generally apparent within two minutes; the onset of action is only slightly less rapid when it is administered subcutaneously or intramuscularly. The duration of action is dependent upon the dose and route of administration of naloxone hydrochloride. Intramuscular administration produces a more prolonged effect than intravenous administration. The requirement for repeat doses of naloxone, however, will also be dependent upon the amount, type and route of administration of the narcotic being antagonized. Following parenteral administration naloxone hydrochloride is rapidly distributed in the body. It is metabolized in the liver, primarily by glucuronide conjugation, and excreted in urine. In one study the serum half-life in adults ranged from 30 to 81 minutes (mean 64±12 minutes). In a neonatal study the mean plasma half-life was observed to be 3.1±0.5 hours.

Provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. Also provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. In some embodiments, the therapeutically effective amount is equivalent to about 2 mg to about 24 mg of naloxone hydrochloride. In some embodiments, the therapeutically effective amount is equivalent to about 2 mg to about 12 mg of naloxone hydrochloride. In some embodiments, the therapeutically effective amount is equivalent to about 3 mg to about 18 mg of naloxone hydrochloride. In some embodiments, the therapeutically effective amount is equivalent to about 4 mg to about 10 mg of naloxone hydrochloride. In some embodiments, the therapeutically effective amount is equivalent to about 5 mg to about 11 mg of naloxone hydrochloride. In some embodiments, the therapeutically effective amount is equivalent to about 6 mg to about 10 mg of naloxone hydrochloride. In some embodiments, the therapeutically effective amount is equivalent to about 4 mg to about 8 mg of naloxone hydrochloride. In some embodiments, the therapeutically effective amount is equivalent to about 7 mg to about 9 mg of naloxone hydrochloride. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the therapeutically effective amount is equivalent to about 5 mg of naloxone hydrochloride. In some embodiments, the therapeutically effective amount is equivalent to about 6 mg of naloxone hydrochloride. In some embodiments, the therapeutically effective amount is equivalent to about 7 mg of naloxone hydrochloride. In some embodiments, the therapeutically effective amount is equivalent to about 8 mg of naloxone hydrochloride. In some embodiments, the therapeutically effective amount is equivalent to about 9 mg of naloxone hydrochloride. In some embodiments, the therapeutically effective amount is equivalent to about 10 mg of naloxone hydrochloride. In some embodiments, the therapeutically effective amount is equivalent to about 11 mg of naloxone hydrochloride. In some embodiments, the therapeutically effective amount is equivalent to about 12 mg of naloxone hydrochloride. In some embodiments, the opioid antagonist is the only pharmaceutically active compound in pharmaceutical composition. In some embodiments, the opioid antagonist is naloxone hydrochloride. In some embodiments, the opioid antagonist is anhydrous naloxone hydrochloride. In some embodiments, the opioid antagonist is naloxone hydrochloride dihydrate.

While many of the embodiments of the pharmaceutical compositions described herein will be described and exemplified with naloxone, other opioid antagonists can be adapted for nasal delivery based on the teachings of the specification. In fact, it should be readily apparent to one of ordinary skill in the art from the teachings herein that the devices and pharmaceutical compositions described herein may be suitable for other opioid antagonists. The opioid receptor antagonists described herein include μ-opioid antagonists and δ-opioid receptor antagonists. Examples of useful opioid receptor antagonists include naloxone, naltrexone, methylnaltrexone, and nalmefene. Other useful opioid receptor antagonists are known (see, e.g., Kreek et al., U.S. Pat. No. 4,987,136).

Also provided are devices adapted for nasal delivery of a pharmaceutical composition to a patient, comprising a therapeutically effective amount of an opioid antagonist, wherein the device is pre-primed, and wherein the therapeutically effective amount is about 4 mg to about 12 mg. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the opioid antagonist is selected from naltrexone, methylnaltrexone, and nalmefene, and pharmaceutically acceptable salts thereof. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the opioid antagonist is the only pharmaceutically active compound in pharmaceutical composition.

Nasal Drug Delivery Devices and Kits

Also provided are nasal drug delivery devices comprising a pharmaceutical composition described herein. Nasal delivery is considered an attractive route for needle-free, systemic drug delivery, especially when rapid absorption and effect are desired. In addition, nasal delivery may help address issues related to poor bioavailability, slow absorption, drug degradation, and adverse events (AEs) in the gastrointestinal tract and avoids the first-pass metabolism in the liver.

Liquid nasal formulations are mainly aqueous solutions, but suspensions and emulsions can also be delivered. In traditional spray pump systems, antimicrobial preservatives are typically required to maintain microbiological stability in liquid formulations.

Some emergency medical services (EMS) programs have developed a system using existing technologies of an approved drug and an existing medical device to administer naloxone intranasally, albeit in a non-FDA approved manner. This has been accomplished by using the injectable formulation (1 mg/mL) and administering 1 mL per nostril via a marketed nasal atomizer/nebulizer device. The system combines an FDA-approved naloxone injection product (with a Luer fitted tip, no needles) with a marketed, medical device called the Mucosal Atomization Device (MAD™ Nasal, Wolfe Tory Medical, Inc.). The EMS programs recognize limitations of this system, one limitation being that it is not assembled and ready-to-use. Although this administration mode appears to be effective in reversing narcosis, the formulation is not concentrated for retention in the nasal cavity. The human nasal cavity has a volume of ~200-250 μL. The 1 mL delivery volume per nostril is larger than that generally utilized for intranasal drug administration. Therefore, there is loss of drug from the nasal cavity, due either to drainage into the nasopharynx or externally from the nasal cavity. The devices described herein are improved ready-to-use products specifically optimized, concentrated, and formulated for nasal delivery.

Metered spray pumps have dominated the nasal drug delivery market since they were introduced. The pumps typically deliver 100 μL (25-200 μL) per spray, and they offer high reproducibility of the emitted dose and plume geometry in in vitro tests. The particle size and plume geometry can vary within certain limits and depend on the properties of the pump, the formulation, the orifice of the actuator, and the force applied. Traditional spray pumps replace the emitted liquid with air, and preservatives are therefore required to prevent contamination. However, driven by the studies suggesting possible negative effects of preservatives, pump manufacturers have developed different spray systems that avoid the need for preservatives. These systems use a collapsible bag, a movable piston, or a compressed gas to compensate for the emitted liquid volume (www.aptar.com and www.rexam.-com). The solutions with a collapsible bag and a movable piston compensating for the emitted liquid volume offer the additional advantage that they can be emitted upside down, without the risk of sucking air into the dip tube and compromising the subsequent spray. This may be useful for some products where the patients are bedridden and where a head down application is recommended. Another method used for avoiding preservatives is that the air that replaces the emitted liquid is filtered through an aseptic air filter. In addition, some systems have a ball valve at the tip to prevent contamination of the liquid inside the applicator tip (www.aptar.com). More recently, pumps have been designed with side-actuation and introduced for delivery of fluticasone furoate for the indication of seasonal and perennial allergic rhinitis. The pump was designed with a shorter tip to avoid contact with the sensitive mucosal surfaces. New designs to reduce the need for priming and re-priming, and pumps incorporating pressure point features to improve the dose reproducibility and dose counters and lock-out mechanisms for enhanced dose control and safety are available (www.rexam.com and www.aptar.com).

Metered-dose spray pumps require priming and some degree of overfill to maintain dose conformity for the labeled number of doses. They are well suited for drugs to be administered daily over a prolonged duration, but due to the priming procedure and limited control of dosing, they are less suited for drugs with a narrow therapeutic window. For expensive drugs and vaccines intended for single administration or sporadic use and where tight control of the dose and formulation is of particular importance, single-dose or bi-dose spray devices are preferred (www.aptar.com). A simple variant of a single-dose spray device (MAD™) is offered by LMA (LMA, Salt Lake City, Utah, USA; www.l-mana.com). A nosepiece with a spray tip is fitted to a standard syringe. The liquid drug to be delivered is first drawn into the syringe and then the spray tip is fitted onto the syringe. This device has been used in academic studies to deliver, for example, a topical steroid in patients with chronic rhinosinusitis and in a vaccine study. A pre-filled device based on the same principle for one or two doses (Accuspray™, Becton Dickinson Technologies, Research Triangle Park, N.C., USA; www.bdpharma.com) is used to deliver the influenza vaccine FluMist (www.flumist.com), approved for both adults and children in the US market. A similar device for two doses was marketed by a Swiss company for delivery of another influenza vaccine a decade ago. The single- and bi-dose devices mentioned above consist of a reservoir, a piston, and a swirl chamber (see, e.g., the UDS UnitDose and BDS BiDose devices from Aptar, formerly Pfeiffer). The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like Imitrex (www.gsk.com) and Zomig (www.az.com; Pfeiffer/Aptar single-dose device) and the marketed influenza vaccine Flu-Mist (www.flumist.com; Becton Dickinson single-dose spray device) are delivered with this type of device.

With sterile filling, the use of preservatives is not required, but overfill is required resulting in a waste fraction similar to the metered-dose, multi-dose sprays. To emit 100 μL, a volume of 125 μL is filled in the device (Pfeiffer/Aptar single-dose device) used for the intranasal migraine medications Imitrex (sumatriptan) and Zomig (zolmitriptan) and about half of that for a bi-dose design. Sterile drug products may be produced using aseptic processing or terminal sterilization. Terminal sterilization usually involves filling and sealing product containers under high-quality environmental conditions. Products are filled and sealed in this type of environment to minimize the microbial and particulate content of the in-process product and to help ensure that the subsequent sterilization process is successful. In most cases, the product, container, and closure have low bioburden, but they are not sterile. The product in its final container is then subjected to a sterilization process such as heat or irradiation. In an aseptic process, the drug product, container, and closure are first subjected to sterilization methods separately, as appropriate, and then brought together. Because there is no process to sterilize the product in its final container, it is critical that containers be filled and sealed in an extremely high-quality environment. Aseptic processing involves more variables than terminal sterilization. Before aseptic assembly into a final product, the individual parts of the final product are generally subjected to various sterilization processes. For example, glass containers are subjected to dry heat; rubber closures are subjected to moist heat; and liquid dosage forms are subjected to filtration. Each of these manufacturing processes requires validation and control.

Accordingly, provided herein are devices adapted for nasal delivery of a pharmaceutical composition to a patient, comprising a therapeutically effective amount of an opioid antagonist selected from naloxone and pharmaceutically acceptable salts thereof, wherein said device is pre-primed, and wherein said therapeutically effective amount, is equivalent to about 2 mg to about 12 mg of naloxone hydrochloride.

In some embodiments, said opioid antagonist is naloxone hydrochloride. In some embodiments, said opioid antagonist is naloxone hydrochloride dihydrate.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual. Also disclosed herein are methods of improving accuracy of dose delivery by an untrained individual, the method comprising administering a dose of opioid antagonist from a device as described herein.

In some embodiments, said therapeutically effective amount is equivalent to about 4 mg to about 10 mg of naloxone hydrochloride. In some embodiments, said therapeutically effective amount is equivalent to an amount chosen from about 2 mg naloxone hydrochloride, about 4 mg naloxone hydrochloride, and about 8 mg naloxone hydrochloride. In some embodiments, said therapeutically effective amount is equivalent to about 2 mg of naloxone hydrochloride. In some embodiments, said therapeutically effective amount is equivalent to about 4 mg of naloxone hydrochloride. In some embodiments, said therapeutically effective amount is equivalent to about 8 mg of naloxone hydrochloride. In some embodiments, the therapeutically effective amount is equivalent to about 3.4 mg of naloxone hydrochloride.

In some embodiments, said therapeutically effective amount is about 2.2 mg to about 13.2 mg of naloxone hydrochloride dihydrate. In some embodiments, said therapeutically effective amount is about 4.4 mg to about 11 mg of naloxone hydrochloride dihydrate. In some embodiments, said therapeutically effective amount is an amount chosen from about 2.2 mg naloxone hydrochloride dihydrate, about 4.4 mg of naloxone hydrochloride dihydrate, and about 8.8 mg naloxone hydrochloride dihydrate. In some embodiments, said therapeutically effective amount is about 2.2 mg of naloxone hydrochloride dihydrate. In some embodiments, said therapeutically effective amount is about 4.4 mg of naloxone hydrochloride dihydrate. In some embodiments, said therapeutically effective amount is about 8.8 mg of naloxone hydrochloride dihydrate.

In some embodiments, said opioid antagonist is the only pharmaceutically active compound in said pharmaceutical composition.

In some embodiments, said pharmaceutical composition comprises a solution of naloxone hydrochloride, or a hydrate thereof.

In some embodiments, the volume of said pharmaceutical composition in said reservoir is not more than about 140 µL.

In some embodiments, about 100 µL of said pharmaceutical composition in said reservoir is delivered to said patient in one actuation.

In some embodiments, said pharmaceutical composition further comprises one or more excipients selected from water and NaCl.

In some embodiments, said pharmaceutical composition is substantially free of antimicrobial preservatives.

In some embodiments, said pharmaceutical composition further comprises a preservative, permeation/penetration enhancer and/or a cationic surfactant; an isotonicity agent; a stabilizing agent; and an amount of acid sufficient to achieve a pH of 3.5-5.5. In some embodiments, the preservative, permeation/penetration enhancer and/or a cationic surfactant is selected from benzalkonium chloride, cyclodextrins, fusidic acid derivatives, phosphatidylcholines, microspheres and liposomes, and bile salts. In a particular embodiment, the preservative, permeation/penetration enhancer and/or a cationic surfactant is benzalkonium chloride.

In some embodiments, said pharmaceutical composition further comprises one or more excipients selected from water, NaCl, benzalkonium chloride, sodium edetate, disodium edetate, and hydrochloric acid.

In some embodiments, said pharmaceutical composition further comprises water, NaCl, benzalkonium chloride, disodium edetate, and hydrochloric acid.

In certain embodiments, said pharmaceutical composition comprises benzalkonium chloride. The can function as a preservative (even in low amounts), a permeation/penetration enhancer, and/or a cationic surfactant (typically at a higher amount for these latter two). Benzalkonium chloride is represented by the following structure:

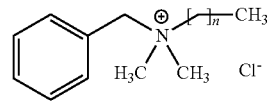

in which n is an integer, and a mixture of more than one thereof can be used. In certain embodiments, n is 8, 10, 12, 14, 16, or 18, and in certain embodiments, n is 10, 12, or 14. In certain embodiments, said pharmaceutical composition comprises about 0.005% to about 1% benzalkonium chloride. In certain embodiments, said pharmaceutical composition comprises about 0.01% to about 1% benzalkonium chloride. In certain embodiments, said pharmaceutical composition comprises about 0.005% to about 0.015% benzalkonium chloride.

In its capacity as a surfactant, benzalkonium chloride can affect the surface tension of droplets from a delivered nasal spray plume, producing spherical or substantially spherical particles having a narrow droplet size distribution (DSD), as well as the viscosity of a liquid formulation.

The droplet size distribution of a nasal spray is a critical parameter, since it significantly influences the in vivo deposition of the drug in the nasal cavity. The droplet size is influenced by the actuation parameters of the device and the formulation. The prevalent median droplet size should be between about 30 and about 100 µm. If the droplets are too large (>about 120 µm), deposition takes place mainly in the anterior parts of the nose, and if the droplets are too small (<about 10 µm), they can possibly be inhaled and reach the lungs, which should be avoided because of safety reasons (benzalkonium chloride significantly increases mucin secretion while significantly attenuating mucoiliary transport rate and is toxic to 16HBE14o-cells.)

Spray characterization (e.g., plume geometry, spray pattern, pump delivery, droplet size distribution, DSD) of the delivered plume subsequent to spraying may be measured under specified experimental and instrumental conditions by appropriate and validated and/or calibrated analytical procedures known in the art. These include photography, laser diffraction, and impaction systems (cascade impaction, next generation impaction (NGI), etc.). Droplet size distribution can be controlled in terms of ranges for the D10, D50, D90, span [(D90−D10)/D50], and percentage of droplets less than 10 mm. In certain embodiments, the formulation will have a narrow DSD. In certain embodiments, the formulation will have a Dv(50) of 30-70 μm and a Dv(90)<100 μm. The particle diameter "(D)" designations refer to the representative diameter where 10% (D10), 50% (D50) and 90% (D90) of the total volume of the liquid sprayed is made up of droplets with diameters smaller than or equal to the stated value.

In certain embodiments, the percent of droplets less than 10 μm will be less than 10%. In certain embodiments, the percent of droplets less than 10 μm will be less than 5%. In certain embodiments, the percent of droplets less than 10 μm will be less than 2%. In certain embodiments, the percent of droplets less than 10 μm will be less than 1%. In certain embodiments, the spray—also described at times as a "mist"—having these droplet size characteristics can comprise a preservative composed of one or more compounds of formula (I)

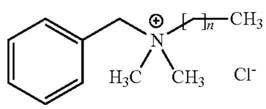

(I)

wherein n is an integer selected from the group consisting of 8, 10, 12, 14, 16, and 18. For example, n can be an integer selected from the group consisting of 10, 12, and 14.

In certain embodiments, the formulation when dispensed by actuation from the device will produce a uniform circular spray plume with an ovality ratio close to 1. In certain embodiments, the ovality ratio is between 0.7 and 2.5. In certain embodiments, the ovality ratio is less than 2.0. In certain embodiments, the ovality ratio is less than 1.5. In certain embodiments, the ovality ratio is less than 1.3. In certain embodiments, the ovality ratio is less than 1.2. In certain embodiments, the ovality ratio is less than 1.1. In certain embodiments, the ovality ratio is about 1.0.

When benzalkonium chloride is provided in a formulation in an amount effective to function as a permeation/penetration enhancer and/or a cationic surfactant, the spray pattern, droplet size and DSD are expected to provide improved pharmacokinetic outcomes such as $C_{max}$, $t_{max}$, and linear dose proportionality compared to both intramuscular formulations and intranasal formulations that do not contain benzalkonium chloride in an amount effective to function as a permeation/penetration enhancer and/or a cationic surfactant. In certain embodiments, a formulation as disclosed herein comprising benzalkonium chloride in an amount effective to function as a permeation/penetration enhancer and/or a cationic surfactant will yield a formulation that is at least 35% bioavailable, at least 40% bioavailable, at least 45% bioavailable, at least 50% bioavailable, or at least 55% bioavailable.

Accordingly, provided herein is a drug product comprising a combination of a therapeutically effective amount of an opioid agonist and a therapeutically effective amount of naloxone hydrochloride or a hydrate thereof, wherein said naloxone hydrochloride or hydrate thereof is contained in a single-use, pre-primed device adapted for nasal delivery of a pharmaceutical composition to a patient by one actuation of said device into one nostril of said patient, and wherein the single-use, pre-primed device comprises a reservoir containing a pharmaceutical composition which is an aqueous solution of about 100 μL comprising:

- naloxone hydrochloride or a hydrate thereof;
- benzalkonium chloride in an amount effective to function as a permeation/penetration enhancer and/or a cationic surfactant;
- an isotonicity agent;
- a stabilizing agent; and
- an amount of acid sufficient to achieve a pH of 3.5-5.5.

In certain embodiments, the single-use, pre-primed device adapted for nasal delivery of a pharmaceutical composition to a patient comprises between about 2 mg and about 12 mg of the naloxone hydrochloride or a hydrate thereof.

In certain embodiments, the single-use, pre-primed device adapted for nasal delivery of a pharmaceutical composition to a patient comprises about 2 mg, about 4 mg, or about 8 mg of the naloxone hydrochloride or a hydrate thereof.

In certain embodiments, the aqueous solution comprises:

- between about 2 mg and about 12 mg of the naloxone hydrochloride or a hydrate thereof;
- between about 0.001 mg and about 0.1 mg (i.e., about 0.01% w/v to about 1% w/v) benzalkonium chloride;
- between about 0.2 mg and about 1.2 mg of an isotonicity agent;
- between about 0.1 mg and about 0.5 mg of a stabilizing agent; and
- an amount of acid sufficient to achieve a pH of 3.5-5.5.

In certain embodiments,

- the isotonicity agent is NaCl;
- the stabilizing agent is disodium edetate; and
- the acid is hydrochloric acid.

In certain embodiments, the aqueous solution comprises:

- about 4.4 mg naloxone hydrochloride dihydrate;
- about 0.74 mg NaCl;
- between about 0.001 mg and about 0.1 mg (i.e., about 0.01% w/v to about 1% w/v) benzalkonium chloride;
- about 0.2 mg disodium edetate; and
- an amount of hydrochloric acid sufficient to achieve a pH of 3.5-5.5.

Also provided herein is a drug product comprising a combination of a therapeutically effective amount of an opioid agonist and a therapeutically effective amount of naloxone hydrochloride or a hydrate thereof, wherein said naloxone hydrochloride or hydrate thereof is contained in a pre-primed, bi-dose device adapted for nasal delivery of a pharmaceutical composition to a patient, wherein a first volume of said pharmaceutical composition is present in a first reservoir, and a second volume of said pharmaceutical composition is present in a second reservoir, and wherein said therapeutically effective amount of said opioid antagonist is delivered essentially by a first actuation of said drug delivery device from said first reservoir into a nostril of said patient and a second actuation of said drug delivery device from said second reservoir into a nostril of said patient; each reservoir comprising a pharmaceutical composition which is an aqueous solution of about 100 μL comprising:

- an isotonicity agent;
- benzalkonium chloride in an amount effective to function as a permeation/penetration enhancer and/or a cationic surfactant;
- a stabilizing agent; and
- an amount of acid sufficient to achieve a pH of 3.5-5.5.

In certain embodiments, each reservoir of the pre-primed, bi-dose device adapted for nasal delivery of a pharmaceutical composition to a patient comprises between about 2 mg and about 12 mg of the naloxone hydrochloride or a hydrate thereof.

In certain embodiments, each reservoir of the pre-primed, bi-dose device adapted for nasal delivery of a pharmaceutical composition to a patient comprises about 2 mg, about 4 mg, or about 8 mg of the naloxone hydrochloride or a hydrate thereof.

In certain embodiments, the aqueous solution comprises:
between about 2 mg and about 12 mg of the naloxone hydrochloride or a hydrate thereof;
between about 0.001 mg and about 0.1 mg (i.e., about 0.01% w/v to about 1% w/v) benzalkonium chloride;
between about 0.2 mg and about 1.2 mg of an isotonicity agent;
between about 0.1 mg and about 0.5 mg of a stabilizing agent; and
an amount of acid sufficient to achieve a pH or 3.5-5.5.

In certain embodiments,
the isotonicity agent is NaCl;
the stabilizing agent is disodium edetate; and
the acid is hydrochloric acid.

In certain embodiments, the aqueous solution comprises:
about 2.2 mg or about 4.4 mg naloxone hydrochloride dihydrate;
between about 0.001 mg and about 0.1 mg (i.e., about 0.01% w/v to about 1% w/v) benzalkonium chloride;
about 0.2 mg disodium edetate; and
an amount of hydrochloric acid sufficient to achieve a pH of 3.5-5.5.

In certain embodiments, each reservoir comprises about 2.2 mg of the naloxone hydrochloride dihydrate.

In certain embodiments, each reservoir comprises about 4.4 mg of the naloxone hydrochloride dihydrate.

Also provided herein is a method of lowering opioid overdose risk in an individual at risk for opioid overdose, comprising providing to the individual at risk for opioid overdose a combination of a therapeutically effective amount of an opioid agonist and a therapeutically effective amount of naloxone hydrochloride or a hydrate thereof, wherein said naloxone hydrochloride or hydrate thereof is contained in a single-use, pre-primed device adapted for nasal delivery of a pharmaceutical composition to a patient by one actuation of said device into one nostril of said patient, and wherein the single-use, pre-primed device comprises a reservoir containing a pharmaceutical composition which is an aqueous solution of about 100 µL comprising:
naloxone hydrochloride or a hydrate thereof;
an isotonicity agent;
benzalkonium chloride in an amount effective to function as a permeation/penetration enhancer and/or a cationic surfactant;
a stabilizing agent; and
an amount of acid sufficient to achieve a pH of 3.5-5.5.

In certain embodiments, the single-use, pre-primed device adapted for nasal delivery of a pharmaceutical composition to a patient comprises between about 2 mg and about 12 mg of the naloxone hydrochloride or a hydrate thereof.

In certain embodiments, the single-use, pre-primed device adapted for nasal delivery of a pharmaceutical composition to a patient comprises about 2 mg, about 4 mg, or about 8 mg of the naloxone hydrochloride or a hydrate thereof.

In certain embodiments, the aqueous solution comprises:
between about 2 mg and about 12 mg of the naloxone hydrochloride or a hydrate thereof;
between about 0.001 mg and about 0.1 mg (i.e., about 0.01% w/v to about 1% w/v) benzalkonium chloride;
between about 0.2 mg and about 1.2 mg of an isotonicity agent;
between about 0.1 mg and about 0.5 mg of a stabilizing agent; and
an amount of acid sufficient to achieve a pH of 3.5-5.5.

In certain embodiments,
the isotonicity agent is NaCl;
the stabilizing agent is disodium edetate; and
the acid is hydrochloric acid.

In certain embodiments, the aqueous solution comprises:
about 4.4 mg naloxone hydrochloride dihydrate;
about 0.74 mg NaCl;
between about 0.001 mg and about 0.1 mg (i.e., about 0.01% w/v to about 1% w/v) benzalkonium chloride;
about 0.2 mg disodium edetate; and
an amount of hydrochloric acid sufficient to achieve a pH of 3.5-5.5.

Also provided herein is a method of lowering opioid overdose risk in an individual at risk for opioid overdose, comprising providing to the individual at risk for opioid overdose a combination of a therapeutically effective amount of an opioid agonist and a therapeutically effective amount of naloxone hydrochloride or a hydrate thereof, wherein said naloxone hydrochloride or hydrate thereof is contained in a pre-primed, bi-dose device adapted for nasal delivery of a pharmaceutical composition to a patient, wherein a first volume of said pharmaceutical composition is present in a first reservoir, and a second volume of said pharmaceutical composition is present in a second reservoir, and wherein said therapeutically effective amount of said opioid antagonist is delivered essentially by a first actuation of said drug delivery device from said first reservoir into a nostril of said patient and a second actuation of said drug delivery device from said second reservoir into a nostril of said patient; each reservoir comprising a pharmaceutical composition which is an aqueous solution of about 100 µL comprising:
naloxone hydrochloride or a hydrate thereof;
between about 0.2 mg and about 1.2 mg of an isotonicity agent;
benzalkonium chloride in an amount effective to function as a permeation/penetration enhancer and/or a cationic surfactant;
a stabilizing agent; and
an amount of acid sufficient to achieve a pH of 3.5-5.5.

In certain embodiments, the single-use, pre-primed device adapted for nasal delivery of a pharmaceutical composition to a patient comprises between about 2 mg and about 12 mg of the naloxone hydrochloride or a hydrate thereof.

In certain embodiments, each reservoir of the single-use, pre-primed device adapted for nasal delivery of a pharmaceutical composition to a patient comprises about 2 mg, about 4 mg, or about 8 mg of the naloxone hydrochloride or a hydrate thereof.

In certain embodiments, each reservoir comprises about 2 mg of the naloxone hydrochloride or a hydrate thereof.

In certain embodiments, each reservoir comprises about 4 mg of the naloxone hydrochloride or a hydrate thereof.

In certain embodiments, the aqueous solution comprises:
between about 2 mg and about 12 mg of the naloxone hydrochloride or a hydrate thereof;
between about 0.001 mg and about 0.1 mg (i.e., about 0.01% w/v to about 1% w/v) benzalkonium chloride;
between about 0.2 mg and about 1.2 mg of an isotonicity agent;
between about 0.1 mg and about 0.5 mg of a stabilizing agent; and
an amount of acid sufficient to achieve a pH of 3.5-5.5.

In certain embodiments,
the isotonicity agent is NaCl;
the stabilizing agent is disodium edetate; and
the acid is hydrochloric acid.

In certain embodiments, each reservoir comprises:
about 2.2 mg or about 4.4 mg naloxone hydrochloride dihydrate;
about 0.74 mg NaCl;
between about 0.001 mg and about 0.1 mg (i.e., about 0.01% w/v to about 1% w/v) benzalkonium chloride; and
about 0.2 mg disodium edetate.

In some embodiments, said pharmaceutical composition further comprises one or more excipients selected from water, NaCl, benzalkonium chloride, sodium edetate, disodium edetate, and hydrochloric acid.

In some embodiments, said pharmaceutical composition further comprises water, NaCl, benzalkonium chloride, disodium edetate, and hydrochloric acid.

In some embodiments, said pharmaceutical composition further comprises:
an isotonicity agent;
a preservative;
a stabilizing agent;
an amount of acid sufficient to achieve a pH of 3.5-5.5; and
an amount of water sufficient to achieve a final volume of about 100 µL.

In some embodiments, said pharmaceutical composition comprises:
between about 0.2 mg and about 1.2 mg of an isotonicity agent;
between about 0.005 mg and about 0.015 mg of a compound which is a preservative, cationic surfactant, and/or permeation enhancer;
between about 0.1 mg and about 0.5 mg of a stabilizing agent;
an amount of an acid sufficient to achieve a pH of 3.5-5.5; and
an amount of water sufficient to achieve a final volume of about 100 µL.

In some embodiments,
the isotonicity agent is NaCl;
the compound which is a preservative, cationic surfactant, and/or permeation enhancer is benzalkonium chloride;
the stabilizing agent is disodium edetate; and
the acid is hydrochloric acid.

In some embodiments, said pharmaceutical composition comprises:
about 0.74 mg NaCl;
about 0.01 mg benzalkonium chloride;
about 0.2 mg disodium edetate;
an amount of hydrochloric acid sufficient to achieve a pH of 3.5-5.5; and
an amount of water sufficient to achieve a final volume of about 100 µL.

In some embodiments, said device is filled with said pharmaceutical composition using sterile filling.

In some embodiments, said pharmaceutical composition is storage-stable for about twelve months at about 25° C. and about 60% relative humidity.

In some embodiments, said device is a single-dose device, wherein said pharmaceutical composition is present in one reservoir, and wherein said therapeutically effective amount of said opioid antagonist is delivered essentially by one actuation of said device into one nostril of said patient.

In some embodiments, about 100 µL of said pharmaceutical composition is delivered by said actuation.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $t_{max}$ of less than 30 minutes. In some embodiments, the plasma concentration versus time curve of said opioid antagonist in said patient has a $t_{max}$ of less than 25 minutes. In some embodiments, the plasma concentration versus time curve of the opioid antagonist in the patient has a $t_{max}$ of less than 20 minutes. In some embodiments, the plasma concentration versus time curve of said opioid antagonist in said patient has a $t_{max}$ of about 20 minutes. In some embodiments, the plasma concentration versus time curve of the opioid antagonist in the patient has a $t_{max}$ of less than 19 minutes. In some embodiments, the plasma concentration versus time curve of the opioid antagonist in the patient has a $t_{max}$ of about 18.5 minutes.

In some embodiments, delivery of said therapeutically effective amount to said patient, provides occupancy at $t_{max}$ of said opioid antagonist at the opioid receptors in the respiratory control center of said patient of greater than about 90%. In some embodiments, delivery of said therapeutically effective amount to said patient, provides occupancy at $t_{max}$ of said opioid antagonist at the opioid receptors in the respiratory control center of said patient of greater than about 95%. In some embodiments, delivery of said therapeutically effective amount to said patient, provides occupancy at $t_{max}$ of said opioid antagonist at the opioid receptors in the respiratory control center of said patient of greater than about 99%.

In some embodiments, said patient is free from respiratory depression for at least about 1 hour following treatment comprising delivery of said therapeutically effective amount of said opioid antagonist. In some embodiments, said patient is free from respiratory depression for at least about 2 hours following treatment comprising delivery of said therapeutically effective amount of said opioid antagonist. In some embodiments, said patient is free from respiratory depression for at least about 4 hours following treatment comprising delivery of said therapeutically effective amount of said opioid antagonist. In some embodiments, said patient is free from respiratory depression for at least about 6 hours following treatment comprising delivery of said therapeutically effective amount of said opioid antagonist.

In some embodiments, said device is a bi-dose device, wherein a first volume of said pharmaceutical composition is present in a first reservoir and a second volume of said pharmaceutical composition is present in a second reservoir, and wherein said therapeutically effective amount is delivered essentially by a first actuation of said device into a first nostril of said patient and a second actuation of said device into a second nostril of said patient.

In some embodiments, said first volume and said second volume combined is equal to not more than about 380 μL.

In some embodiments, about 100 μL of said first volume of said pharmaceutical composition is delivered by said first actuation.

In some embodiments, about 100 μL of said second volume of said pharmaceutical composition is delivered by said second actuation.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $t_{max}$ of less than 30 minutes. In some embodiments, the plasma concentration versus time curve of said opioid antagonist in said patient has a $t_{max}$ of less than 25 minutes. In some embodiments, the plasma concentration versus time curve of said opioid antagonist in said patient has a $t_{max}$ of about 20 minutes. In some embodiments, the plasma concentration versus time curve of the opioid antagonist in the patient has a $t_{max}$ of less than 19 minutes. In some embodiments, the plasma concentration versus time curve of the opioid antagonist in the patient has a $t_{max}$ of about 18.5 minutes.

In some embodiments, delivery of said therapeutically effective amount to said patient, provides occupancy at $t_{max}$ of said opioid antagonist at the opioid receptors in the respiratory control center of said patient of greater than about 90%. In some embodiments, delivery of said therapeutically effective amount to said patient, provides occupancy at $t_{max}$ of said opioid antagonist at the opioid receptors in the respiratory control center of said patient of greater than about 95%. In some embodiments, delivery of said therapeutically effective amount to said patient, provides occupancy at $t_{max}$ of said opioid antagonist at the opioid receptors in the respiratory control center of said patient of greater than about 99%.

In some embodiments, said patient is free from respiratory depression for at least about 1 hour following treatment comprising delivery of said therapeutically effective amount of said opioid antagonist. In some embodiments, said patient is free from respiratory depression for at least about 2 hours following treatment comprising delivery of said therapeutically effective amount of said opioid antagonist. In some embodiments, said patient is free from respiratory depression for at least about 4 hours following treatment comprising delivery of said therapeutically effective amount of said opioid antagonist. In some embodiments, said patient is free from respiratory depression for at least about 6 hours following treatment comprising delivery of said therapeutically effective amount of said opioid antagonist.

Also provided herein is a single-use, pre-primed device adapted for nasal delivery of a pharmaceutical composition to a patient by one actuation of said device into one nostril of said patient, having a single reservoir comprising about 100 μL of a pharmaceutical composition which is an aqueous solution comprising:

about 2 mg or about 4 mg naloxone hydrochloride or a hydrate thereof;

between about 0.2 mg and about 1.2 mg of an isotonicity agent;

between about 0.005 mg and about 0.015 mg of a compound which is a preservative, cationic surfactant, and/or permeation enhancer;

between about 0.1 mg and about 0.5 mg of a stabilizing agent; and an amount of acid sufficient to achieve a pH of 3.5-5.5.

In some embodiments, the device comprises about 4 mg naloxone hydrochloride or a hydrate thereof. In some embodiments, the device comprises about 2 mg naloxone hydrochloride or a hydrate thereof. In some embodiments, the device comprises about 4.4 mg naloxone hydrochloride dihydrate. In some embodiments, the device comprises about 2.2 mg naloxone hydrochloride dihydrate.

In some embodiments,
the isotonicity agent is NaCl;
the compound which is a preservative cationic surfactant and/or permeation enhancer is benzalkonium chloride;
the stabilizing agent is disodium edetate; and
the acid is hydrochloric acid.

In some embodiments, the device comprises:
about 2.2 mg or about 4.4 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH of 3.5-5.5.

In some embodiments, the device comprises about 4.4 mg naloxone hydrochloride dihydrate. In some embodiments, the device comprises about 2.2 mg naloxone hydrochloride dihydrate.

In some embodiments, upon nasal delivery of said pharmaceutical composition to said patient, less than about 10% of said pharmaceutical composition leaves the nasal cavity via drainage into the nasopharynx or externally.

In some embodiments, the plasma concentration versus time curve of said naloxone hydrochloride in said patient has a $t_{max}$ of between about 20 and about 30 minutes.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $t_{max}$ of less than 30 minutes. In some embodiments, the plasma concentration versus time curve of said opioid antagonist in said patient has a $t_{max}$ of less than 25 minutes. In some embodiments, the plasma concentration versus time curve of said opioid antagonist in said patient has a $t_{max}$ of about 20 minutes. In some embodiments, the plasma concentration versus time curve of the opioid antagonist in the patient has a $t_{max}$ of less than 19 minutes. In some embodiments, the plasma concentration versus time curve of the opioid antagonist in the patient has a $t_{max}$ of about 18.5 minutes.

In some embodiments, delivery of said therapeutically effective amount to said patient, provides occupancy at $t_{max}$ of said opioid antagonist at the opioid receptors in the respiratory control center of said patient of greater than about 90%. In some embodiments, delivery of said therapeutically effective amount to said patient, provides occupancy at $t_{max}$ of said opioid antagonist at the opioid receptors in the respiratory control center of said patient of greater than about 95%. In some embodiments, delivery of said therapeutically effective amount to said patient, provides occupancy at $t_{max}$ of said opioid antagonist at the opioid receptors in the respiratory control center of said patient of greater than about 99%.

In some embodiments, said patient is free from respiratory depression for at least about 1 hour following treatment comprising delivery of said therapeutically effective amount of said opioid antagonist. In some embodiments, said patient is free from respiratory depression for at least about 2 hours following treatment comprising delivery of said therapeutically effective amount of said opioid antagonist. In some embodiments, said patient is free from respiratory depression for at least about 4 hours following treatment comprising delivery of said therapeutically effective amount of said opioid antagonist. In some embodiments, said patient is free from respiratory depression for at least about 6 hours following treatment comprising delivery of said therapeutically effective amount of said opioid antagonist.

In some embodiments, said device is filled with said pharmaceutical composition using sterile filling.

In some embodiments, said pharmaceutical composition is storage-stable for about twelve, about fifteen, or even about eighteen months at about 25° C. and about 60% relative humidity.

In some embodiments, said opioid antagonist is the only pharmaceutically active compound in said pharmaceutical composition.

Also provided are devices as recited in any of the preceding embodiments for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension.

Also provided are devices as recited in any of the preceding embodiments for use in the reversal of respiratory depression induced by opioids.

In some embodiments, said respiratory depression is caused by the illicit use of opioids or by an accidental misuse of opioids during medical opioid therapy.

Also provided are devices as recited in any of the preceding embodiments for use in the complete or partial reversal of narcotic depression, including respiratory depression, induced by opioids selected from: natural and synthetic narcotics, propoxyphene, methadone, nalbuphine, pentazocine and butorphanol.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

Also provided are kits comprising a device described herein and written instructions for using the device. Also provided are kits comprising a device described herein and an opioid agonist. In some embodiments the kit further comprises written instructions. In some embodiments, the opioid agonist is selected from codeine, morphine, methadone, fentanyl, oxycodone HCl, hydrocodone bitartrate, hydromorphone, oxymorphone, meperidine, propoxyphene, opium, heroin, and certain narcotic-antagonist analgesics, such as, nalbuphine, pentazocine and butorphanol. In some embodiments, the opioid agonist is selected from tapentadol and tramadol.

Also provided are embodiments wherein any embodiment above may be combined with any one or more of these embodiments, provided the combination is not mutually exclusive.

Tamper-proof and tamper-resistant formulating technologies have been developed for safer delivery of opioid antagonists, but such formulations are still abused resulting in opioid overdose. One such technology (Abuse Deterrent Prolonged Release Erosion Matrix (ADPREM); Egalet) utilizes a water-degradable polymer matrix technology that erodes from the surface at a constant rate. The matrix consists of one or more plasticizing polymers that cannot be crushed or melted. Another such technology (Abuse Resistant Technology (ART); Elite Laboratories) utilizes a proprietary coating technology consisting of various polymers that can sequester an opioid antagonist (naltrexone) in fragile micropellets that are indistinguishable from the pellets containing the opioid. The formulation is designed to release sequestered antagonist only if the dosage is crushed or otherwise damaged for extraction. Oral dosage forms are prepared by coating powders, crystals, granules, or pellets with various polymers to impart different characteristics. The formulations can release the active drug in both immediate and sustained release form. Chronodelivery formulations using this technology can effectively delay drug absorption for up to five hours. Aversion (Acura Pharmaceuticals) utilizes certain proprietary combinations of functional excipients (e.g., gelling agents) and active ingredients intended to discourage the most common methods of prescription drug misuse and abuse. Ingredients may include nasal irritants (e.g., capsaicin) and aversive agents (e.g., niacin). In some embodiments, the opioid agonist is in a tamper-proof formulation. In some embodiments, the opioid agonist is in a tamper-resistant formulation. In some embodiments, the opioid agonist is selected from Acurox® Oxycodone DETERx®, Oxycontin®, Egalet hydrocodone, Egalet morphine, Egalet oxycodone, Exalgo®, Opana®, Opana® ER, Vicodin®, Percocet® and Remoxy®.

Pharmaceutical Compositions

Also provided are pharmaceutical compositions comprising one or more opioid antagonist. In some embodiments the pharmaceutical compositions comprise an opioid antagonist and a pharmaceutically acceptable carrier. The carrier(s) must be "acceptable" in the sense of being compatible with the other ingredients of the formulation and not overly deleterious to the recipient thereof. Some embodiments of the present invention include a method of producing a pharmaceutical composition comprising admixing at least one opioid antagonist and a pharmaceutically acceptable carrier. Pharmaceutical compositions are applied directly to the nasal cavity using the devices described herein. In the case of a spray, this may be achieved for example by means of a metering atomizing spray pump.

Liquid preparations include solutions, suspensions and emulsions, for example, water or water-propylene glycol solutions. Additional ingredients in liquid preparations may include: antimicrobial preservatives, such as benzalkonium chloride (which may also act as a cationic surfactant and/or a permeation enhancer), methylparaben, sodium benzoate, benzoic acid, phenyl ethyl alcohol, and the like, and mixtures thereof; surfactants such as Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, polyethylene glycol (15)-hydroxystearate (Solutol® HS 15) and the like, and mixtures thereof; a tonicity agent such as: dextrose, lactose, sodium chloride, calcium chloride, magnesium chloride, sorbitol, sucrose, mannitol, trehalose, raffinose, polyethylene glycol, hydroxyethyl starch, glycine, and the like, and mixtures thereof; and a suspending agent such as microcrystalline cellulose, carboxymethylcellulose sodium NF, polyacrylic acid, magnesium aluminum silicate, xanthan gum, and the like, and mixtures thereof.

The opioid antagonists described herein can be formulated into pharmaceutical compositions using techniques well known to those in the art. Suitable pharmaceutically acceptable carriers, outside those mentioned herein, are known in the art; for example, see Remington: The Science and Practice of Pharmacy, 21st ed., Lippincott Williams & Wilkins, Philadelphia, Pa. (2005).

The opioid antagonists described herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., Journal of Pharmaceutical Sciences, 66:1-19 (1977). The acid addition salts may be obtained as the direct products of compound synthesis. In the alternative, the free base may be dissolved in a suitable solvent containing the appropriate acid and the salt isolated by evaporating the solvent or otherwise separating the salt and solvent. The opioid antagonists described herein may form solvates with standard low molecular weight solvents using methods known to the skilled artisan.

Accordingly, provided herein are pharmaceutical formulations for intranasal administration comprising, in an aqueous solution of not more than about 140 μL:
  between about 2 mg and about 12 mg of an opioid antagonist;
  between about 0.2 mg and about 1.2 mg of an isotonicity agent;
  between about 0.005 mg and about 0.015 mg of a compound which is a preservative, cationic surfactant, and/or permeation enhancer;
  between about 0.1 mg and about 0.5 mg of a stabilizing agent;
  an amount of an acid sufficient to achieve a pH of 3.5-5.5.

In some embodiments, said opioid antagonist is the only pharmaceutically active compound in said pharmaceutical composition.

In some embodiments, said opioid antagonist is naloxone hydrochloride, or a hydrate thereof.

In some embodiments, said opioid antagonist is naloxone hydrochloride dihydrate.

In some embodiments, the pharmaceutical formulation comprises an amount equivalent to about 4 mg to about 10 mg of naloxone hydrochloride. In some embodiments, the pharmaceutical formulation comprises an amount equivalent to an amount chosen from about 2 mg naloxone hydrochloride, about 4 mg of naloxone hydrochloride, and about 8 mg naloxone hydrochloride. In some embodiments, the pharmaceutical formulation comprises an amount equivalent to about 2 mg of naloxone hydrochloride. In some embodiments, the pharmaceutical formulation comprises an amount equivalent to about 4 mg of naloxone hydrochloride. In some embodiments, the pharmaceutical formulation comprises an amount equivalent to about 8 mg of naloxone hydrochloride. In some embodiments, the therapeutically effective amount is equivalent to about 3.4 mg of naloxone hydrochloride.

In some embodiments, the pharmaceutical formulation comprises about 2.2 mg to about 13.2 mg of naloxone hydrochloride dihydrate. In some embodiments, the pharmaceutical formulation comprises about 4.4 mg to about 11 mg of naloxone hydrochloride dihydrate. In some embodiments, the pharmaceutical formulation comprises an amount chosen from about 2.2 mg naloxone hydrochloride dihydrate, about 4.4 mg of naloxone hydrochloride dihydrate, and about 8.8 mg naloxone hydrochloride dihydrate. In some embodiments, the pharmaceutical formulation comprises about 2.2 mg of naloxone hydrochloride dihydrate. In some embodiments, the pharmaceutical formulation comprises about 4.4 mg of naloxone hydrochloride dihydrate. In some embodiments, the pharmaceutical formulation comprises about 8.8 mg of naloxone hydrochloride dihydrate.

In some embodiments, the device comprises about 4.4 mg naloxone hydrochloride dihydrate. In some embodiments, the device comprises about 2.2 mg naloxone hydrochloride dihydrate.

In some embodiments, the pharmaceutical composition is in an aqueous solution of about 100 μL.

In some embodiments, upon nasal delivery of said pharmaceutical composition to said patient, less than about 10% of said pharmaceutical composition leaves the nasal cavity via drainage into the nasopharynx or externally.

In some embodiments, the plasma concentration versus time curve of said naloxone hydrochloride in said patient has a $t_{max}$ of between about 20 and about 30 minutes.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in a patient has a $t_{max}$ of less than 30 minutes. In some embodiments, the plasma concentration versus time curve of said opioid antagonist in said patient has a $t_{max}$ of less than 25 minutes. In some embodiments, the plasma concentration versus time curve of said opioid antagonist in said patient has a $t_{max}$ of about 20 minutes. In some embodiments, the plasma concentration versus time curve of the opioid antagonist in the patient has a $t_{max}$ of less than 19 minutes. In some embodiments, the plasma concentration versus time curve of the opioid antagonist in the patient has a $t_{max}$ of about 18.5 minutes.

In some embodiments, delivery of said pharmaceutical formulation to a patient, provides occupancy at $t_{max}$ of said opioid antagonist at the opioid receptors in the respiratory control center of said patient of greater than about 90%. In some embodiments, delivery of said pharmaceutical formulation to said patient, provides occupancy at $t_{max}$ of said opioid antagonist at the opioid receptors in the respiratory control center of said patient of greater than about 95%. In some embodiments, delivery of said pharmaceutical formulation to said patient, provides occupancy at $t_{max}$ of said opioid antagonist at the opioid receptors in the respiratory control center of said patient of greater than about 99%.

In some embodiments, said patient is free from respiratory depression for at least about 1 hour following treatment comprising delivery of said therapeutically effective amount of said opioid antagonist. In some embodiments, said patient is free from respiratory depression for at least about 2 hours following treatment comprising delivery of said therapeutically effective amount of said opioid antagonist. In some embodiments, said patient is free from respiratory depression for at least about 4 hours following treatment comprising delivery of said therapeutically effective amount of said opioid antagonist. In some embodiments, said patient is free from respiratory depression for at least about 6 hours following treatment comprising delivery of said therapeutically effective amount of said opioid antagonist.

Also provided herein are pharmaceutical formulations for intranasal administration comprising, in an aqueous solution of not more than about 140 µL:
  about 2 mg or about 4 mg naloxone hydrochloride or a hydrate thereof;
  between about 0.2 mg and about 1.2 mg of an isotonicity agent;
  between about 0.005 mg and about 0.015 mg of a compound which is a preservative, cationic surfactant, and/or permeation enhancer;
  between about 0.1 mg and about 0.5 mg of a stabilizing agent;
  an amount of acid sufficient to achieve a pH of 3.5-5.5.

In some embodiments,
  the isotonicity agent is NaCl;
  the compound which is a preservative, cationic surfactant, and/or permeation enhancer is benzalkonium chloride;
  the stabilizing agent is disodium edetate; and
  the acid is hydrochloric acid.

In some embodiments, the pharmaceutical formulation comprises:
  about 2.2 mg or about 4.4 mg naloxone hydrochloride dihydrate;
  about 0.74 mg NaCl;
  about 0.01 mg benzalkonium chloride;
  about 0.2 mg disodium edetate; and
  an amount of hydrochloric acid sufficient to achieve a pH of 3.5-5.5.

In some embodiments, the pharmaceutical formulation comprises about 4 mg naloxone hydrochloride or a hydrate thereof. In some embodiments, the pharmaceutical formulation comprises about 2 mg naloxone hydrochloride or a hydrate thereof. In some embodiments, the pharmaceutical formulation comprises about 4.4 mg naloxone hydrochloride dihydrate. In some embodiments, the pharmaceutical formulation comprises about 2.2 mg naloxone hydrochloride dihydrate.

Also provided herein are pharmaceutical formulations for intranasal administration comprising, in an aqueous solution of about 100 µL:
  about 4 mg naloxone hydrochloride or a hydrate thereof;
  between about 0.2 mg and about 1.2 mg of an isotonicity agent;
  between about 0.005 mg and about 0.015 mg of a compound which is a preservative cationic surfactant, and/or permeation enhancer;
  between about 0.1 mg and about 0.5 mg of a stabilizing agent; and
  an amount of acid sufficient to achieve a pH of 3.5-5.5.

In some embodiments, the pharmaceutical formulation comprises:
  about 4.4 mg naloxone hydrochloride dihydrate;
  about 0.74 mg NaCl;
  about 0.01 mg benzalkonium chloride;
  about 0.2 mg disodium edetate; and
  an amount of hydrochloric acid sufficient to achieve a pH of 3.5-5.5.

Also provided herein are pharmaceutical formulations for intranasal administration comprising, in an aqueous solution of about 100 µL:
  about 2 mg naloxone hydrochloride or a hydrate thereof;
  between about 0.2 mg and about 1.2 mg of an isotonicity agent;
  between about 0.005 mg and about 0.015 mg of a compound which is a preservative, cationic surfactant, and/or permeation enhancer;
  between about 0.1 mg and about 0.5 mg of a stabilizing agent; and
  an amount of an acid sufficient to achieve a pH of 3.5-5.5.

In some embodiments, the pharmaceutical formulation comprises:
  about 2.2 mg naloxone hydrochloride dihydrate;
  about 0.74 mg NaCl;
  about 0.2 mg disodium edetate; and
  an amount of hydrochloric acid sufficient to achieve a pH of 3.5-5.5.

In some embodiments, the pharmaceutical formulation comprises about 4.4 mg naloxone hydrochloride dihydrate. In some embodiments, the pharmaceutical formulation comprises about 2.2 mg naloxone hydrochloride dihydrate.

Provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. In some embodiments, the therapeutically effective amount is equivalent to about 4.4 mg of naloxone hydrochloride. In some embodiments, the pharmaceutical composition comprises a solution of naloxone hydrochloride dihydrate. In some embodiments, the pharmaceutical composition further comprises one or more excipients selected from water and NaCl. In some embodiments, the pharmaceutical composition is substantially free of antimicrobial preservatives. In some embodiments, the device is substantially free of benzalkonium chloride, methylparaben, sodium benzoate, benzoic acid, phenyl ethyl alcohol. In some embodiments, the device is filled with the pharmaceutical composition in a sterile environment. In some embodiments, the pharmaceutical composition is storage-stable for about twelve months at about 25° C. In some embodiments, the pharmaceutical composition comprises less than 0.1% w/w antimicrobial preservatives. In some embodiments, the pharmaceutical composition comprises 0.01% w/w or less antimicrobial preservatives. In some embodiments, the pharmaceutical composition comprises 0.01% w/w-0.001% w/w antimicrobial preservatives. In some embodiments, the pharmaceutical composition comprises less than 0.001% w/w antimicrobial preservatives.

Also provided are devices for "combination-therapy" comprising pharmaceutical compositions comprising at least one opioid antagonist described herein, together with at least one known pharmaceutical agent and a pharmaceutically acceptable carrier. In some embodiments, the pharmaceutical composition comprises a short-acting opioid antagonist and a long-acting opioid antagonist. In some embodiments, the pharmaceutical composition comprises naloxone and naltrexone. In some embodiments, the pharmaceutical composition comprises naloxone and methylnaltrexone. In some embodiments, the pharmaceutical composition comprises naloxone and nalmefene.

Also provided are embodiments wherein any embodiment above may be combined with any one or more of these embodiments, provided the combination is not mutually exclusive.

Indications

Also provided are devices for use in treating opioid overdose and symptoms thereof and methods of using the devices. Naloxone prevents or reverses the effects of opioids including respiratory depression, sedation and hypotension. Also, it can reverse the psychotomimetic and dysphoric effects of agonist-antagonists such as pentazocine. Naloxone causes abrupt reversal of narcotic depression which may result in nausea, vomiting, sweating, tachycardia, increased blood pressure, tremulousness, seizures and cardiac arrest, however, there is no clinical experience with naloxone hydrochloride overdosage in humans. For this reason, also described herein is a method of preventing complications from severe opioid withdrawal, the method comprising administering a dose of naloxone according to the devices and/or formulations disclosed herein, and then monitoring the patient for a symptom selected from the group consisting of vomiting, sweating, tachycardia, increased blood pressure, tremulousness, seizures and cardiac arrest. In the mouse and rat the intravenous LD50 is 150±5 mg/kg and 109±4 mg/kg respectively. In acute subcutaneous toxicity studies in newborn rats the LD50 (95% CL) is 260 (228-296) mg/kg. Subcutaneous injection of 100 mg/kg/day in rats for 3 weeks produced only transient salivation and partial ptosis following injection: no toxic effects were seen at 10 mg/kg/day for 3 weeks.

Naloxone hydrochloride injection is indicated for the complete or partial reversal of narcotic depression, including respiratory depression, induced by opioids selected from: natural and synthetic narcotics, propoxyphene, methadone, and certain narcotic-antagonist analgesics: nalbuphine, pentazocine and butorphanol. Naloxone hydrochloride is also indicated for the diagnosis of suspected acute opioid overdosage. For the treatment of known or suspected narcotic overdose in adults an initial dose of 0.4 mg to 2 mg of naloxone hydrochloride intravenously is indicated. If the desired degree of counteraction and improvement in respiratory functions is not obtained, administration may be repeated at 2 to 3 minute intervals. If no response is observed after 10 mg of naloxone hydrochloride have been administered, the diagnosis of narcotic-induced or partial narcotic-induced toxicity should be questioned. The usual initial dose in children is 0.01 mg/kg body weight given IV. If this dose does not result in the desired degree of clinical improvement, a subsequent dose of 0.1 mg/kg body weight may be administered. When using naloxone hydrochloride injection in neonates a product containing 0.02 mg/mL (i.e., 0.002% w/v) should be used.

It has also been reported that naloxone hydrochloride is an effective agent for the reversal of the cardiovascular and respiratory depression associated with narcotic and possibly some non-narcotic overdoses. The authors stated that due to naloxone's pharmacokinetic profile, a continuous infusion protocol is recommended when prolonged narcotic antagonist effects are required. (Handal et al., Ann Emerg Med. 1983 July; 12(7):438-45).

Accordingly, also provided herein are methods of treating opioid overdose or a symptom thereof, comprising nasally administering to a patient in need thereof a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof. In some embodiments, the therapeutically effective amount of an opioid antagonist selected from naloxone and pharmaceutically acceptable salts thereof is delivered in not more than about 140 μL of an aqueous carrier solution.

In certain embodiments, also provided herein are methods of treating opioid overdose or a symptom thereof, comprising nasally administering to a patient in need thereof a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof in not more than about 140 μL of an aqueous carrier solution.

In certain embodiments are provided methods of treating opioid overdose, or a symptom thereof, comprising nasally administering with a spray device to a patient in need thereof a therapeutically effective amount of an opioid antagonist selected from naloxone and pharmaceutically acceptable salts thereof, wherein the spray device is capable of spraying droplets having a median droplet size between about 30 and about 100 µm.

In some embodiments, the spray device is capable of spraying a formulation having a median distribution volume (Dv(50)) Dv(50) of 30-70 µm and a Dv(90)<100 µm.

In certain embodiments, the spray device is capable of spraying in a manner that the percent of droplets less than 10 µm is less than 10%. In certain embodiments, the percent of droplets less than 10 µm is less than 5%. In certain embodiments, the percent of droplets less than 10 µm is less than 2%. In certain embodiments, the percent of droplets less than 10 µm is less than 1%.

In certain embodiments, the spray device is capable of spraying a uniform circular plume spray pattern with an ovality ratio close to 1. Ovality ratio is calculated as the quotient of the maximum diameter (Dmax) and the minimum diameter (Dmin) of a spray pattern taken orthogonal to the direction of spray flow (e.g., from the "top"). In certain embodiments, the ovality ratio is less than 2.0. In certain embodiments, the ovality ratio is less than 1.5. In certain embodiments, the ovality ratio is less than 1.3. In certain embodiments, the ovality ratio is less than 1.2. In certain embodiments, the ovality ratio is less than 1.1. In certain embodiments, the ovality ratio is about 1.0.

In certain embodiments, also provided herein are methods of treating opioid overdose or a symptom thereof, comprising nasally administering to a patient in need thereof a single dose of a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof in not more than about 140 µL of an aqueous carrier solution.

In some embodiments, said opioid antagonist is the only pharmaceutically active compound in said pharmaceutical composition.

In some embodiments, said opioid antagonist is naloxone hydrochloride. In some embodiments, said opioid antagonist is naloxone hydrochloride dihydrate.

In some embodiments, said pharmaceutical composition comprises a solution of naloxone hydrochloride, or a hydrate thereof.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

In some embodiments, said therapeutically effective amount is equivalent to about 4 mg to about 10 mg of naloxone hydrochloride. In some embodiments, said therapeutically effective amount is equivalent to an amount chosen from about 2 mg naloxone hydrochloride, about 4 mg of naloxone hydrochloride, and about 8 mg naloxone hydrochloride. In some embodiments, said therapeutically effective amount is equivalent to about 2 mg of naloxone hydrochloride. In some embodiments, said therapeutically effective amount is equivalent to about 4 mg of naloxone hydrochloride. In some embodiments, said therapeutically effective amount is equivalent to about 8 mg of naloxone hydrochloride. In some embodiments, the therapeutically effective amount is equivalent to about 3.4 mg of naloxone hydrochloride.

In some embodiments, said therapeutically effective amount is about 2.2 mg to about 13.2 mg of naloxone hydrochloride dihydrate. In some embodiments, said therapeutically effective amount is about 4.4 mg to about 11 mg of naloxone hydrochloride dihydrate. In some embodiments, said therapeutically effective amount is an amount chosen from about 2.2 mg naloxone hydrochloride dihydrate, about 4.4 mg of naloxone hydrochloride dihydrate, and about 8.8 mg naloxone hydrochloride dihydrate. In some embodiments, said therapeutically effective amount is about 2.2 mg of naloxone hydrochloride dihydrate. In some embodiments, said therapeutically effective amount is about 4.4 mg of naloxone hydrochloride dihydrate. In some embodiments, said therapeutically effective amount is about 8.8 mg of naloxone hydrochloride dihydrate.

In some embodiments, said symptom is chosen from respiratory depression and central nervous system depression.

In some embodiments, said patient exhibits any of unresponsiveness to stimulus, unconsciousness, stopped breathing; erratic or stopped pulse, choking or gurgling sounds, blue or purple fingernails or lips, slack or limp muscle tone, contracted pupils, and vomiting.

In some embodiments, said patient is not breathing.

In some embodiments, said patient is in a lying, supine, or recovery position.

In some embodiments, said patient is in a lying position.
In some embodiments, said patient is in a supine position.
In some embodiments, said patient is a recovery position.

In some embodiments, said therapeutically effective amount is equivalent to about 2 mg to about 10 mg of naloxone hydrochloride.

In some embodiments, said therapeutically effective amount is equivalent to an amount chosen from about 2 mg naloxone hydrochloride, about 4 mg of naloxone hydrochloride, and about 8 mg naloxone hydrochloride.

In some embodiments, said therapeutically effective amount is equivalent to about 2 mg of naloxone hydrochloride.

In some embodiments, said therapeutically effective amount is equivalent to about 4 mg of naloxone hydrochloride.

In some embodiments, said therapeutically effective amount is equivalent to about 8 mg of naloxone hydrochloride.

In some embodiments, said opioid antagonist is the only pharmaceutically active compound in said pharmaceutical composition.

In some embodiments, said opioid antagonist is naloxone hydrochloride.

In some embodiments, said nasally administering is accomplished using a pre-primed device adapted for nasal delivery of a pharmaceutical composition.

In some embodiments, upon nasal delivery of said pharmaceutical composition to said patient, less than about 20% of said pharmaceutical composition leaves the nasal cavity via drainage into the nasopharynx or externally.

In some embodiments, upon nasal delivery of said pharmaceutical composition to said patient, less than about 10% of said pharmaceutical composition leaves the nasal cavity via drainage into the nasopharynx or externally.

In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $t_{max}$ of less than 30 minutes.

In some embodiments, the plasma concentration versus time curve of said opioid antagonist in said patient has a $t_{max}$ of less than 25 minutes.

In some embodiments, the plasma concentration versus time curve of said opioid antagonist in said patient has a $t_{max}$ of about 20 minutes.

In some embodiments, said opioid overdose symptom is selected from: respiratory depression, central nervous system depression, and cardiovascular depression.

In some embodiments, said opioid overdose symptom is respiratory depression induced by opioids.

In some embodiments, said respiratory depression is caused by the illicit use of opioids or by an accidental misuse of opioids during medical opioid therapy.

In some embodiments, said respiratory depression is induced by opioids selected from: natural and synthetic narcotics, propoxyphene, methadone, nalbuphine, pentazocine and butorphanol.

In some embodiments, said respiratory depression is induced by an opioid selected from codeine, morphine, methadone, fentanyl, oxycodone HCl, hydrocodone bitartrate, hydromorphone, oxymorphone, meperidine, propoxyphene, opium, heroin, tramadol, tapentadol.

In some embodiments, said patient is free from respiratory depression for at least about 1 hour following treatment comprising delivery of said therapeutically effective amount of said opioid antagonist.

In some embodiments, said patient is free from respiratory depression for at least about 2 hours following treatment comprising delivery of said therapeutically effective amount of said opioid antagonist.

In some embodiments, said patient is free from respiratory depression for at least about 4 hours following treatment comprising delivery of said therapeutically effective amount of said opioid antagonist.

In some embodiments, said patient is free from respiratory depression for at least about 6 hours following treatment comprising delivery of said therapeutically effective amount of said opioid antagonist.

Also provided are embodiments wherein any embodiment above may be combined with any one or more of these embodiments, provided the combination is not mutually exclusive.

Also provided are the devices, pharmaceutical compositions, kits, and methods of treatment described herein for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension. Also provided are the devices, pharmaceutical compositions, kits, and methods of treatment described herein for use in the reversal of respiratory depression induced by opioids. In some embodiments, the respiratory depression is caused by the illicit use of opioids or by an accidental misuse of opioids during medical opioid therapy. Also provided are the devices, pharmaceutical compositions, kits, and methods of treatment described herein for use in the complete or partial reversal of narcotic depression, including respiratory depression, induced by opioids selected from: natural and synthetic narcotics, propoxyphene, methadone, nalbuphine, pentazocine and butorphanol. In some embodiments, narcotic depression, including respiratory depression, is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are devices, pharmaceutical formulations, and kits for, and methods of, treating opioid overdose or a symptom thereof, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the patient is not breathing. Also provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 4 mg to about 12 mg of naloxone hydrochloride. In some embodiments, the therapeutically effective amount is equivalent to about 2 mg to about 24 mg of naloxone hydrochloride. In some embodiments, the therapeutically effective amount is equivalent to about 3 mg to about 18 mg of naloxone hydrochloride. In some embodiments, the therapeutically effective amount is equivalent to about 4 mg to about 10 mg of naloxone hydrochloride. In some embodiments, the therapeutically effective amount is equivalent to about 5 mg to about 11 mg of naloxone hydrochloride. In some embodiments, the therapeutically effective amount is equivalent to about 6 mg to about 10 mg of naloxone hydrochloride. In some embodiments, the therapeutically effective amount is equivalent to about 4 mg to about 8 mg of naloxone hydrochloride. In some embodiments, the therapeutically effective amount is equivalent to about 7 mg to about 9 mg of naloxone hydrochloride. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the therapeutically effective amount is equivalent to about 5 mg of naloxone hydrochloride. In some embodiments, the therapeutically effective amount is equivalent to about 6 mg of naloxone hydrochloride. In some embodiments, the therapeutically effective amount is equivalent to about 7 mg of naloxone hydrochloride. In some embodiments, the therapeutically effective amount is equivalent to about 8 mg of naloxone hydrochloride. In some embodiments, the therapeutically effective amount is equivalent to about 9 mg of naloxone hydrochloride. In some embodiments, the therapeutically effective amount is equivalent to about 10 mg of naloxone hydrochloride. In some embodiments, the therapeutically effective amount is equivalent to about 11 mg of naloxone hydrochloride. In some embodiments, the therapeutically effective amount is equivalent to about 12 mg of naloxone hydrochloride. In some embodiments, the opioid antagonist is the only pharmaceutically active compound in pharmaceutical composition. In some embodiments, the opioid antagonist is naloxone hydrochloride. In some embodiments, the opioid antagonist is anhydrous naloxone hydrochloride. In some embodiments, the opioid antagonist is the only pharmaceutically active compound in said pharmaceutical composition. In some embodiments, the opioid antagonist is naloxone hydrochloride. In some embodiments, the pharmaceutical composition comprises a solution of naloxone hydrochloride. In some embodiments, the nasally administering is accomplished using a device described herein. In some embodiments, the opioid overdose symptom is selected from: respiratory depression, postoperative opioid respiratory depression, altered level consciousness, miotic pupils, cardiovascular depression, hypoxemia, acute lung injury, aspiration pneumonia, sedation, and hypotension. In some embodiments, the opioid overdose symptom is respiratory depression induced by opioids. In some embodiments, the respiratory depression is caused by the illicit use of opioids or by an accidental misuse of opioids during medical opioid therapy. In some embodiments, the respiratory depression is induced by opioids selected from: natural and synthetic narcotics, propoxyphene, methadone, nalbuphine, pentazocine and butorphanol. In some embodiments, the respiratory depression is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are devices, kits, and pharmaceutical formulations for, and methods of, treating opioid overdose or a symptom thereof, comprising nasally administering to a patient in need thereof a therapeutically effective amount of an opioid antagonist together and at least one known pharmaceutical agent. In some embodiments, the method comprises nasally administering to a patient in need thereof therapeutically effective amounts of a short-acting opioid antagonist and a long-acting opioid antagonist. In some embodiments, the method comprises nasally administering to a patient in need thereof therapeutically effective amounts of naloxone and naltrexone. In some embodiments, the method comprises nasally administering to a patient in need thereof therapeutically effective amounts of naloxone and methylnaltrexone. In some embodiments, the method comprises nasally administering to a patient in need thereof therapeutically effective amounts of naloxone and nalmefene.

Also provided are devices, kits, and pharmaceutical formulations for, and methods of, reversing the psychotomimetic and dysphoric effects of agonist-antagonists such as pentazocine, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4.4 mg of naloxone hydrochloride. In some embodiments, the therapeutically effective amount is equivalent to about 4 mg of naloxone hydrochloride dihydrate. In some embodiments, the nasally administering is accomplished using a device described herein.

Also provided are devices, kits, and pharmaceutical formulations for, and methods of, diagnosis of suspected acute opioid overdosage, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating opioid addiction, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating septic shock, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating opioid overdose or a symptom thereof, reversing the psychotomimetic and dysphoric effects of agonist-antagonists such as pentazocine, diagnosing suspected acute opioid overdosage, treating opioid addiction, or treating septic shock, comprising nasally administering to a patient in need thereof a therapeutically effective amount of an opioid antagonist, wherein the therapeutically effective amount is about 2 mg to about 12 mg. In some embodiments, the therapeutically effective amount is equivalent to about 4.4 mg of naloxone hydrochloride dihydrate. In some embodiments, the therapeutically effective amount is equivalent to about 4 mg of naloxone hydrochloride. In some embodiments, the patient is an opioid overdose patient. In some embodiments, the patient is not breathing. In some embodiments, the opioid antagonist is the only pharmaceutically active compound in said pharmaceutical composition. In some embodiments, the opioid antagonist is selected from naltrexone, methylnaltrexone, and nalmefene, and pharmaceutically acceptable salts thereof. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the nasally administering is accomplished using a device described herein. In some embodiments, the opioid overdose symptom is selected from: respiratory depression, postoperative opioid respiratory depression, altered level consciousness, miotic pupils, cardiovascular depression, hypoxemia, acute lung injury, aspiration pneumonia, sedation, and hypotension. In some embodiments, the opioid overdose symptom is respiratory depression induced by opioids. In some embodiments, the respiratory depression is caused by the illicit use of opioids or by an accidental misuse of opioids during medical opioid therapy. In some embodiments, the respiratory depression is induced by opioids selected from: natural and synthetic narcotics, propoxyphene, methadone, nalbuphine, pentazocine and butorphanol. In some embodiments, the respiratory depression is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are embodiments wherein any embodiment above may be combined with any one or more of these embodiments, provided the combination is not mutually exclusive. Also provided herein are uses in the treatment of indications or one or more symptoms thereof as disclosed herein, and uses in the manufacture of medicaments for the treatment of indications or one or more symptoms thereof as disclosed herein, equivalent in scope to any embodiment disclosed herein, or any combination thereof that is not mutually exclusive. The methods and uses may employ any of the devices disclosed herein or any combination thereof that is not mutually exclusive, or any of the pharmaceutical formulations disclosed herein or any combination thereof that is not mutually exclusive.

Receptor Occupancy

Also provided are devices for use in treating opioid overdose and symptoms thereof and methods of using the devices, which provide a high level of brain opioid receptor occupancy as may be determined, for example, by positron emission tomography (PET). PET and single-photon emission computed tomography (SPECT) are noninvasive imaging techniques that can give insight into the relationship between target occupancy and drug efficacy, provided a suitable radioligand is available. Although SPECT has certain advantages (e.g., a long half-life of the radionuclides), the spatial and temporal resolution as well as the labeling possibilities of this technique are limited.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides. Positron-emitting radionuclides include $^{11}$C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I. Non-metal radionuclides may be covalently linked to the targeting molecule by reactions well known from the state of art. When the radionuclide is a metallic positron-emitter, it is understood that labeling may require the use of a chelating agent. Such chelating agents are well known from the state of the art.

The positron-emitter labeled compound is administered directly, e.g., IV, or indirectly, e.g., IN, into the subject's vascular system, from where it passes through the blood-brain barrier. Once the tracer has had sufficient time to associate with the target of interest, the individual is placed within in a scanning device comprising ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored. An image is then generated of the part of the individual's brain to which the compound has distributed.

PET studies are useful for comparing nasal delivery of naloxone using the devices and at the doses described herein, to typical nasal doses of naloxone (such as 1-2 mg), to delivery of naloxone using other nasal devices (such as the MAD™) and by other routes of administration such IM or IV naloxone or oral naltrexone or nalmefene. Further comparisons may be made between nasal administration in the upright versus the lying or supine positions. Useful measures that may be determined in such studies are the time to onset of action, brain half-life, and the percent receptor binding or occupancy of a patient's opioid receptors, for example, the μ-opioid receptors in the respiratory center in the medulla oblongata.

[$^{11}$C]Carfentanil (CFN) is a μ-opioid agonist used for in vivo PET studies of μ-opioid receptors. One such study involved healthy male volunteers assigned at enrolment to receive either naltrexone or a novel μ-opioid receptor inverse agonist (GSK1521498) (Rabiner et al., *Pharmacological differentiation of opioid receptor antagonists by molecular and functional imaging of target occupancy and food reward-related brain activation in humans*. Molecular Psychiatry (2011) 16, 826-835). Each participant underwent up to three [$^{11}$C]-carfentanil PET scans and two functional magnetic resonance imaging (fMRI) examinations: one [$^{11}$C]-carfentanil PET scan and one fMRI scan at baseline (before dosing) and up to two PET scans and one fMRI scan following oral administration of a single dose of GSK1521498 or naltrexone. The administered doses of GSK1521498 or naltrexone were chosen adaptively to optimize the estimation of the dose-occupancy relationship for each drug on the basis of data acquired from the preceding examinations in the study. The administered dose range was 0.4-100 mg for GSK1521498, and 2-50 mg for naltrexone. The maximum doses administered were equal to the maximum tolerated dose of GSK1521498 determined in the first-in-human study and the standard clinical dose of naltrexone used for alcohol dependence. The times and doses of the two post-dose [$^{11}$C]-carfentanil PET scans were chosen adaptively for each subject to optimize estimation of the relationship between plasma concentration and receptor occupancy. Post-dose [$^{11}$C]-carfentanil PET scans were acquired at 3-36 h after the administration of GSK1521498 and at 3-88 h after the administration of naltrexone. Post-dose fMRI scans were acquired within 60 min of the first post-dose PET scan. Venous blood samples were collected at regular intervals throughout the scanning sessions. High-performance liquid chromatography/mass spectrometry/mass spectrometry was used to estimate the plasma concentrations of GSK1521498, naltrexone, and the major metabolite of naltrexone, 6-β-naltrexol. Drug plasma concentration at the start of each PET scan was used to model the relationship between drug concentrations and μ-opioid receptor occupancies. Carfentanil (methyl 1-(2-phenylethyl)-4-(phenyl(propanoyl)amino)-4-piperidinecarboxylate 3S, 5S; Advanced Biochemical Compounds, Radeberg, Germany), a potent selective μ-opioid receptor agonist, was labelled with carbon-11 using a modification of a previously described method implemented using a semiautomated Modular Lab Multifunctional Synthetic Module (Eckert & Ziegler, Berlin, Germany). The final product was reformulated in sterile 0.9% saline containing ~10% ethanol (v/v) and satisfied quality control criteria for specific activity and purity before being injected intravenously as a slow bolus over ~30 s. PET scanning was conducted in three-dimensional mode using a Siemens Biograph 6 Hi-Rez PET-CT for the naltrexone group and a Siemens Biograph 6 TruePoint PET-CT for the GSK1521498 group (Siemens Healthcare, Erlangen, Germany). A low-dose CT scan was acquired for attenuation correction before the administration of the radiotracer. Dynamic PET data were acquired for 90 min after [$^{11}$C]-carfentanil injection, binned into 26 frames (durations: 8×15 s, 3×60 s, 5×2 min, 5×5 min and 5×10 min), reconstructed using Fourier re-binning and a two-dimensional-filtered back projection algorithm and then smoothed with a two-dimensional Gaussian filter (5 mm at full width half maximum). Dynamic PET images were registered to each participant's T1-weighted anatomical MRI volume and corrected for head motion using SPM5 software (Wellcome Trust Centre for Neuroimaging). Pre-selected regions of interests were defined bilaterally on the T1-weighted anatomical volume using an in-house atlas and applied to the dynamic PET data to generate regional time-activity curves. The [$^{11}$C]-carfentanil-specific binding was quantified as binding potential relative to the non-displaceable compartment ($BP_{ND}$)

$$BP_{ND} = \frac{f_{ND} B_{avail}}{K_D}$$

where $f_{ND}$ is the free fraction of the radioligand in the brain, $K_D$ is the affinity of [$^{11}$C]-carfentanil, and $B_{avail}$ is the density of the available μ-opioid receptors. Regional [$^{11}$C]-carfentanil $BP_{ND}$ was estimated using a reference tissue model with the occipital cortex as the reference region. Drug related occupancy of the μ-opioid receptor was quantified as a reduction of [$^{11}$C]-carfentanil.

$$\text{Occupancy}_{Drug} = \frac{BP_{ND}^{Baseline} - BP_{ND}^{Drug}}{BP_{ND}^{Baseline}}$$

The affinity constant for each drug at the μ-opioid receptor (effective concentration 50 ($EC_{50}$)) was estimated by fitting the plasma concentration measured at the start of the PET scan, $C^P_{Drug}$, to the estimated occupancy:

$$\text{Occupancy}_{Drug} = \frac{C^P_{Drug}}{C^P_{Drug} + EC_{50}}$$

The use of a sensitive non-tomographic positron detecting system to measure the dose-response curve of naloxone in human brain has also been reported. [$^{11}$C]Diprenorphine was administered to normal volunteers in tracer amounts and, 30 min later, various bolus doses of naloxone were given (1.5-160 μg/kg) intravenously and change in [$^{11}$C] diprenorphine binding monitored over the next 30 min. Approximately 13 μg/kg of naloxone (approximately 1 mg in an 80 kg man) was required to produce an estimated 50% receptor occupation, consistent with the clinical dose of naloxone used to reverse opiate overdose (0.4 mg-1.2 mg). Melichar et al., *Naloxone displacement at opioid receptor sites measured in vivo in the human brain*. Eur J Pharmacol. 2003 Jan. 17; 459(2-3):217-9).

In some embodiments of the devices, kits, pharmaceutical formulations, and methods disclosed above, delivery of the therapeutically effective amount to the patient, provides occupancy at $t_{max}$ of the opioid antagonist at the opioid receptors in the respiratory control center of the patient of greater than about 90%. In some embodiments, delivery of the therapeutically effective amount to the patient, provides occupancy at $t_{max}$ of the opioid antagonist at the opioid receptors in the respiratory control center of the patient of greater than about 95%. In some embodiments, delivery of the therapeutically effective amount to the patient, provides occupancy at $t_{max}$ of the opioid antagonist at the opioid receptors in the respiratory control center of the patient of greater than about 99%. In some embodiments, delivery of the therapeutically effective amount to the patient, provides occupancy at $t_{max}$ of the opioid antagonist at the opioid receptors in the respiratory control center of the patient of about 100%.

Also provided are embodiments wherein any embodiment described above may be combined with any one or more of these embodiments, provided the combination is not mutually exclusive.

EXAMPLES

Example 1: Pharmacokinetics and Safety of Intranasal Naloxone in Humans (Study 1)

A clinical trial was performed for which the primary objectives were to determine the pharmacokinetics (PK) of 2 intranasal (IN) doses (2 mg and 4 mg) of naloxone compared to a 0.4 mg dose of naloxone administered intramuscularly (IM) and to identify an appropriate IN dose that could achieve systemic exposure comparable to an approved parenteral dose. The secondary objectives were to determine the safety of IN naloxone, specifically with respect to nasal irritation (erythema, edema, and erosion).

Methodology: This was an inpatient open-label, randomized, 3-period, 3-treatment, 6-sequence, crossover study involving 14 healthy volunteers. Subjects were assigned to one of the 6 sequences with 2 subjects in each sequence (2 sequences had 3 subjects). Each subject received 3 naloxone doses, a single 2 mg IN dose (one spray of 0.1 mL of 10 mg/mL solution in each nostril), a single 4 mg IN dose (2 sprays of 0.1 mL per spray of 10 mg/mL solution in each nostril) and a single 0.4 mg IM dose, in the 3 dosing periods (Table 1). Subjects stayed in the inpatient facility for 11 days to complete the entire study and were discharged on the next day after the last dose. Subjects returned for a final follow-up visit 3-5 days after discharge. After obtaining informed consent, subjects were screened for eligibility to participate in the study including medical history, physical examination, clinical chemistry, coagulation markers, hematology, infectious disease serology, urinalysis, urine drug and alcohol toxicology screen, vital signs and electrocardiogram (ECG). On the day after clinic admission, subjects were administered study drug in randomized order with a 4-day washout period between doses until all three doses were administered. Blood was collected for naloxone PK prior to dosing and approximately 2.5, 5, 10, 15, 20, 30, 45, 60, 120, 180, 240, 300, 360, 480, and 720 min after the start of study drug administration. On days of study drug administration, a 12-lead ECG was performed approximately 60 min prior to dosing and at approximately 60 and 480 min post-dose. Vital signs were measured pre-dose and approximately 30, 60, 120, and 480 min post-dose. On dosing days, the order of assessments was ECG, vital signs, then PK blood collection when scheduled at the same nominal times. ECG and vital signs were collected within the 10-min period before the nominal time of blood collections. At screening, admission, discharge, and follow-up, ECG and vital signs were checked once per day. Vital signs were also checked once on the day after naloxone administration. Clinical laboratory measurements were repeated after the last PK blood draw prior to clinic discharge. AEs were assessed by spontaneous reports by subjects, examination of the nasal mucosa, physical examination, vital signs, ECG, and clinical laboratory parameters.

Main Criteria for Inclusion/Exclusion: Healthy volunteer adults with a body mass index (BMI) of 18-30 kg/m².

Investigational Product, Dose and Mode of Administration: Naloxone given IN was at a dose of 2 mg (1 squirt in each nostril delivered 0.1 mL of 10 mg/mL naloxone) and 4 mg (2 squirts in each nostril delivered 0.2 mL/nostril at 10 mg/mL naloxone, using two devices). IN naloxone was administered using a Pfeiffer (Aptar) BiDose liquid device with the subject in a fully supine position.

Duration of Treatment: Each IN and IM dose was administered once in each subject in random sequence.

Reference Therapy, Dose and Mode of Administration: Naloxone was given IM at a dose of 0.4 mg in 1.0 mL with a 23-g needle as a single injection in the gluteus maximus muscle.

PK Evaluation: Blood was collected in sodium heparin containing tubes for naloxone PK prior to dosing and 2.5, 5, 10, 15, 20, 30, 45, 60, 120, 180, 240, 300, 360, 480, and 720 min after the start of study drug administration. Non-compartmental PK parameters including $C_{max}$, $t_{max}$, AUC to infinity ($AUC_{0-\infty}$), AUC to last measurable concentration ($AUC_{0-t}$), $t_{1/2}$, $\lambda_z$, and apparent clearance (CL/F) were determined. Values of $t_{1/2}$ were determined from the log-linear decline in plasma concentrations from 2 to 6 or 8 h.

Safety Evaluation: Heart rate, blood pressure, and respiration rate was recorded before naloxone dosing and at approximately 30, 60, 120, and 480 min after dosing. These vital signs and temperature were also measured at screening, clinic intake, one day after each dosing session and at follow-up. A 12-lead ECG was obtained prior to and approximately 60 and 480 min after each naloxone dose, as well as during screening, clinic intake, and follow-up. ECG and vital signs were taken within the 10-min period before the nominal time for blood collections. AEs were recorded from the start of study-drug administration until clinic discharge. AEs were recorded relative to each dosing session to attempt to establish a relationship between the AE and type of naloxone dose administered. An examination of the nasal passage was conducted at Day-1 to establish eligibility and at pre-dose, 5 min, 30 min, 60 min, 4 h, and 24 h post naloxone administration to evaluate evidence of irritation to the nasal mucosa. Clinical laboratory measurements were done prior to the first drug administration and on the day of clinic release.

Statistical Analysis of PK Parameters: $C_{max}$, $t_{max}$ and AUC for 2 and 4 mg IN naloxone were compared with those for 0.4 mg IM naloxone. Within an ANOVA framework, comparisons of natural log (LN) transformed PK parameters ($C_{max}$ and AUC) for IN versus IM naloxone treatments were performed. The 90% confidence interval (CI) for the ratio (IN/IM) of the least squares means of AUC and $C_{max}$ parameters was constructed. These 90% CI were obtained by exponentiation of the 90% confidence intervals for the difference between the least squares means based upon a LN scale. In addition, dose adjusted values for AUCs and $C_{max}$ based upon a 0.4 mg dose were calculated (Tables 4-7). The relative extent of absorption (relative bioavailability, $F_{rel}$) of intranasal (IN versus IM) was estimated from the dose-corrected AUCs.

Statistical Analysis of Adverse Events: AEs were coded using the Medical Dictionary for Regulatory Activities (MedDRA), version 19. Preferred terms and are grouped by system, organ, class (SOC) designation. AEs are presented as a listing including the start date, stop date, severity, relationship, outcome, and duration.

Pharmacokinetics Results: The mean dose delivered for the 2 mg IN naloxone dose was 1.71 mg (range 1.50 mg to 1.80 mg) and for the 4 mg IN naloxone dose it was 3.40 mg (range 2.93 mg to 3.65 mg). This was 84-85% of the target dose. The overall % coefficient of variation (% CV) for the delivered dose from all 42 devices was 6.9% (Table 9). Preparation time of the IN doses took less than one third of the time to prepare the IM injection (70 seconds for the IM injection and 20 seconds for the IN administration) (Table 8). The time to prepare the IM injection did not include loading the syringe. Since the one purpose of the study was to determine if peak naloxone plasma concentrations ($C_{max}$) and AUCs following IN 2 mg and IN 4 mg administrations were equivalent to, or greater than IM 0.4 mg dosing, AUCs and $C_{max}$ values were compared without considering the dose difference among treatments. The $C_{max}$, $AUC_{0-t}$, and $AUC_{0-\infty}$ for both the 2 mg IN and 4 mg IN doses were statistically significantly greater than those for the 0.4 mg IM dose (p<0.001). The geometric least square means for $C_{max}$ were 2.18 ng/mL, 3.96 ng/mL, and 0.754 ng/mL for IN 2 mg, IN 4 mg and IM 0.4 mg, respectively. The geometric least square means for $AUC_{0-\infty}$ were 3.32 ng·h/mL, 5.47 ng·h/mL and 1.39 ng·h/mL for IN 2 mg, IN 4 mg and IM 0.4 mg respectively. The geometric least squares mean ratios for IN 2 mg/IM 0.4 mg were 290% for $C_{max}$ and 239% for $AUC_{0-\infty}$. The ratios for IN 4 mg/IM 0.4 mg were 525% for $C_{max}$ and 394% for $AUC_{0-\infty}$. There were no statistically significant differences between the routes and doses with respect to $t_{max}$, suggesting peak effects would occur at similar times for all treatments. However, the mean $t_{max}$ values did trend lower for the IN route versus IM, and for 4 mg IN versus 2 mg IN. (See Table 2). In comparing the extent of systemic absorption of IN to IM dosing, the $F_{rel}$ estimates were 55.7% and 46.3% for IN 2 mg and 4 mg, respectively. See Table 3.

Safety Results: No erythema, edema, erosion, or other sign was observed in the nasal cavity prior to or after any IN administration of naloxone at 2 and 4 mg to both nostrils. One subject experienced mild transient (over 3 min) pharyngeal pain coincident with the application of the 2 mg IN dose. This pain resolved spontaneously. Vital signs, ECG, and clinical laboratory parameters did not reveal any clinically noteworthy changes after naloxone administration. There was no evidence of QTcF prolongation.

TABLE 1

Order of Naloxone Doses and Route of Administration for each Subject.

| # | Subject ID | Sequence # | Dosing Session #1 Day 1 | Dosing Session #2 Day 5 | Dosing Session #3 Day 9 |
|---|---|---|---|---|---|
| 1 | 102 | 5 | 4 mg IN | 2 mg IN | 0.4 mg IM |
| 2 | 107 | 6 | 0.4 mg IM | 4 mg IN | 2 mg IN |
| 3 | 112 | 1 | 2 mg IN | 4 mg IN | 0.4 mg IM |
| 4 | 117 | 3 | 0.4 mg IM | 2 mg IN | 4 mg IN |
| 5 | 120 | 1 | 2 mg IN | 4 mg IN | 0.4 mg IM |
| 6 | 123 | 2 | 4 mg IN | 0.4 mg IM | 2 mg IN |
| 7 | 127 | 3 | 0.4 mg IM | 2 mg IN | 4 mg IN |
| 8 | 128 | 5 | 4 mg IN | 2 mg IN | 0.4 mg IM |

TABLE 1-continued

Order of Naloxone Doses and Route of Administration for each Subject.

| # | Subject ID | Sequence # | Dosing Session #1 Day 1 | Dosing Session #2 Day 5 | Dosing Session #3 Day 9 |
|---|---|---|---|---|---|
| 9 | 133 | 2 | 4 mg IN | 0.4 mg IM | 2 mg IN |
| 10 | 113 | 4 | 2 mg IN | 0.4 mg IM | 4 mg IN |
| 11 | 114 | 1 | 2 mg IN | 4 mg IN | 0.4 mg IM |
| 12 | 119 | 6 | 0.4 mg IM | 4 mg IN | 2 mg IN |
| 13 | 125 | 4 | 2 mg IN | 0.4 mg IM | 4 mg IN |
| 14 | 135 | 5 | 4 mg IN | 2 mg IN | 0.4 mg IM |

TABLE 2

Summary of Naloxone Pharmacokinetic Parameters Following Naloxone as 0.4 mg Intramuscular (IM), 2 mg Intranasal (IN), and 4 mg IN Administrations.

| | 0.4 mg IM | | 2 mg IN | | 4 mg IN | |
|---|---|---|---|---|---|---|
| Parameter | Mean | % CV | Mean | % CV | Mean | % CV |
| Dose (mg) | 0.400 | — | 1.714 | 5.7 | 3.403 | 5.7 |
| $C_{max}$ (ng/mL) | 0.765 | 27.6 | 2.32 | 41.2 | 4.55 | 63.7 |
| $t_{max}$ (min) | 20.34 | 36.1 | 19.98 | 31.0 | 18.42 | 33.6 |
| $AUC_{0-t}$ ng·h/mL | 1.38 | 19.9 | 3.41 | 29.5 | 5.63 | 27.6 |
| $AUC_{0-\infty}$ (ng·h/mL) | 1.42 | 19.2 | 3.44 | 29.3 | 5.68 | 27.6 |
| $\lambda_z$ (1/h) | 0.593 | 16.6 | 0.588 | 0.572 | 8.0 | 10.2 |
| $t_{1/2}$ (h) | 1.21 | 20.1 | 1.19 | 8.3 | 1.22 | 10.2 |

TABLE 3

Summary of Naloxone Pharmacokinetic Parameters Following Naloxone as 0.4 mg Intramuscular (IM), 2 mg Intranasal (IN), and 4 mg IN Adminstrations with Dose Normalized to 0.4 mg.

| | 0.4 mg IM | | 2 mg IN | | 4 mg IN | |
|---|---|---|---|---|---|---|
| Parameter | Mean | % CV | Mean | % CV | Mean | % CV |
| $AUC_{0-t/D}$ ng·h/mL | 1.38 | 19.9 | 0.796 | 28.7 | 0.667 | 29.4 |
| $AUC_{0-\infty/D}$ ng·h/mL | 1.42 | 19.2 | | | 0.804 | 29.3 |
| $F_{rel}$ | | | 0.571 | 24.5 | 0.475 | 25.3 |

TABLE 4

Statistical Comparison of Geometric Least Squares Mean (GLSM) of Pharmacokinetic Parameters for IN Naloxone at a Dose of 2 mg to IM Naloxone at a Dose of 0.4 mg with No Dose Adjustment.

| Parameter | GLSM 2 mg IN | GLSM 0.4 mg IM | GLSM Ratio IM/IN % | 90% Cl of Ratio | p-value |
|---|---|---|---|---|---|
| $C_{max}$ (ng/mL) | 2.18 | 0.754 | 290 | 237-353 | <0.001 |
| $t_{max}$ (h) | 0.333 | 0.308 | — | — | 1.000 |
| $AUC_{0-t}$ (ng·h/mL) | 3.28 | 1.35 | 243 | 219-270 | <0.001 |
| $AUC_{0-\infty}$ (ng·h/mL) | 3.32 | 1.39 | 239 | 215-264 | <0.001 |
| $t_{1/2}$ (h) | 1.18 | 1.19 | 102 | 94.0-111 | 0.6507 |

TABLE 5

Statistical Comparison of Geometric Least Squares Mean (GLSM) of Pharmacokinetic Parameters for IN Naloxone at a Dose of 4 mg to IM Naloxone at a Dose of 0.4 mg with No Dose Adjustment.

| Parameter | GLSM 4 mg IN | GLSM 0.4 mg IM | GLSM Ratio IM/IN % | 90% Cl of Ratio | p-value |
|---|---|---|---|---|---|
| $C_{max}$ (ng/mL) | 3.96 | 0.754 | 525 | 431-640 | <0.001 |
| $AUC_{0-t}$ (ng·h/mL) | 5.41 | 1.35 | 401 | 361-445 | <0.001 |
| $AUC_{0-\infty}$ (ng·h/mL) | 5.47 | 1.39 | 394 | 355-436 | <0.001 |
| $t_{1/2}$ (h) | 1.22 | 1.19 | 102 | 94.0-111 | 0.651 |

TABLE 6

Statistical Comparison of Geometric Least Squares Mean (GLSM) of Pharmacokinetic Parameters for IN Naloxone at a Dose of 2 mg to IM Naloxone at a Dose of 0.4 mg with Dose Adjustment to 0.4 mg.

| Parameter | GLSM 2 mg IN | GLSM 0.4 mg IM | GLSM Ratio IM/IN % | 90% Cl of Ratio | p-value |
|---|---|---|---|---|---|
| $C_{max/D}$ (ng/mL) | 0.510 | 0.755 | 67.6 | 55.3-82.7 | 0.0028 |
| $t_{max}$ (h) | 0.333 | 0.308 | — | — | 1.000 |

TABLE 6-continued

Statistical Comparison of Geometric Least Squares Mean (GLSM) of
Pharmacokinetic Parameters for IN Naloxone at a Dose of 2 mg to IM Naloxone at a
Dose of 0.4 mg with Dose Adjustment to 0.4 mg.

| Parameter | GLSM 2 mg IN | GLSM 0.4 mg IM | GLSM Ratio IM/IN % | 90% Cl of Ratio | p-value |
|---|---|---|---|---|---|
| $AUC_{0-t/D}$ (ng·h/mL) | 0.767 | 1.35 | 56.8 | 50.8-63.4 | <0.001 |
| $AUC_{0-\infty/D}$ (ng·h/mL) | 0.775 | 1.39 | 55.7 | 50.0-62.1 | <0.001 |
| $t_{1/2}$ (h) | 1.18 | 1.19 | 99.3 | 91.3-108 | 0.8963 |

TABLE 7

Statistical Comparison of Comparison of
Geometric Least Squares Mean (GLSM) Pharmacokinetic
Parameters for IN Naloxone at a Dose of 4 mg to IM
Naloxone at a Dose of 0.4 mg with Dose Adjustment to 0.4 mg.

| Parameter | GLSM 4 mg IN | GLSM 0.4 mg IM | GLSM Ratio IM/IN % | 90% Cl of Ratio | p-value |
|---|---|---|---|---|---|
| $C_{max/D}$ (ng/mL) | 0.466 | 0.755 | 61.7 | 50.5-75.5 | <0.001 |
| $t_{max}$ (h) | 0.292 | 0.308 | — | — | 0.418 |
| $AUC_{0-t/D}$ (ng·h/mL) | 0.637 | 1.35 | 47.2 | 42.2-52.7 | <0.001 |
| $AUC_{0-\infty/D}$ (ng·h/mL) | 0.644 | 1.39 | 46.3 | 41.5-51.6 | <0.001 |
| $t_{1/2}$ (h) | 1.22 | 1.19 | 102 | 94.0-111 | 0.651 |

TABLE 8

Time to Prepare the IM and IN Doses for Administration.

| | Time (seconds) | | |
|---|---|---|---|
| | IM Dose | 2 mg IN Dose | 4 mg IN Dose |
| N | 14 | 14 | 14 |
| Mean | 70 | 19 | 23 |
| SD | 10 | 4 | 3 |
| Median | 73 | 19 | 23 |
| Minimum | 50 | 15 | 18 |
| Maximum | 82 | 30 | 28 |

TABLE 9

Estimated IN Dose Delivered (mg).

| | 2 mg Dose Total | 4 mg Dose | | | |
|---|---|---|---|---|---|
| | | First Device | Second Device | Total | All Devices Total |
| N | 14 | 14 | 14 | 14 | 42 |
| Mean | 1.697 | 1.682 | 1.687 | 3.369 | 1.689 |
| SD | 0.097 | 0.156 | 0.092 | 0.193 | 0.116 |
| % CV | 5.7 | 9.3 | 5.4 | 5.7 | 6.9 |
| Median | 1.708 | 1.711 | 1.704 | 3.410 | 1.710 |
| Minimum | 1.481 | 1.315 | 1.506 | 2.898 | 1.315 |
| Maximum | 1.838 | 1.824 | 1.803 | 3.616 | 1.838 |

Example 2: Pharmacokinetics and Safety of
Intranasal Naloxone in Humans (Study 2)

A second study was undertaken to determine the pharmacokinetics (PK) and bioavailability of intranasally-delivered naloxone compared to intramuscularly-injected naloxone.

Objectives. Specifically, the study had several objectives. The first was to determine the pharmacokinetics (i.e., the $C_{max}$, $t_{max}$, $AUC_{0-inf}$ and $AUC_{0-t}$) of 4 intranasal doses—2 mg, 4 mg (2 nostrils), 4 mg (1 nostril), and 8 mg (2 nostrils)—of naloxone compared to a 0.4 mg dose of naloxone administrated IM and to identify an appropriate IN dose that could achieve systemic exposure comparable to an approved parenteral dose. The second was to determine the pharmacokinetics of two different concentrations (20 mg/mL and 40 mg/mL) of IN naloxone. The third was to determine the safety of IN naloxone, including adverse events, vital signs, and clinical laboratory changes, specifically with respect to nasal irritation (erythema, edema, and erosion).

Design. The study was an inpatient open-label, randomized, 5-period, 5-treatment, 5-sequence, crossover study involving approximately 30 healthy volunteers, randomized to have at least 24 subjects who complete all study drug administrations and blood collections for PK assessments. Subjects were assigned to one of the 5 sequences and there were 6 subjects in each. Each subject received 5 naloxone treatments during the 5 dosing periods: a single 2 mg IN dose (one 0.1 mL spray of a 20 mg/mL solution in one nostril), a 4 mg IN dose (one 0.1 mL spray of a 20 mg/mL solution in each nostril), a single 4 mg IN dose (one 0.1 mL spray of a 40 mg/mL solution in one nostril), a single 8 mg IN dose (one 0.1 mL spray of a 40 mg/mL solution in each nostril), and a single 0.4 mg IM dose. Subjects stayed in an inpatient facility for 18 days to complete the entire study and were discharged on the next day after the last dose. Subjects returned for a final follow-up visit 3 to 5 days after discharge.

After obtaining informed consent, subjects were screened for eligibility to participate in the study including medical history, physical examination, clinical chemistry, coagulation markers, hematology, infectious disease serology, urinalysis, urine drug and alcohol toxicology screen, vital signs and ECG.

Inclusion criteria were: men or women 18 to 55 years of age, inclusive; written informed consent; BMI ranging from 18 to 30 kg/m2, inclusive; adequate venous access; no clinically significant concurrent medical conditions; agreement to use a reliable double-barrier method of birth control from the start of screening until one week after completing the study (oral contraceptives are prohibited); and agreement not to ingest alcohol, drinks containing xanthine >500 mg/day, or grapefruit/grapefruit juice, or participate in strenuous exercise 72 hours prior to admission through the last blood draw of the study.

Exclusion criteria were: any IN conditions including abnormal nasal anatomy, nasal symptoms (i.e., blocked and/or runny nose, nasal polyps, etc.), or having a product sprayed into the nasal cavity prior to drug administration; taking prescribed or over-the-counter medications, dietary supplements, herbal products, vitamins, or recent use of opioid analgesics for pain relief (within 14 days of last use of any of these products); positive urine drug test for alcohol, opioids, cocaine, amphetamine, methamphetamine, benzodiazepines, tetrahydrocannabinol (THC), barbiturates, or methadone at screening or admission; previous or current opioid, alcohol, or other drug dependence (excluding nicotine and caffeine), based on medical history; subject consumes greater than 20 cigarettes per day on average, in the month prior to screening, or would be unable to abstain from smoking (or use of any nicotine-containing substance) for at least one hour prior to and 2 hours after naloxone dosing; on standard 12-lead ECG, a QTcF interval >440 msec for males and >450 msec for females; significant acute or chronic medical disease in the judgment of the investigator; a likely need for concomitant treatment medication during the study; donated or received blood or underwent plasma or platelet apheresis within the 60 days prior to the day before study commencement; female who is pregnant, breast feeding, or plans to become pregnant during the study period or within one week after naloxone administration; positive test for hepatitis B surface antigen (HBsAg), hepatitis C virus antibody (HCVAb) or human immunodeficiency virus antibody (HIVAb) at screening; and current or recent (within 7 days prior to screening) upper respiratory tract infection.

Naloxone for IM injection manufactured by Hospira was obtained from a licensed distributor at a concentration of 0.4 mg/mL and was given IM at a dose of 0.4 mg in 1.0 mL with a 23-g needle as a single injection in the gluteus maximus muscle. Naloxone for IN administration was obtained from Lightlake Therapeutics, Inc., London, United Kingdom at two concentrations of 20 mg/mL and 40 mg/mL, and was given as doses of 2 mg (one 0.1 mL spray of the 20 mg/mL formulation in one nostril), 4 mg (two 0.1 mL sprays of the 20 mg/mL formulation in two nostrils), 4 mg (one 0.1 mL spray of the 40 mg/mL formulation in one nostril) and 8 mg (two 0.1 mL sprays of the 40 mg/mL formulation in two nostril). IN naloxone was administered using an Aptar single dose device with the subject in a fully supine position. Subjects were to be instructed to not breathe through the nose when the IN dose of naloxone was administered.

On the day after clinic admission, subjects were administered study drug in randomized order with a 4-day washout period between doses until all 5 treatments were administered. Blood was collected for naloxone PK prior to dosing and approximately 2.5, 5, 10, 15, 20, 30, 45, 60, 120, 180, 240, 300, 360, 480 and 720 minutes after the start of study drug administration, into sodium heparin containing tubes. On days of study drug administration, a 12-lead ECG was performed approximately 60 minutes prior to dosing and at approximately 60 and 480 minutes post-dose. Vital signs were measured pre-dose and approximately 30, 60, 120, and 480 minutes post-dose. On dosing days, the order of assessments were ECG, vital signs, then PK blood collection when scheduled at the same nominal times. The target time of the PK blood collection was considered the most important, and if the collection was more than ±1 minute from the scheduled time for the first 60 minutes of collections or more than ±5 minutes for the scheduled time points thereafter, this was considered a protocol deviation. ECG and vital signs were collected within the 10 minute period before the nominal time of blood collections. At screening, admission, discharge, and follow-up, ECG and vital signs were checked once per day. Vital signs were also checked once on the day after naloxone administration. Clinical laboratory measurements were repeated after the last PK blood draw prior to clinic discharge. Adverse events were assessed by spontaneous reports by subjects, by examination of the nasal mucosa, by measuring vital signs, ECG, and clinical laboratory parameters.

Figure 3A:
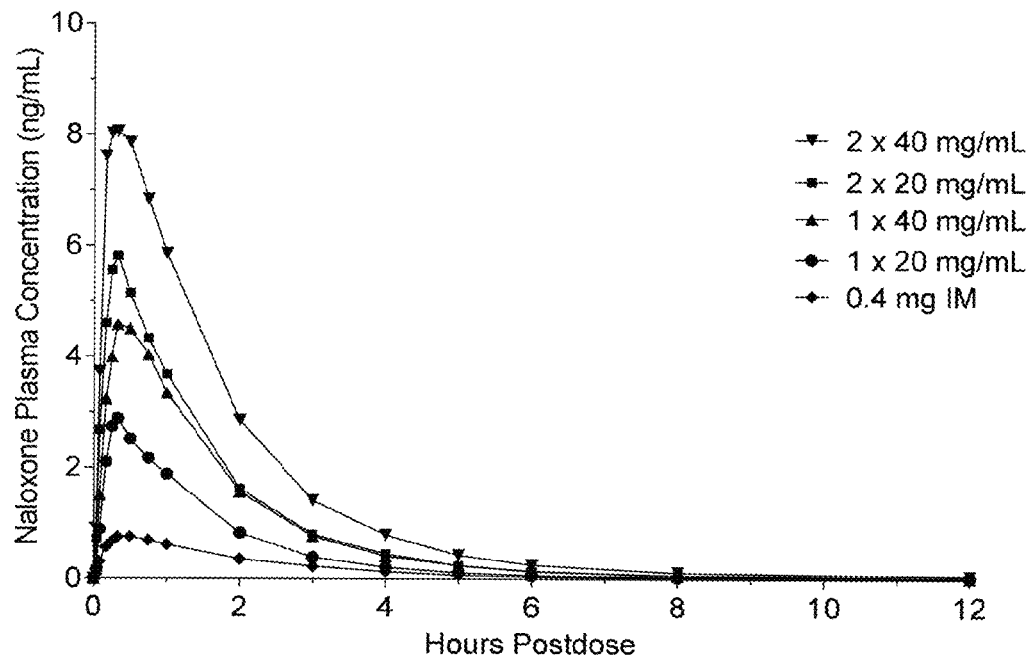
FIGS. 3A and 3B show the mean naloxone plasma concentration following single intranasal administrations (FIG. 3A) and intramuscular injections (FIG. 3B) of naloxone to healthy subjects (N=28) over a twelve-hour period.
Figure 3B:
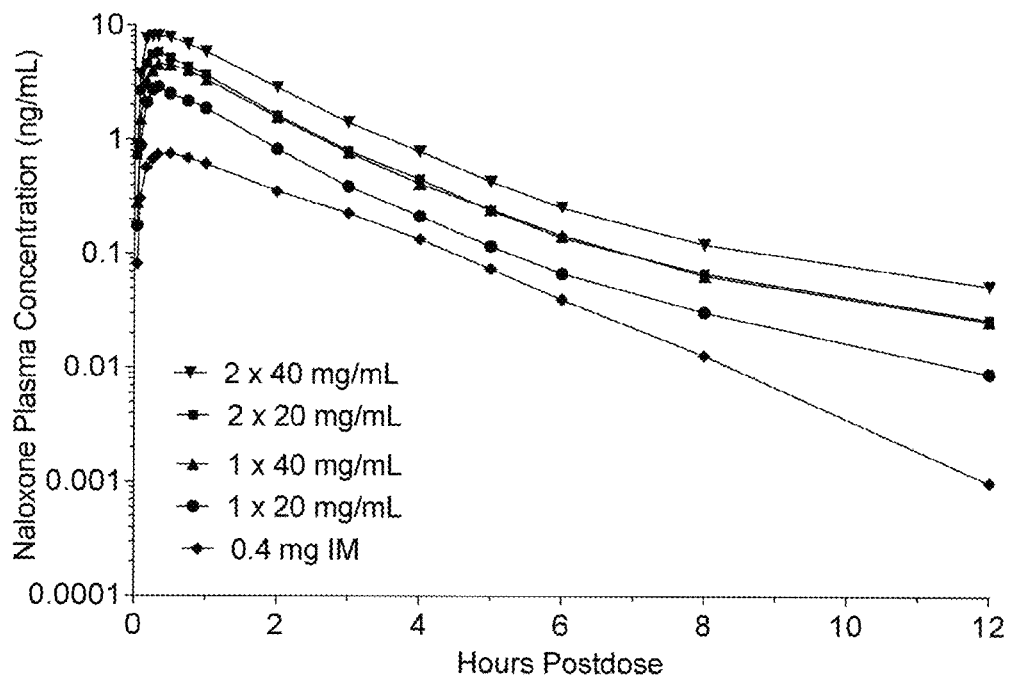
Figure 4A:
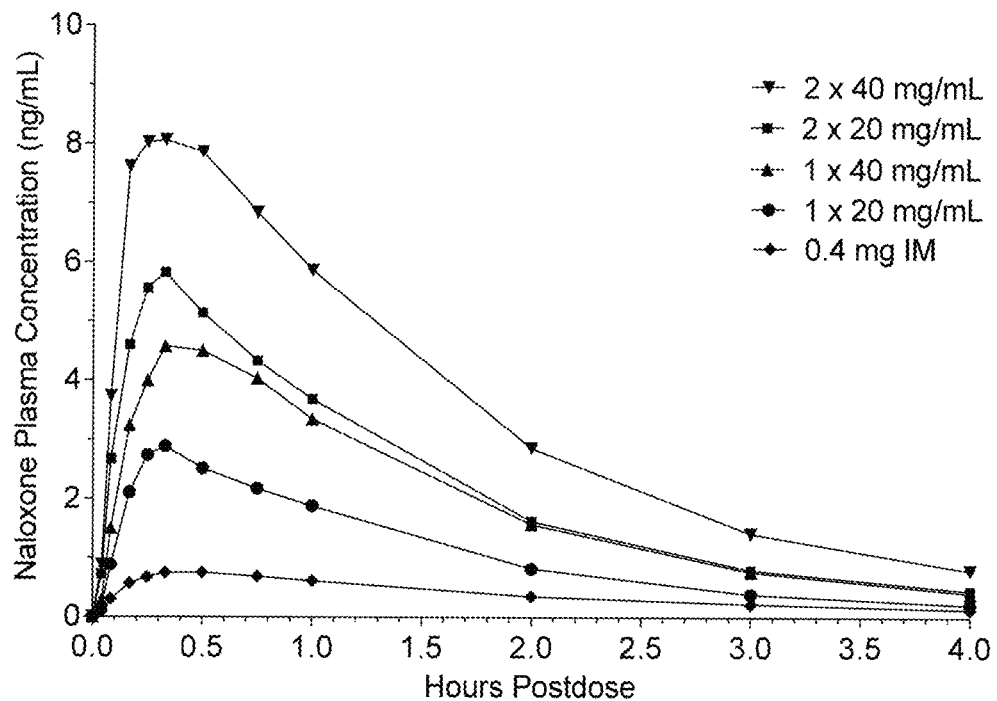
FIGS. 4A and 4B show the mean naloxone plasma concentration following single intranasal administrations (FIG. 4A) and intramuscular injections (FIG. 4B) of naloxone to healthy subjects (N=28) over a four-hour period.
Figure 4B:
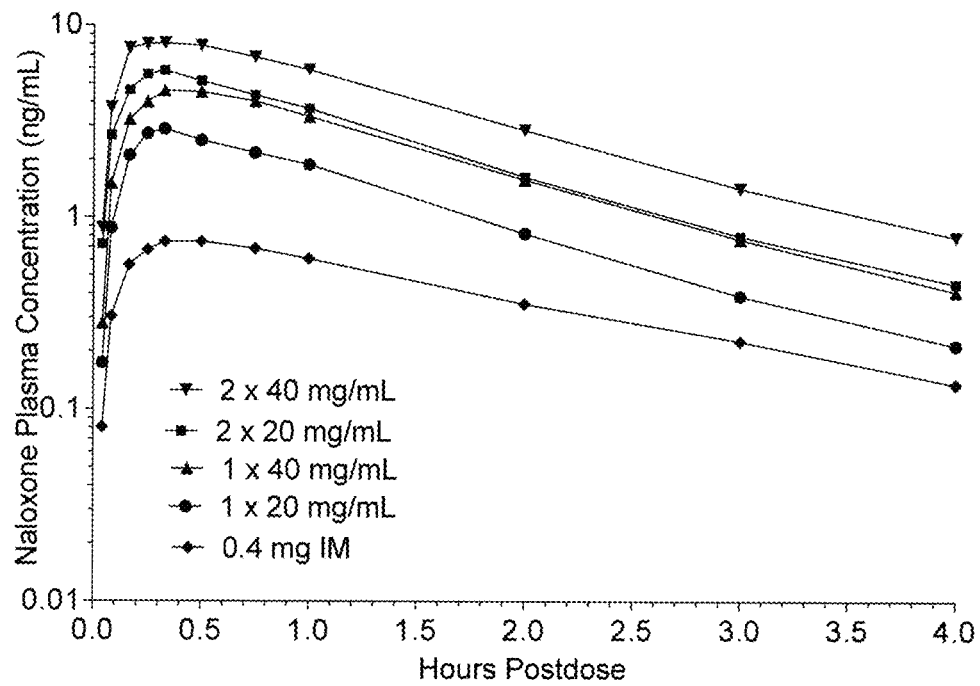
Figure 5A:
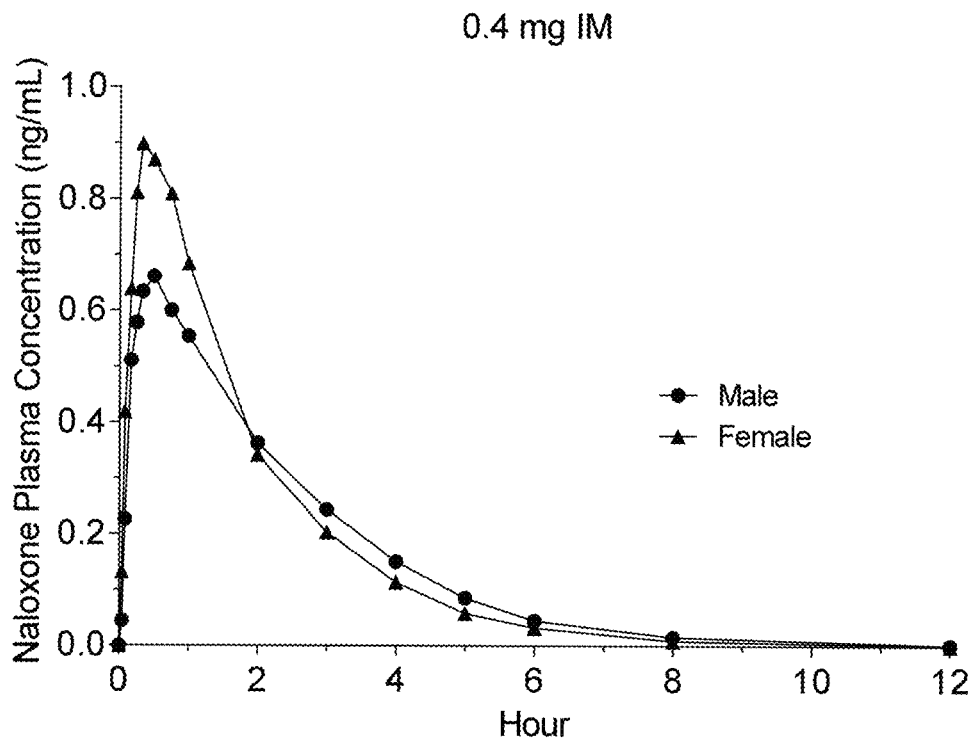
FIGS. 5A and 5B show the mean naloxone plasma concentration following intramuscular injection of 0.4 mg naloxone (FIG. 5A, top) and one spray of 20 mg/mL (i.e., 2% w/v) naloxone (FIG. 5B, bottom) to healthy male (N=16) and female (N=12) subjects over a twelve-hour period.
Figure 5B:
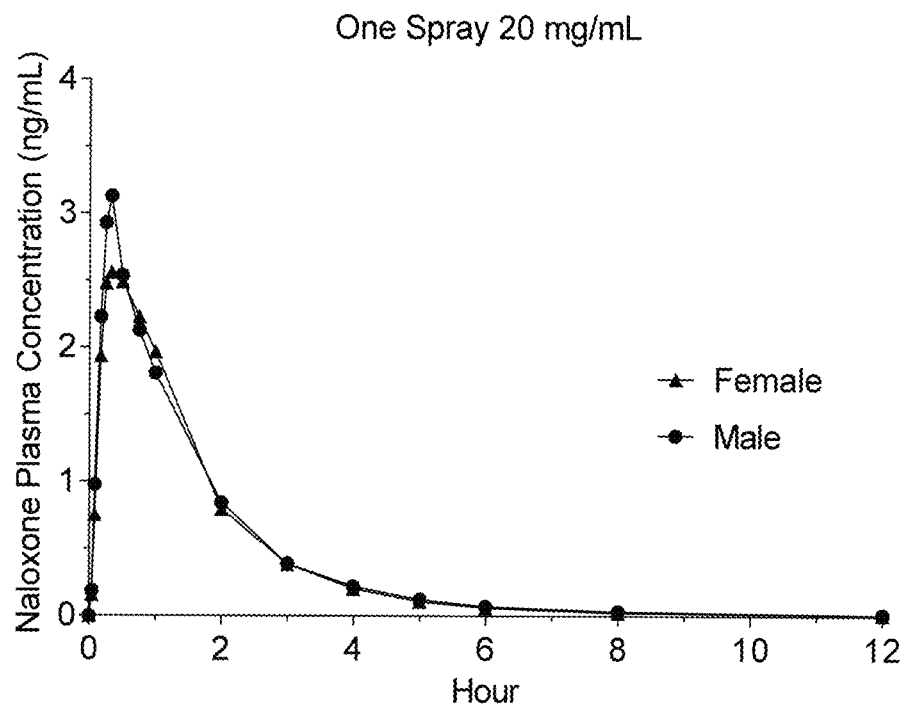
Figure 6A:
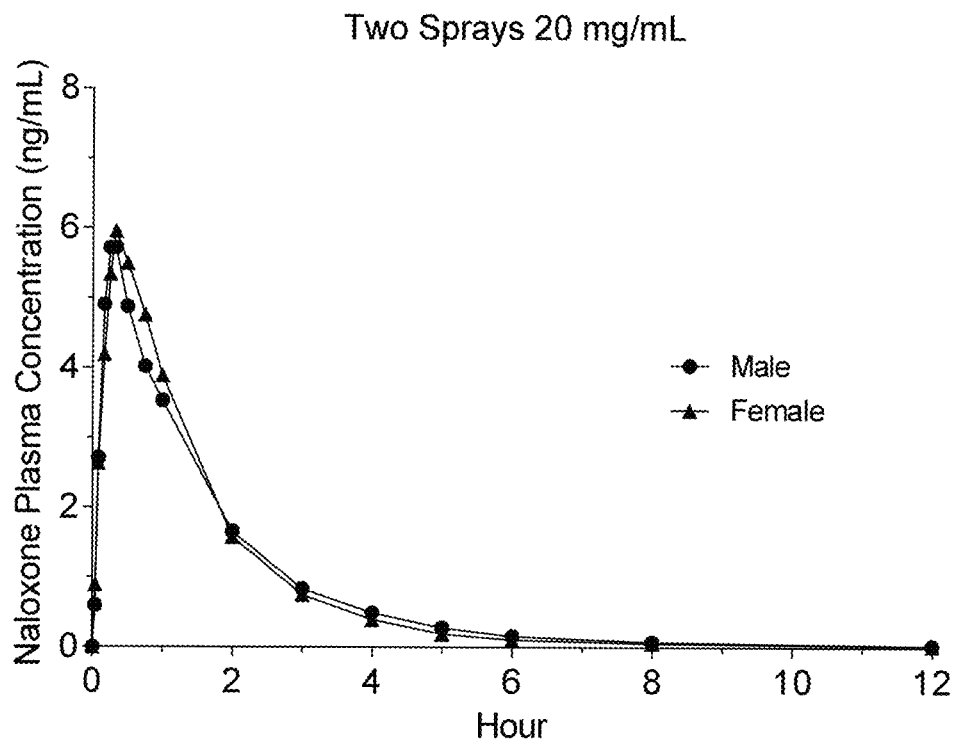
FIGS. 6A and 6B show the mean naloxone plasma concentration following two sprays of 20 mg/mL (i.e., 2% w/v, FIG. 6A, top) and one spray of 40 mg/mL (i.e., 4% w/v, FIG. 6B, bottom) to healthy male (N=16) and female (N=12) subjects over a twelve-hour period.
Figure 6B:
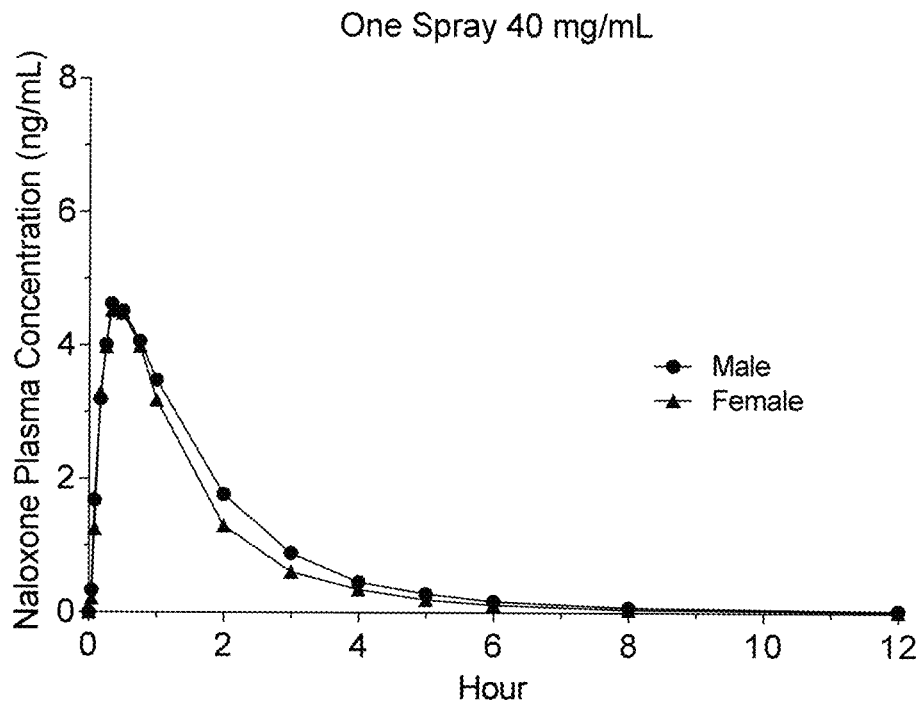
Figure 7:
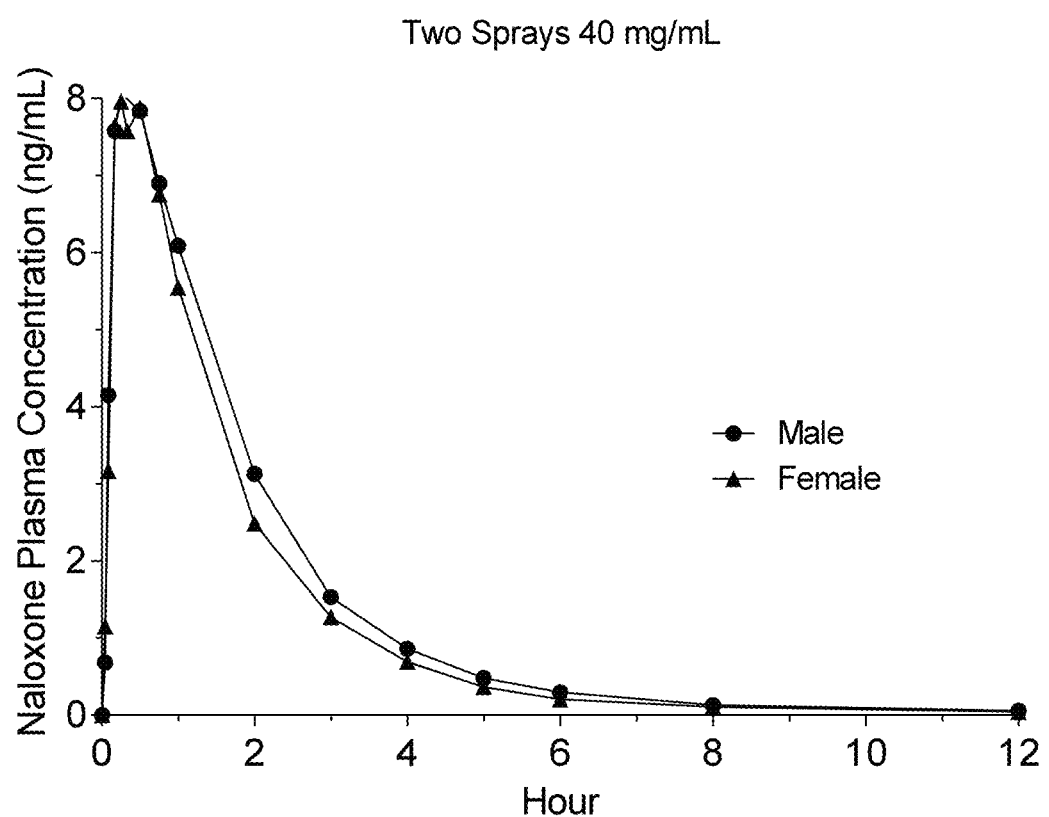
FIG. 7 shows the mean naloxone plasma concentration following two sprays of 40 mg/mL (i.e., 4% w/v) to healthy male (N=16) and female (N=12) subjects over a twelve-hour period.

Results are shown below in Table 10, which sets forth the mean from 28 healthy subjects (and SD, in parentheses) plasma concentrations of naloxone following single intranasal administrations and an intramuscular injection, and in FIGS. 3 and 4.

TABLE 10

Mean results from 28 healthy subjects.

| Time (min) | One Spray - 2 mg 2% (w/v) IN | Two Sprays - 4 mg 2% (w/v) IN | One Spray - 4 mg 4% (w/v) IN | Two Sprays - 8 mg 4% (w/v) IN | 0.4 mg IM |
|---|---|---|---|---|---|
| 0 | 0.000 (0.000) | 0.000 (0.000) | 0.000 (0.000) | 0.000 (0.000) | 0.000 (0.000) |
| 2.5 | 0.175 (0.219) | 0.725 (0.856) | 0.280 (0.423) | 0.880 (1.21) | 0.081 (0.135) |
| 5 | 0.882 (0.758) | 2.68 (2.65) | 1.50 (1.76) | 3.73 (4.02) | 0.305 (0.336) |
| 10 | 2.11 (1.33) | 4.60 (2.59) | 3.24 (2.21) | 7.61 (5.28) | 0.566 (0.318) |
| 15 | 2.74 (1.07) | 5.56 (2.20) | 4.00 (2.24) | 8.02 (3.60) | 0.678 (0.312) |
| 20 | 2.89 (1.14) | 5.82 (1.74) | 4.57 (2.30) | 8.06 (2.56) | 0.747 (0.271) |
| 30 | 2.52 (0.810) | 5.15 (1.70) | 4.50 (1.93) | 7.89 (1.95) | 0.750 (0.190) |
| 45 | 2.17 (0.636) | 4.33 (1.16) | 4.03 (1.57) | 6.84 (1.69) | 0.689 (0.171) |
| 60 | 1.88 (0.574) | 3.69 (0.887) | 3.35 (1.17) | 5.86 (1.40) | 0.610 (0.143) |
| 120 | 0.823 (0.335) | 1.63 (0.626) | 1.57 (0.773) | 2.86 (0.927) | 0.354 (0.107) |
| 180 | 0.390 (0.146) | 0.800 (0.253) | 0.771 (0.412) | 1.42 (0.487) | 0.227 (0.082) |
| 240 | 0.215 (0.100) | 0.452 (0.225) | 0.412 (0.215) | 0.791 (0.275) | 0.135 (0.058) |
| 300 | 0.117 (0.051) | 0.243 (0.123) | 0.246 (0.143) | 0.431 (0.166) | 0.074 (0.047) |
| 360 | 0.068 (0.030) | 0.139 (0.067) | 0.146 (0.081) | 0.257 (0.104) | 0.040 (0.022) |
| 480 | 0.031 (0.014) | 0.068 (0.033) | 0.065 (0.038) | 0.122 (0.052) | 0.013 (0.015) |
| 720 | 0.009 (0.009) | 0.027 (0.013) | 0.026 (0.019) | 0.053 (0.025) | 0.001 (0.003) |

For pharmacokinetic analysis, plasma was separated from whole blood and stored frozen at ≤−20° C. until assayed. Naloxone plasma concentrations were determined by liquid chromatography with tandem mass spectrometry. Conjugated naloxone plasma concentrations may also be determined. Non-compartmental PK parameters including $C_{max}$, $t_{max}$, $AUC_{0-inf}$, $AUC_{0-t}$, $t_{1/2}$, $\lambda_z$, and apparent clearance (CL/F) were determined. Pharmacokinetic parameters ($C_{max}$, $t_{max}$, and AUCs) for IN naloxone were compared with those for IM naloxone. $t_{max}$ was from the time of administration (spraying into the nasal cavity or IM injection). Dose adjusted values for AUCs and $C_{max}$ were then calculated, and the relative extent of intranasal absorption (IN versus IM) estimated from the dose-corrected AUCs. Within an ANOVA framework, comparisons of ln-transformed PK parameters ($C_{max}$ and AUC) for intranasal versus IM naloxone treatments were performed. The 90% confidence interval for the ratio (IN/IM) of the geometric least squares means of AUC and $C_{max}$ parameters were constructed for comparison of each treatment with IM naloxone. These 90%

CIs were obtained by exponentiation of the 90% confidence intervals for the difference between the least squares means based upon an ln scale.

Results are shown below in Table 11, which sets forth the mean plasma PK parameters from 28 healthy subjects (and % CV, in parentheses) of naloxone following single intranasal administrations and an intramuscular injection, and in Table 12, which sets forth the same PK parameters split between the 12 female and 16 male healthy subjects. Results from a replication study conducted according to substantially the same experimental protocols are shown in Table 11 below.

TABLE 11

Mean plasma PK parameters from 28 healthy subjects.

| Parameter (units) | One Spray- 2 mg 2% (w/v) IN | Two Sprays- 4 mg 2% (w/v) IN | One Spray- 4 mg 4% (w/v) IN | Two Sprays- 8 mg 4% (w/v) IN | 0.4 mg IM |
|---|---|---|---|---|---|
| $C_{max}$ (ng/ml) | 3.11 (36.3) | 6.63 (34.2) | 5.34 (44.1) | 10.3 (38.8) | 0.906 (31.5) |
| $C_{max}$ per mg (ng/mL) | 1.56 (36.3) | 1.66 (34.2) | 1.34 (44.1) | 1.29 (38.8) | 2.26 (31.5) |
| $t_{max}$ (h)$^a$ (median, range) | 0.33 (0.25, 1.00) | 0.33 (0.08, 0.50) | 0.50 (0.17, 1.00), | 0.33 (0.17, 1.00), | 0.42 (0.08,) 2.00) |
| $AUC_t$ (ng·mL/h) | 4.81 (30.3) | 9.82 (27.3) | 8.78 (37.4) | 15.9 (23.6) | 1.79 (23.5) |
| $AUC_{inf}$ (ng·mL/h) | 4.86 (30.1) | 9.91 (27.1) | 8.87 (37.2) | 16.1 (23.3) | 1.83 (23.0) |
| $AUC_{inf}$ per mg (ng·mL/h) | 2.43 (30.1) | 2.48 (27.1) | 2.22 (37.2) | 2.01 (23.3) | 4.57 (23.0) |
| Lambda z (hr$^{-1}$)$^b$ | 0.3685 | 0.2973 | 0.3182 | 0.3217 | 0.5534 |
| Half-life (h)$^b$ | 1.70 | 2.09 | 2.00 | 1.91 | 1.19 |
| AUC % Extrapolate | 1.09 (41.9) | 1.01 (53.9) | 1.06 (52.5) | 1.04 (78.1) | 2.32 (54.1) |
| CL/F (L/h) | 441 (24.5) | 426 (22.3) | 502 (31.2) | 521 (21.7) | 230 (22.4) |
| Relative BA (%) vs. IM | 53.8 (22.2) | 55.3 (22.2) | 49.2 (30.6) | 45.3 (25.1) | 100 |

TABLE 12

Mean plasma PK parameters from 28 healthy subjects.

| Parameter (units) | One 2% (w/v) IN Female | One 2% (w/v) IN Male | Two 2% (w/v) IN Female | Two 2% (w/v) IN Male | One 4% (w/v) IN Female | One 4% (w/v) IN Male | Two 4% (w/v) IN Female | Two 4% (w/v) IN Male | 0.4 mg IM Female | 0.4 mg IM Male |
|---|---|---|---|---|---|---|---|---|---|---|
| $C_{max}$ (ng/ml) | 2.79 | 3.35 | 6.62 | 6.64 | 5.12 | 5.51 | 9.52 | 10.9 | 1.06 | 0.792 |
| $C_{max}$ per mg (ng/mL) | 1.39 | 1.68 | 1.66 | 1.66 | 1.28 | 1.38 | 1.19 | 1.36 | 2.64 | 1.98 |
| $t_{max}$ (h)$^a$ | 0.33 | 0.33 | 0.33 | 0.25 | 0.50 | 0.50 | 0.29 | 0.42 | 0.33 | 0.50 |
| $AUC_t$ (ng·mL/h) | 4.73 | 4.87 | 9.81 | 9.82 | 7.98 | 9.38 | 14.8 | 16.8 | 1.83 | 1.75 |
| $AUC_{inf}$ (ng·mL/h) | 4.78 | 4.93 | 9.91 | 9.92 | 8.06 | 9.48 | 15.0 | 16.9 | 1.88 | 1.79 |
| $AUC_{inf}$ per mg (ng·mL/h) | 2.39 | 2.46 | 2.48 | 2.48 | 2.01 | 2.37 | 1.87 | 2.12 | 4.69 | 4.47 |
| Lambda z (hr$^{-1}$)$^b$ | 0.3978 | 0.3492 | 0.2796 | 0.3122 | 0.2946 | 0.3386 | 0.2994 | 0.3407 | 0.6140 | 0.5152 |
| Half-life (h)$^b$ | 1.58 | 1.80 | 2.18 | 2.03 | 2.12 | 1.93 | 1.90 | 1.91 | 1.08 | 1.28 |
| AUC % Extrapolate | 0.971 | 1.19 | 0.986 | 1.02 | 0.970 | 1.12 | 1.12 | 0.992 | 2.31 | 2.32 |
| CL/F (L/h) | 449 | 434 | 419 | 431 | 555 | 462 | 558 | 494 | 222 | 236 |

In the tables above, the notation a indicates median (range) is disclosed, and the notation b indicates harmonic mean is disclosed.

TABLE 13

Geometric mean pharmacokinetic parameters (CV%) following intranasal spray or intramuscular injection.

| Parameter | One Spray 2% (w/v) IN | Two Sprays 2% (w/v) IN | One Spray 4% (w/v) IN | Two Sprays 4% (w/v) IN | One Injection 0.4 mgIM |
|---|---|---|---|---|---|
| λz (1/h) | 0.382 (34.9) | 0.310 (34.5) | 0.334 (29.5) | 0.330 (32.4) | 0.557 (25.9) |
| t½ (h) | 1.81 (34.9) | 2.23 (34.5) | 2.08 (29.5) | 2.10 (32.4) | 1.24 (25.9) |

TABLE 13-continued

Geometric mean pharmacokinetic parameters (CV%) following intranasal spray or intramuscular injection.

| Parameter | One Spray 2% (w/v) IN | Two Sprays 2% (w/v) IN | One Spray 4% (w/v) IN | Two Sprays 4% (w/v) IN | One Injection 0.4 mgIM |
|---|---|---|---|---|---|
| $t_{max}$ (h)* | 0.33 (0.25, 1.00) | 0.33 (0.17, 0.57) | 0.50 (0.17, 1.00) | 0.33 (0.17, 1.00) | 0.38 (0.08, 2.05) |
| $C_{max}$ (ng/mL) | 2.92 (34.3) | 6.20 (31.9) | 4.83 (43.1) | 9.70 (36.0) | 0.877 (30.5) |
| $C_{max}$/Dose (ng/mL/mg) | 1.46 (34.3) | 1.55 (31.9) | 1.21 (43.1) | 1.21 (36.0) | 2.19 (30.5) |
| $AUC_{0-t}$ (h * ng/mL) | 4.51 (27.2) | 9.32 (24.0) | 7.87 (37.4) | 15.3 (23.0) | 1.72 (22.9) |
| $AUC_{0-t}$/Dose (h * ng/mL/mg) | 2.25 (27.2) | 2.33 (24.0) | 1.97 (37.4) | 1.91 (23.0) | 4.29 (22.9) |
| $AUC_{0-\infty}$ (h * ng/mL) | 4.56 (26.9) | 9.43 (24.0) | 7.95 (37.3) | 15.5 (22.7) | 1.76 (22.6) |
| $AUC_{0-\infty}$/Dose (h * ng/mL/mg) | 2.28 (26.9) | 2.36 (24.0) | 1.99 (37.3) | 1.93 (22.7) | 4.40 (22.6) |
| AUC % extrapolated | 1.06 (56.5) | 0.935 (60.1) | 0.965 (53.5) | 0.963 (69.3) | 2.18 (57.5) |
| CL/F (L/h) | 438 (26.9) | 424 (24.0) | 503 (37.3) | 518 (22.7) | 227 (22.6) |
| Relative BA (%) vs. IM | 51.9 (21.7) | 53.6 (22.5) | 46.7 (31.4) | 43.9 (23.8) | 100 |
| $C_{max}$/Dose Ratio (IN vs. IM (%) | 66.6 (41.4) | 70.7 (37.7) | 56.6 (47.5) | 55.3 (41.4) | 100 |

*Values in parentheses indicate minimum and maximum, not CV %.

AEs were coded using the MedDRA, v. 19 preferred terms and grouped by system, organ, class (SOC) designation. Separate summaries will be provided for the 5 study periods: after the administration of each dose of study drug up until the time of the next dose of study drug or clinic discharge. Listings of each individual AE including start date, stop date, severity, relationship, outcome, and duration were provided. Results are given below in Tables 14 and 15. Table 14 shows the events related to nasal irritation—erythema, edema, other, and total—observed in the nasally-treated group. Nasal irritation did not appear to be positively related to the dose of naloxone given.

TABLE 14

Events related to nasal irritation.

| Treatment | Erythema | Edema | Other | Total |
|---|---|---|---|---|
| 2 mg (2% w/v, one spray) | 4 | 2 | 1 | 7 |
| 4 mg (2% w/v, two sprays) | 1 | 0 | 0 | 1 |
| 4 mg (4% w/v, one spray) | 1 | 2 | 0 | 3 |
| 8 mg (4% w/v, two sprays) | 0 | 1 | 0 | 1 |

Table 15 shows additional events related to administration either nasally or intramuscularly. Overall, few adverse events were reported.

TABLE 15

Naloxone intranasal adverse events.

| 0.4 mg Intramuscular Dose | |
|---|---|
| Dizziness | 1 |
| Headache | 1 |
| Nausea | 1 |
| 2 mg (2% w/v, one spray) | |
| Nasal Pain | 1 |
| 8 mg (4% w/v, two sprays) | |
| Headache | 1 |

Additionally, vital signs, ECG, and clinical laboratory parameters did not reveal any clinically noteworthy changes after naloxone administration. There was no evidence of QTcF prolongation.

Example 3: Naloxone Nasal Spray Formulations and Stability

Naloxone has been formulated as a disposable Luer-Jet Luer-lock pre-filled injectable syringe. Although not approved as a combined product, this formulation is sometimes combined with an nasal atomizer kit product, comprising 1 mg/ml naloxone hydrochloride as an active agent, 8.35 mg/ml NaCl as an isotonicity agent, HCl q.s. to target pH, and purified water q.s. to 2.0 ml. Benzalkonium chloride may be added as a preservative and supports the stability of a multi-dose product. Such syringes, while functional, can be difficult to use by untrained personnel, and deliver a large volume of solution.

Examples of a 10 mg/mL formulation are given below in Table 16.

TABLE 16

10 mg/mL naloxone intranasal formulation.

| Ingredient | Quantity per unit | Function |
|---|---|---|
| Naloxone hydrochloride | 10 mg/ml | Active ingredient |
| Sodium chloride | 7.4 mg/ml | Isotonicity agent |
| Hydrochloric acid | q.s. to target pH | Acidifying agent |
| Benzalkonium chloride | 0.1 mg/ml | Preservative/Enhancer |
| Purified water | q.s. | Solvent |

Literature data has indicated that naloxone is sensitive to environmental factors, such as air, light and colors in certain vials, which may induce a risk for degradation. Consequently disodium edetate was added to the above formulation.

Pharmaceutical compositions comprising naloxone hydrochloride (1, 2, or 4% w/v, i.e., 10, 20, or 40 mg/mL) were stored at 25° C. and 60% relative humidity or 40° C. and 75% relative humidity in upright clear glass vials (200

μL) stoppered with a black plunger. The 2% and 4% (w/v) compositions were also tested at 40° C. and 75% relative humidity. Vials of the 1% (w/v) compositions were either nude (Batch 1), or mounted in the Pfeiffer BiDose device (Batch 2). In addition to naloxone hydrochloride, the pharmaceutical compositions further comprised water, benzalkonium chloride, and disodium edetate. The vials were assayed at 0, 1, 3, 6, 9, and/or 12 months for naloxone content using a high-pressure liquid chromatography method. Naloxone was analyzed at each stability station using a validated (as per the International Conference on Harmonisation Guidance Q2(R1) (ICH Q2(R1)) reverse phase high pressure liquid chromatography (RP-HPLC) method and ultraviolet (UV) detection. The chromatographic system used a C6-phenyl chromatography column at a flow rate of 0.8 mL/min and a column temperature of 40° C. The injection volume was 10 μL; the gradient A/B 60/40 to 40/60; the mobile phase A 25 mM sodium phosphate at pH 6.8; the mobile phase B: 100% acetonitrile. The ultra-violet detector wavelength was 229 nm and the runtime was 20 min. The assay data in Table 18 were generated over the course of development. The 25° C./60% RH experiments were conducted with clinical batches and the 40° C./75% RH experiments used later manufactured registration or stability batches. It is evident from the results of the study, reported as a percentage of the label claim in Tables 17 and 18 below, that these pharmaceutical compositions are storage-stable for at least 9-12 months at 25° C. and 60% relative humidity.

TABLE 17

1% (w/v) Naloxone storage stability.

| Batch | Time (months) | | | | |
|---|---|---|---|---|---|
| | 0 | 3 | 6 | 9 | 12 |
| 1 | 99.3 | 100.1 | 100.8 | 101.2 | 97.9 |
| 2 | 99.5 | 102.8 | 99.4 | 98.6 | ND |

TABLE 18

2% and 4% (w/v) Naloxone storage stability.

| Temp. & relative humidity | Naloxone conc. (% w/v) | Naloxone stability (assay % of target amount) | | | | |
|---|---|---|---|---|---|---|
| | | Initial | 1 month | 3 month | 6 month | 12 month |
| 40° C. 75% RH | 2 | 103.5 | 103 | 99.8 | 100.4 | |
| | 4 | 105.8 | 103.4 | 102 | 100.7 | |

TABLE 18-continued

2% and 4% (w/v) Naloxone storage stability.

| Temp. & relative humidity | Naloxone conc. (% w/v) | Naloxone stability (assay % of target amount) | | | | |
|---|---|---|---|---|---|---|
| | | Initial | 1 month | 3 month | 6 month | 12 month |
| 25° C. 60% RH | 2 | 101.2 | | 104.8 | 102.4 | 101.6 |
| | 4 | 101.8 | | 101.3 | 102.9 | 101.9 |

Examples with the 20 and 40 mg/mL formulations are given below in Table 19, along with an example of permitted variation as part of the total formulation. Subsequent modifications were able to reduce the dose-to-dose variation further still, even after six- to twelve-month storage (Table 20).

TABLE 19

Twelve month naloxone storage stability.

| | Concentration | | | | |
|---|---|---|---|---|---|
| | 20 mg/ml | | 40 mg/ml | | |
| Component | Quantity per ml | Quantity per unit dose (100 μl) | Quantity per ml | Quantity per unit dose (100 μl) | Product Variation |
| Naloxone HCl dihydrate (corresponding to naloxone HCl) | 22.0 mg (20.0 mg) | 2.2 mg (2.0 mg) | 44.0 mg (40.0 mg) | 4.4 mg (4.0 mg) | 90.0-110.0 |
| Benzalkonium chloride | 0.1 mg | 0.01 mg | 0.1 mg | 0.01 mg | 90.0-110.0 |
| Disodium edetate | 2.0 mg | 0.2 mg | 2.0 mg | 0.2 mg | 80.0-120.0 |
| Sodium chloride | 7.4 mg | 0.74 mg | 7.4 mg | 0.74 mg | |
| Hydrochloric acid, dilute | Adjust to pH 4.5 | Adjust to pH 4.5 | Adjust to pH 4.5 | Adjust to pH 4.5 | pH 3.5-5.5 |
| Purified water | q.s. ad 1.0 ml | q.s. ad 100 μl | q.s. ad 1.0 ml | q.s. ad 100 μl | |

TABLE 20

Six month naloxone storage stability.

| | | Sample age | | | |
|---|---|---|---|---|---|
| | | Initial (% TD) | 1 month (% TD) | 3 month (% TD) | 6 month (% TD) |
| 2% (w/v) Stored upright at 25° C., 60% relative humidity | Uniform dose delivery | 1) 102.0% | 1) 99.9% | 1) 99.5% | 1) 101.7% |
| | | 2) 96.7% | 2) 103.7% | 2) 101.6% | 2) 100.4% |
| | | 3) 101.6% | 3) 102.7% | 3) 98.5% | 3) 99.8% |
| | | 4) 101.7% | 4) 101.7% | 4) 100.0% | 4) 97.2% |
| | | 5) 98.5% | 5) 95.8% | 5) 99.4% | 5) 100.5% |
| | | 6) 101.0% | 6) 98.6% | 6) 96.6% | 6) 96.8% |
| | | 7) 100.6% | 7) 98.9% | 7) 102.5% | 7) 98.3% |
| | | 8) 101.4% | 8) 98.7% | 8) 97.0% | 8) 102.0% |
| | | 9) 100.0% | 9) 99.2% | 9) 102.6% | 9) 96.9% |
| | | 10) 99.2% | 10) 100.5% | 10) 100.6% | 10) 102.4% |

TABLE 20-continued

Six month naloxone storage stability.

| | | Sample age | | | |
|---|---|---|---|---|---|
| | Avg. | 100.3% | 100.1% | 99.9% | 99.7% |
| | Mean pump delivery | 101.3 mg | 101.0 mg | 100.8 mg | 100.6 mg |
| | 3 cm mean ovality ratio | 1.180 | 1.230 | 1.522 | 1.516 |
| | 6 cm mean ovality ratio | 1.383 | 1.386 | 1.687 | 1.764 |
| | 3 cm spray mean Dv(90) | 65.40 μm | 55.84 μm | 73.07 μm | 69.13 μm |
| | 3 cm spray mean span | 1.429 | 1.300 | 1.572 | 1.447 |
| | 3 cm spray mean %<10 μm | 1.342% | 1.982% | 1.637% | 0.269% |
| | 6 cm spray mean Dv(90) | 62.01 μm | 65.60 μm | 66.95 μm | 64.81 μm |
| | 6 cm spray mean span | 1.103 | 1.087 | 1.210 | 1.155 |
| | 6 cm spray mean %<10 μm | 1.714% | 1.799% | 1.625% | 1.634% |
| 2% (w/v) Stored inverted at 25° C. 60% relative humidity | Avg. %TD of ten actuations | 100.3% | 99.9% | 98.3% | 100.0% |
| | Mean pump delivery | 101.3 mg | 100.8 mg | 99.2 mg | 100.9 mg |
| | 3 cm mean ovality ratio | 1.180 | 1.210 | 1.214 | 1.159 |
| | 6 cm mean ovality ratio | 1.383 | 1.421 | 1.351 | 1.442 |
| | 3 cm spray mean Dv(90) | 65.40 μm | 69.60 μm | 68.33 μm | 70.05 μm |
| | 3 cm spray mean span | 1.429 | 1.473 | 1.509 | 1.491 |
| | 3 cm spray mean %<10 μm | 1.342% | 1.543% | 1.637% | 1.218% |
| | 6 cm spray mean Dv(90) | 62.01 μm | 62.96 μm | 65.51 μm | 69.02 μm |
| | 6 cm spray mean span | 1.103 | 1.133 | 1.217 | 1.171 |
| | 6 cm spray mean %<10 μm | 1.714% | 1.828% | 1.400% | 1.752% |

| | | Initial (% TD) | 6 month (% TD) | 12 month (% TD) |
|---|---|---|---|---|
| 4% (w/v) Stored upright at 25° C., 60% relative humidity | Uniform dose delivery | 1) 100.2% | 1) 98.6% | 1) 99.4% |
| | | 2) 97.3% | 2) 98.2% | 2) 107.1% |
| | | 3) 96.1% | 3) 98.1% | 3) 103.3% |
| | | 4) 99.4% | 4) 101.5% | 4) 98.6% |
| | | 5) 98.8% | 5) 96.4% | 5) 99.1% |
| | | 6) 98.3% | 6) 98.0% | 6) 103.6% |
| | | 7) 100.2% | 7) 97.7% | 7) 102.7% |
| | | 8) 101.3% | 8) 97.9% | 8) 100.8% |
| | | 9) 99.8% | 9) 97.3% | 9) 101.5% |
| | | 10) 99.7% | 10) 98.4% | 10) 100.1% |
| | Avg. | 99.11% | 98.21% | 101.62% |
| | Mean pump delivery | 100.2 mg | | 103.1 mg |
| | 3 cm mean ovality ratio | | 1.511 | |
| | 6 cm mean ovality ratio | | 1.435 | |
| | 3 cm spray mean Dv(90) | | 90.56 μm | |
| | 3 cm spray mean span | | 1.680 | |
| | 3 cm spray mean %<10 μm | | 1.135% | |
| | 6 cm spray mean Dv(90) | | 66.27 μm | |
| | 6 cm spray mean span | | 1.137 | |
| | 6 cm spray mean %<10 μm | | 1.825% | |

The naloxone hydrochloride nasal spray above is an aqueous solution which may be presented in a Type I glass vial closed with a chlorobutyl rubber plunger which in turn is mounted into a unit-dose nasal spray device (such as an Aptar UDS liquid UnitDose device). The solution should be a clear and colorless or slightly yellow liquid. In certain embodiments, the device is a non-pressurized dispenser delivering a spray containing a metered dose of the active ingredient. In certain embodiments, each delivered dose contains 100 μL.

The droplet size distribution (was investigated as a function of device age and storage according to established and validated testing methods. A Malvern Spray Tec 2.0 with automated device actuation was used for determining the droplet size distribution of Naloxone Nasal Spray. Spraytec laser diffraction system allows measurement of spray droplet size distributions in real-time. Droplet Size Distribution: As reported from the Malvern Spraytec, the distribution is a cumulative volume distribution characterized by the Dv(10), Dv(50), and Dv(90). %<10 μm. Data concerning droplet size distribution are summarized in Tables 21 and 23.

The spray pattern is the shape of the plume when looking downward on the nasal spray unit as the product is emitted from the nasal spray unit. Spray pattern was also investigated as a function of device age and storage. Ovality is the ratio of $D_{max}/D_{min}$, where $D_{max}$ and $D_{min}$ are the length of the longest and shortest line respectively in mm that passes through the weighted center of mass drawn within the parameter of the spray pattern. A SPRAYVIEW, from PROVERIS measurement systems, was used to measure spray pattern and plume geometry. Both the Sprayview and Spraytec systems have been validated. Data concerning spray pattern are summarized in Tables 22 and 24. The procedures of these tests comply with the testing contained in the FDA's Guidance for Industry ("Nasal Spray and Inhalation Solution, Suspension, and Spray Drug Products—Chemistry, Manufacturing, and Controls Documentation," July 2002).

TABLE 21

Droplet size distribution from 2 mg naloxone intranasal device.

| | Batch # | Storage orientation | Storage temp (° C.) | Dv(90) (μm) | % < 10 μm |
|---|---|---|---|---|---|
| 3 cm spray | 1 | horizontal | 25° | 70.87 | 1.215 |
| | 2 | inverted | 25° | 70.05 | 1.218 |
| | 2 | upright | 25° | 69.13 | 0.269 |

TABLE 21-continued

Droplet size distribution from 2 mg naloxone intranasal device.

| | Batch # | Storage orientation | Storage temp (° C.) | Dv(90) (μm) | % < 10 μm |
|---|---|---|---|---|---|
| | 3 | inverted | 40° | 66.74 | 1.628 |
| | 3 | upright | 25° | 67.2 | 1.112 |
| | 3 | upright | 40° | 67.2 | 1.112 |
| 6 cm spray | 1 | horizontal | 25° | 63.74 | 1.647 |
| | 2 | inverted | 25° | 69.02 | 1.752 |
| | 2 | upright | 25° | 64.81 | 1.634 |
| | 3 | inverted | 40° | 66.52 | 1.713 |
| | 3 | upright | 25° | 69.36 | 0.777 |
| | 3 | upright | 40° | 69.36 | 0.777 |

TABLE 22

Spray pattern from 2 mg naloxone intranasal device.

| | Batch # | Storage orientation | Storage temp (° C.) | Ovality ratio |
|---|---|---|---|---|
| 3 cm spray | 2 | inverted | 25° | 1.165 |
| | 3 | inverted | 40° | 1.257 |
| | 3 | upright | 40° | 1.308 |
| | 3 | upright | 40° | 1.278 |
| | 3 | upright | 40° | 1.308 |
| | 4 | inverted | 25° | 1.054 |
| | 4 | upright | 25° | 1.168 |
| | 4 | upright | 25° | 1.204 |
| 6 cm spray | 2 | inverted | 25° | 1.684 |
| | 3 | inverted | 40° | 1.365 |
| | 3 | inverted | 40° | 1.041 |
| | 3 | upright | 40° | 1.33 |
| | 3 | upright | 40° | 1.187 |
| | 4 | inverted | 25° | 1.304 |
| | 4 | upright | 25° | 1.367 |
| | 4 | upright | 25° | 1.59 |

TABLE 23

Droplet size distribution from 4 mg naloxone intranasal device.

| | Batch # | Storage orientation | Storage temp (° C.) | Dv(90) (μm) | % < 10 μm |
|---|---|---|---|---|---|
| 3 cm spray | 1 | horizontal | 25° | 70.87 | 1.215 |
| | 2 | inverted | 25° | 73.85 | 0.524 |
| | 3 | upright | 40° | 76.74 | 1.082 |
| | 3 | inverted | 40° | 73.86 | 1.467 |
| 6 cm spray | 1 | horizontal | 25° | 66.74 | 1.647 |
| | 2 | inverted | 25° | 67.49 | 1.606 |
| | 3 | upright | 40° | 80.99 | 1.031 |
| | 3 | inverted | 40° | 69.94 | 1.699 |

TABLE 24

Spray pattern from 4 mg naloxone intranasal device.

| | Batch # | Storage orientation | Storage temp (° C.) | Ovality ratio |
|---|---|---|---|---|
| 3 cm spray | 1 | upright | 25° | 1.511 |
| | 2 | upright | 40° | 1.557 |
| | 3 | inverted | 25° | 1.169 |
| | 3 | upright | 40° | 1.215 |
| | 3 | inverted | 40° | 1.475 |
| 6 cm spray | 1 | upright | 25° | 1.435 |
| | 2 | upright | 40° | 1.428 |
| | 3 | inverted | 25° | 1.077 |
| | 3 | upright | 40° | 1.164 |
| | 3 | inverted | 40° | 2.076 |

Pharmaceutical compositions comprising naloxone hydrochloride (1% w/v) were tested for stability in room temperature/light conditions, room temperature/dark conditions and in 25° C./60% RH (protected from light). It was tested for pH, purity, and impurities at an initial time point, 2 months and 10 months. Results are given in Table 25.

TABLE 25

Naloxone storage stability.

| Storage condition | Test interval (months) | Appearance | pH | Assay (% of label claim) | Impurities (area %) |
|---|---|---|---|---|---|
| | Initial | Clear, colorless solution | 4.5 | 101 | Not detected |
| 25° C./60% RH | 2 | Not analyzed | 4.5 | Not analyzed | Not analyzed |
| | 10 | Clear, colorless solution | 4.5 | 95 | 0.2 |
| Room temperature/light | 10 | Clear, yellow solution | 4.4 | 92 | 1.3 |
| Room temperature/dark | 10 | Clear, colorless solution | 4.5 | 97 | 0.3 |

Example 4: Reliability of Use by Untrained Personnel

The intranasal delivery provides a quick, simple and effective solution for those bystanders, friends or family members that are in a position to give aid to an overdose victim.

Qualitative Study which consisted of 3 consecutive and iterative Human Factors/Label Comprehension Pre-Tests, was conducted over a 5-day period to assess the ability of subjects to understand the labelling (Patient Insert and Quick Start Guide (QSG)) and to demonstrate simulated use of a naloxone nasal prototype device.

The purpose of this testing schedule was to learn and adjust the labelling and materials in an iterative and accelerated manner. The objectives of the study were:

To evaluate the subject's ability to correctly demonstrate the steps for evaluating a patient for the medication, administering the medication, monitoring the patient and, if appropriate, giving a second dose, as instructed in the QSG (Human Factors);

To evaluate the subject's ability to comprehend key messages in the Patient Insert (Comprehension);

To assess the study flow and study tools (Self-Administered Questionnaire and Observer Checklist), To evaluate 2 different labelling versions for clarity.

Post the qualitative studies the device and label were validated in quantitative studies Two human factors validation studies were conducted in a general population (GP) of individuals 12 years of age and older. Formative research was completed in advance of the validation work in order to optimize the labeling and help inform the study design. The validation studies were conducted in order to evaluate the ability of subjects to correctly complete 2 critical tasks (insert nozzle into nostril and press plunger to release dose into nose) from the Quick Start Guide (QSG).

Study 1: The first study evaluated two devices, with two units contained in the kit to be administered 2-3 minutes apart.

Study 2: The second study evaluated a single device.

Additionally, comprehension of key elements of the Patient Information (PI) section of the Prescribing Information was also evaluated. The design for the Study 1 informed the design of the Study 2; the primary endpoints and protocols for the studies were very similar. The methods and findings of these two studies are summarized in Table 26 below.

TABLE 26

Reliability of intranasal naloxone administration by untrained personnel.

| | COMPARATIVE STUDY CRITERIA | Study1 | Study 2 |
|---|---|---|---|
| Methodology | Study Population-General Population, 12 years of age and older | ✔ | ✔ |
| | Study population included subgroups of low literate subjects (~25%) and adolescent subjects ages 12-17 (~25%). | ✔ | ✔ |
| | None of the subjects were provided with any training on how to use the device. | ✔ | ✔ |
| | Included 'Study Arms': | | |
| | Arm 1 (Review QSG in Advance): Subjects were presented with the Quick Start Guide to review prior to the demonstration | Both Arm 1 (n = 32) & Arm 2 (n = 31) | Arm 2 only (n = 53) |
| | Arm 2 (Do not review QSG in Advance): Subjects were presented with a 'worst case' scenario in which they had to use and interpret the labeling at the time of an emergent situation, such as finding an individual unconscious. | | |
| | Primary Objectives (Human Factors)- | | |
| | correct completion of the critical tasks: Insert nozzle into nostril (Task 2a) Press plunger to release dose into nose (Location-Task 2b; Dose Released-Task 2c) | ✔ | ✔ |
| | Success Threshold (lower bound of the 95% exact confidence interval) for combined critical tasks completion | 69% | 73% |
| | Secondary Objectives (Human Factors): | | |
| | Check for response (Task 1a) Call 911 (Task 3a) Move to Recovery Position after administering dose (Task 3b) | ✔ a | ✔ |
| | Primary Objectives (Comprehension): | | |
| | Product Indication (product use) (Q.1) Product Indication (medical treatment) (Q.2) How NASAL should be used (Q.8) Get emergency medical help after using NASAL (Q.6) Signs of opioid overdose (Q.7) Potential withdrawal symptoms after use of NASAL (Q.4) | ✔ | ✔ |
| | Secondary Objectives (Comprehension): | | |
| | Whether NASAL can be used for overdoses not caused by opioids (Q.3) When a patient should talk to a healthcare provider before use (Q.5) Who should not use the product (Q.9) | ✔ | ✔ |
| | Inclusion Criteria: | | |
| | The following inclusion criteria applied to all participants: 1. The subject was male or female, of any race. 2. The subject was 12 years of age or older 3. The subject must have been able to read, speak and understand English sufficiently to understand the nature of the study procedures. 4. At the study site, the subject must have agreed to follow the specified instructions and procedures and must have voluntarily signed the CDA and the Informed Consent/Assent form. If the subject was less than 18 years of age: a parent/guardian must have been present to sign the Consent/Assent form and give permission for adolescent to participate. | ✔ | ✔ |
| | Exclusion Criteria: | | |
| | The following exclusion criteria applied to all participants: 1. The subject had ever been trained or employed as a healthcare professional (physician, nurse, nurse practitioner, physician assistant, or pharmacist). 2. The subject or anyone in their household currently worked for a marketing, marketing consulting, or marketing research company, an advertising agency or public relations firm, a pharmaceutical company, a pharmacy, a managed care or health insurance | ✔ | ✔ |

TABLE 26-continued

Reliability of intranasal naloxone administration by untrained personnel.

| | COMPARATIVE STUDY CRITERIA | Study1 | Study 2 |
|---|---|---|---|
| | company as a healthcare professional, a healthcare practice, or a public health agency such as Health and Human Services or the FDA.<br>3. The subject had, or could not remember if he/she had, participated in any clinical trial, product label study or market research study in the past twelve (12) months.<br>4. The subject normally wore corrective lenses, contacts or glasses to read and did not have them with them.<br>5. The subject had any other impairment that would prevent him/her from being able to read on his/her own. | | |
| Results | Primary Objectives (Human Factors): | | |
| | Success Threshold met<br>(Correct performance of both critical tasks)<br>Insert nozzle into nostril (Task 2a)<br>Press plunger to release dose into nose<br>(Location - Task 2b; Dose Released - Task 2c)<br>Secondary Objectives (Human Factors): | Yes-both arms above 69% LB threshold | Yes-above 73% LB threshold |
| | Two of three objectives tested across both waves scored higher than 70% PE:<br>Check for a Response (Task 1a)<br>Immediately Call 911 (Task 3a)<br>Move to Recovery Position (Task 3b) scored lowest across both waves, particularly for subjects who did not review the QSG prior to the demonstration<br>Primary Objectives (Comprehension): | ✔ b | ✔ |
| | 4 objectives scored 90% PE or higher across both waves:<br>Q.1 - Product Indication (product use)<br>Q.8 - How NASAL should be used<br>Q.6 - Necessary to get emergency medical help after using NASAL<br>Q.7 - Signs of opioid overdose<br>objectives scored 77% PE or higher across both waves:<br>Q.4 - Potential withdrawal symptoms after use of NASAL<br>Q.2 - Product Indication (medical treatment)<br>Exploratory Objectives - (Comprehension): | ✔ | ✔ |
| | Scores were relatively consistent across study waves:<br>Q.3 - Whether NASAL can be used for overdoses not caused by opioids<br>Q.5 - When a patient should talk to a healthcare provider before use<br>Q.9 - Who should not use the product | Scores ranged from 79%-92% | Scores ranged from 70%-93% | a Also included 2 additional secondary human factors objectives [Wait 2-3 minutes and assess effectiveness of 1st dose; Re-administer using a new unit (if needed)]; these were not applicable for Study 2.
b Study 1 included two additional secondary human factors objectives-Wait 2-3 minutes and assess effectiveness of 1st dose (Task 4a); Re-administer using a new unit (if needed) (Task 4c). Subjects who reviewed the QSG prior to the demonstration scored directionally higher than subjects who did not for the actions related to these objectives.

Conclusion:

Subjects demonstrated the ability to correctly perform both critical tasks and performed better than the success threshold in both studies (Study 1—Arm 1: 90.6% PE, 74.98% LB; Study 1—Arm 2: 90.3% PE, 74.25% LB; Study 2: 90.6% PE, 79.34% LB), to use the device and deliver a dose of the medication safely and effectively without any training and with no prior review of instructions. Subjects did not demonstrate two secondary tasks as ably; only 59.4% of Arm 1 and 54.8% of Arm 2 correctly administered the dose within 2-3 minutes of the first dose, and 80.0% (Arm 1) and 70.0% (Arm 2) correctly administered a second dose. Comprehension scores were also very high for the most critical comprehension objectives [product indication (medical treatment), product indication (product use), get emergency medical help after using product, how product should be used, sign of opioid overdose]. The results suggest that this product can be safely used by a bystander population with little or no training or advanced review of instructions.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

This application incorporates by reference the disclosures of patent applications no. U.S. Ser. No. 61/953,379, filed Mar. 14, 2014; U.S. Ser. No. 14/659,472, filed Mar. 16, 2015; PCT/UB2015/000941, filed Mar. 16, 2015; U.S. Ser.

No. 62/022,268, filed Jul. 9, 2014; U.S. Ser. No. 14/795,403, filed Jul. 9, 2015; and PCT/US15/39720, filed Jul. 9, 2015.

What is claimed is:

1. A method of treating opioid overdose, the method comprising:
   delivering a 25-200 μL spray of a pharmaceutical solution from a pre-primed device into a nostril of a patient,
   wherein the device is adapted for nasal delivery,
   wherein the spray delivers between about 4 mg and about 10 mg naloxone, an isotonicity agent, and between about 0.005% and about 0.015% (w/v) of benzalkonium chloride.

2. The method of claim 1, wherein the spray delivers about 4 mg naloxone.

3. The method of claim 2, wherein the spray delivers about 100 μL of the pharmaceutical solution comprising:
   about 4% (w/v) naloxone hydrochloride;
   about 0.74% (w/v) sodium chloride;
   about 0.01% (w/v) benzalkonium chloride; and
   about 0.1% (w/v) disodium edetate.

4. The method of claim 1, wherein the spray delivers about 5 mg naloxone.

5. The method of claim 1, wherein the spray delivers about 6 mg naloxone.

6. The method of claim 1, wherein the spray delivers about 7 mg naloxone.

7. The method of claim 1, wherein the spray delivers about 8 mg naloxone.

8. The method of claim 1, wherein the spray delivers about 9 mg naloxone.

9. The method of claim 1, wherein the spray delivers about 10 mg naloxone.

10. The method of claim 9, wherein less than about 5% of the pharmaceutical solution leaves the nasal cavity via drainage into the nasopharynx or externally.

11. The method of claim 9, wherein less than about 20% of the pharmaceutical solution leaves the nasal cavity via drainage into the nasopharynx or externally.

12. The method of claim 11, wherein less than about 10% of the pharmaceutical solution leaves the nasal cavity via drainage into the nasopharynx or externally.

13. The method of claim 1, wherein the spray is delivered as a round spray plume with an ovality ratio less than about 2.0 when measured at 3 cm.

14. The method of claim 13, wherein the ovality ratio is less than about 1.2 when measured at 3 cm.

15. The method of claim 14, wherein the ovality ratio is less than about 1.1 when measured at 3 cm.

16. The method of claim 13, wherein the ovality ratio is less than about 1.5 when measured at 3 cm.

17. The method of claim 16, wherein the ovality ratio is less than about 1.3 when measured at 3 cm.

18. The method of claim 1, wherein the patient is an opioid overdose patient or a suspected opioid overdose patient.

19. The method of claim 18, wherein the patient exhibits one or more symptoms chosen from: respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing, erratic or stopped pulse, choking or gurgling sounds, blue or purple fingernails or lips, slack or limp muscle tone, contracted pupils, and vomiting.

20. The method of claim 19, wherein the patient exhibits respiratory depression or cardiovascular depression.

21. The method of claim 20, wherein the respiratory depression is caused by the illicit use of opioids, or by an accidental misuse of opioids.

22. The method of claim 18, wherein the patient is free from respiratory depression for at least about 2 hours following treatment comprising delivery of the therapeutically effective amount of the opioid antagonist.

23. The method of claim 18, wherein the patient is free from respiratory depression for at least about 6 hours following treatment comprising delivery of the therapeutically effective amount of the opioid antagonist.

24. The method of claim 18, wherein the device comprises a reservoir not more than about 140 μL in volume.

25. The method of claim 1, wherein said single actuation yields a plasma concentration of ≥0.2 ng/mL within 2.5 minutes in said patient.

26. The method of claim 25, wherein said single actuation yields a plasma concentration of ≥1 ng/mL within 5 minutes in said patient.

27. The method of claim 26, wherein said single actuation yields a plasma concentration of ≥3 ng/mL within 10 minutes in said patient.

28. The method of claim 1, wherein said single actuation yields a plasma concentration of ≥0.2 ng/mL within 2.5 minutes in said patient.

29. The method of claim 28, wherein said single actuation yields a plasma concentration of ≥1 ng/mL within 5 minutes in said patient.

30. The method of claim 1, wherein approximately 100 μL of the pharmaceutical solution is delivered by one actuation of the device.

31. The method of claim 30, wherein the isotonicity agent is present in a concentration between about 0.2% and about 1.2% (w/v).

32. The method of claim 31, wherein the pharmaceutical solution further comprises between about 0.1% and about 0.5% (w/v) of a stabilizing agent and an amount of an acid sufficient to achieve a pH between about 3.5 and about 5.5.

33. The method of claim 32, wherein:
   the isotonicity agent is sodium chloride;
   the stabilizing agent is disodium edetate; and
   the acid is hydrochloric acid.

34. The method of claim 33, wherein the pharmaceutical solution comprises:
   about 4% (w/v) naloxone hydrochloride;
   about 0.74% (w/v) sodium chloride;
   about 0.01% (w/v) benzalkonium chloride; and
   about 0.1% (w/v) disodium edetate.

35. The method of claim 1, wherein the device has a single reservoir containing approximately 125 μL of the pharmaceutical solution.

36. The method of claim 1, further comprising storing the device for about twelve months or less at 25° C. and 60% relative humidity prior to actuating the device, wherein the device retains at least about 100% of initial naloxone hydrochloride content at actuation.

37. The method of claim 1, wherein the device comprises a reservoir, a piston, and a swirl chamber.

38. The method of claim 37, wherein the device comprises a plunger that houses a container closure comprising
   a vial comprising an opening,
   a cannula, and
   a rubber stopper,
      wherein the stopper is configured to occlude the opening of the vial, and wherein the cannula is configured such that the cannula can pierce the stopper when the plunger applies sufficient force to the cannula.

39. The method of claim 1, wherein delivery time is less than about 25 seconds.

40. The method of claim 39, wherein delivery time is less than about 20 seconds.

41. A method of treating narcotic-induced respiratory depression, the method comprising:
delivering a 25-200 µL spray of a pharmaceutical solution from a pre-primed device into a nostril of a patient in need thereof in a manner that delivers the pharmaceutical solution in a round spray plume with an ovality ratio less than about 2.0 when measured at 3 cm,
wherein the device is adapted for nasal delivery,
wherein the spray delivers between about 4 mg and about 10 mg naloxone, an isotonicity agent, and between about 0.005% and about 0.015% (w/v) of benzalkonium chloride,
wherein the patient is in a lying, supine, or recovery position, and
wherein the patient experiences a geometric mean naloxone $C_{max}$ not less than about 3 ng/mL following a single spray.

42. The method of claim 41, wherein said single actuation yields a plasma concentration of ≥3 ng/mL within 10 minutes in said patient.

43. The method of claim 42, wherein said single actuation yields a plasma concentration of ≥0.2 ng/mL within 2.5 minutes in said patient.

44. The method of claim 43, wherein said single actuation yields a plasma concentration of ≥1 ng/mL within 5 minutes in said patient.

45. The method of claim 41, wherein the patient experiences a geometric mean naloxone $C_{max}$ not less than about 3 ng/mL following a single spray.

46. The method of claim 45, wherein the patient experiences a plasma naloxone concentration such that the geometric mean of area under a plasma concentration versus time curve ($AUC_{0-\infty}$) is not less than about 8 hr*ng/mL when time is extrapolated to infinity.

* * * * *